United States Patent
Hakim

(10) Patent No.: US 11,752,315 B1
(45) Date of Patent: Sep. 12, 2023

(54) METHOD OF TREATING NORMAL PRESSURE HYDROCEPHALUS

(71) Applicant: Carlos A. Hakim, Coconut Grove, FL (US)

(72) Inventor: Carlos A. Hakim, Coconut Grove, FL (US)

( * ) Notice: Subject to any disclaimer, the term of this patent is extended or adjusted under 35 U.S.C. 154(b) by 486 days.

(21) Appl. No.: 16/896,957

(22) Filed: Jun. 9, 2020

Related U.S. Application Data

(63) Continuation of application No. 15/726,198, filed on Oct. 5, 2017, now abandoned.

(Continued)

(51) Int. Cl.
*A61M 27/00* (2006.01)
*A61B 5/03* (2006.01)
*A61B 5/00* (2006.01)

(52) U.S. Cl.
CPC ......... *A61M 27/006* (2013.01); *A61B 5/0042* (2013.01); *A61B 5/031* (2013.01); *A61B 5/032* (2013.01)

(58) Field of Classification Search
CPC ........ A61M 27/006; A61M 2210/0693; A61M 2027/004; A61M 2202/0464; A61M 2205/3344; A61M 25/007; A61M 25/04; A61M 27/002; A61M 2205/3331; A61M 2205/3334; A61M 2205/3523; A61M 2205/52; A61M 2205/8206; A61M 2210/0687; A61M 2210/1003; A61M 2210/125; A61M 2230/30; A61M 25/0074; A61M 27/00; A61M 39/22; A61M 11/005; A61M 1/00; A61M 1/0019; A61M 1/0023; A61M 1/0031; A61M 1/0062; A61M 1/008; A61M 1/285; A61M 2025/0002; A61M 2025/0042; A61M 2025/0073; A61M 2025/0166; A61M 2025/0175; A61M 2025/0213; A61M 2039/0258; A61M 2039/0273; A61M 2039/0276; A61M 2039/062; A61M 2039/226;

(Continued)

(56) References Cited

U.S. PATENT DOCUMENTS 3,288,142 A 11/1966 Hakim
3,516,410 A 6/1970 Hakim
(Continued)

OTHER PUBLICATIONS

Urs D. Schmid et al., Management of obstructive hydrocephalus secondary to posterior fossa tumors by steroids and subcutaneous ventricular catheter reservoir, Nov. 1986, J. Neruosurg., vol. 65, p. 649-653 (Year: 1986).*

(Continued)

*Primary Examiner* — Jessica Arble
*Assistant Examiner* — Alessandro R Del Priore
(74) *Attorney, Agent, or Firm* — Lando & Anastasi, LLP

(57) ABSTRACT

A ventricular shunt assembly, used in conjunction with a hyperbaric environment (e.g., having a pressure of about 250 to about 350 mm $H_2O$ above atmospheric pressure) can be used to correct a patient's intraparenchymal venous pressure from a sub-normally low value to a normal value. The shunt may comprise a valve, e.g., and adjustable valve, disposed between the ventricular catheter and the distal catheter. Optionally, the shunt comprises a reservoir on the ventricular side of the valve.

21 Claims, 50 Drawing Sheets

Related U.S. Application Data

(60) Provisional application No. 62/405,662, filed on Oct. 7, 2016.

(58) Field of Classification Search
CPC .. A61M 2039/2493; A61M 2205/0238; A61M 2205/0266; A61M 2205/3306; A61M 2205/3341; A61M 2205/3507; A61M 2205/3515; A61M 2205/3584; A61M 2205/3606; A61M 2205/366; A61M 2205/3673; A61M 2205/502; A61M 2205/8268; A61M 2210/101; A61M 2210/1021; A61M 2210/1075; A61M 2210/12; A61M 2230/005; A61M 2230/06; A61M 2230/10; A61M 2230/20; A61M 2230/42; A61M 2230/50; A61M 2230/63; A61M 25/0017; A61M 25/0023; A61M 25/0026; A61M 25/0029; A61M 25/0041; A61M 25/0068; A61M 25/0075; A61M 25/0102; A61M 25/0108; A61M 25/02; A61M 25/0668; A61M 25/09; A61M 25/10; A61M 25/10183; A61M 25/10185; A61M 31/002; A61M 39/0247; A61M 39/06; A61M 39/24; A61M 5/14248; A61M 5/14276; A61M 5/145; A61M 5/158; A61M 5/1723; A61M 5/3291; A61M 5/3298; A61M 5/44; A61B 5/0042; A61B 5/031; A61B 5/032; A61B 2576/026; A61B 2010/0077; A61B 8/04; F16K 2099/0088; F16K 15/026; F16K 31/088; F16K 99/0015; F16K 99/0038; F16K 99/0057

See application file for complete search history.

(56) References Cited

U.S. PATENT DOCUMENTS

| | | | |
|---|---|---|---|
| 3,527,226 | A | 9/1970 | Hakim |
| 3,877,137 | A | 4/1975 | Hakim et al. |
| 3,886,948 | A | 6/1975 | Hakim |
| 3,889,687 | A | 6/1975 | Harris et al. |
| 3,958,562 | A | 5/1976 | Hakim et al. |
| 4,106,510 | A | 8/1978 | Hakim et al. |
| 4,312,293 | A | 1/1982 | Hakim |
| 4,332,255 | A | 6/1982 | Hakim et al. |
| 4,387,715 | A | 6/1983 | Hakim et al. |
| 4,551,128 | A | 11/1985 | Hakim et al. |
| 4,595,390 | A | 6/1986 | Hakim et al. |
| 4,608,992 | A | 9/1986 | Hakim et al. |
| 4,615,691 | A | 10/1986 | Hakim et al. |
| 4,772,257 | A | 9/1988 | Hakim et al. |
| 5,772,607 | A | 6/1998 | Magram |
| 5,928,182 | A | 7/1999 | Kraus et al. |
| 6,455,494 | B1 | 9/2002 | Jefferies et al. |
| 7,309,330 | B2 | 12/2007 | Bertrand et al. |
| 8,008,492 | B2 | 8/2011 | Giralt Lledo et al. |
| 8,026,209 | B2 | 9/2011 | Gaillard et al. |
| 8,124,095 | B2 | 2/2012 | Pardridge et al. |
| 8,142,781 | B2 | 3/2012 | Pardridge et al. |
| 8,242,088 | B2 | 8/2012 | Joliot et al. |
| 8,383,107 | B2 | 2/2013 | Muruganandam et al. |
| 8,535,656 | B2 | 9/2013 | Kabanov et al. |
| 8,545,812 | B2 | 10/2013 | Hong et al. |
| 8,546,319 | B2 | 10/2013 | Starr et al. |
| 8,609,103 | B2 | 12/2013 | Zankel et al. |
| 8,613,929 | B2 | 12/2013 | Gaillard et al. |
| 8,629,114 | B2 | 1/2014 | Walz |
| 8,637,648 | B1 | 1/2014 | Mash et al. |
| 2009/0130019 | A1 | 5/2009 | Tobinick |
| 2012/0315282 | A1 | 12/2012 | Bedinger et al. |

OTHER PUBLICATIONS

Park et al., Accuracy and Safety of Bedside External Ventricular Drain Placement at Two Different Cranial Sites : Kocher's Point versus Forehead, 2011, J Korean Neurosurg Soc 50, p. 317-321 (Year: 2011).*

Harold D. Portnoy et al. The relationship of intracranial venous pressure to hydrocephalus, Apr. 1994, Child's Nerv Syst, vol. 10, p. 29-35 (Year: 1992).*

Verena Speck et al. Lumbar Catheter for Monitoring of Intracranial Pressure in Patients with Post-Hemorrhagic Communicating Hydrocephalus, Oct. 2010, NeruocritCare, vol. 14, p. 218-215 (Year: 2010).*

Hayakawa et al., Response of cerebrospinal fluid pressure to hyperbaric oxygenation, 1971, Neurol. Neurosurg. Psychiat., vol. 34, p. 580-586 (Year: 1971).*

Lin Yang et al.,The Clinical Effect of Postoperative Hyperbaric Oxygen Therapy on Idiopathic Normal Pressure Hydrocephalus: A Retrospective and Comparative Analysis of 61 Patients with Ventriculoperitoneal Shunt, May 2017, World Neurosurg., vol. 103, p. 376-380 (Year: 2017).*

Integra, Shunt System Reservoirs, 2018, p. 1-6 (Year: 2018).*

Heitaro Mogami et al., Clinical Application of Hyperbaric Oxygenation in the Treatment of Acute Cerebral Damage, Dec. 1969, J. Neurosurg., vol. 31, p. 636-643 (Year: 1969).*

Baechli et al., "Hyperbaric Oxygen Therapy (HBO) for the Treatment of an Epidural Abscess in the Posterior Fossa in an 8-Month-Old Infant", Pediatric Neurosurgery, 2008; 44:239-242.

Bueno et al., Enhancement of confocal microscopy images using Mueller-matrix polarimetry. Journal of Microscopy, vol. 235, Pt 1 2009, pp. 84-93.

Canham et al., "Layered collagen fabric of cerebral aneurysms quantitatively assessed by the universal stage and polarized light microscopy", The Anatomical Record, 231 :579-592, 1991.

Fleckenstein et al., "This technology is relatively easy and non-invasive, but can be a valuable asset in diagnosing retinal disease", Rev of Opthal., Aug. 12, 2010.

Gabb et al., "Hyperbaric Oxygen* a Therapy in Search of Diseases", Chest, 92(6):1074-1082, 1987.

Goldstein, et al., "Phorbol Ester-induced Inhibition of Collagen Accumulation by Human Lung Fibroblasts", The Journal of Biological Chemistry 265:23 pp. 13623-13628 (1990).

Hakim The Physics and Physicopathology of the Hydraulic Complex of the Central Nervous System (The Mechanics of Hydrocephalus and Normal Pressure Hydrocephalus), Massachusetts Institute of Technology, pp. 1-157 (1985).

Hakim et al., "Normal-Pressure Hydrocephalus" Neurosurgery Clinics of North America, vol. 36, No. 4 pp. 761-773 (2001).

Jones, et al., "Hydrocephalus 2008, Sep. 17-20, Hannover Germany: a conference report," 16, Cerebrospinal Fluid Research 5:19 (2008).

Julow et al., Polarization Microscopic Investigation of Subarachnoid Fibrosis after Subarachnoid Haemorrhage. Acta Neurochirurgica 53, 237-245 (1980).

Li et al., Myocardial extracellular matrix remodeling in transgenic mice overexpressing tumor necrosis factor alpha can be modulated by anti-tumor necrosis factor a therapy. 12746-12751 u PNAS u Nov. 7, 2000 u vol. 97 u No. 23.

MacDonald et al. Annals Biomed Engin., 28:533-542, 2000.

Marshall et al., Ultrastructural distribution of collagen types I-VI in aging human retinal vessels. British Journal of Ophthalmology, 1990,74,228-232.

Motohashi et al., Subarachnoid Haemorrhage Induced Proliferation of Leptomeningeal Cells and Deposition of Extracellular Matrices in the Arachnoid Granulations and Subarachnoid Space. Acta Neurochir (Wien) (1995) 136:88-91.

Nwogu, et al., "Inhibition of Collagen Synthesis With Prolyl 4-Hydroxylase Inhibitor Improves Left Ventrical Function and Alters the Patter of Left Ventricular Dilatation After Myocardial Infarction" Circulation 104, pp. 2216-2221 (2001).

(56) References Cited

OTHER PUBLICATIONS

Pischon, et al., "Regulation of Collagen Deposition and Lysyl Oxidase by Tumor Necrosis Factor in Osteoblasts" The Journal of Biological Chemistry 279:29, pp. 30060-30065 (2004).
Rockswold et al., A prospective, randomized clinical trial to compare the effect of hyperbaric to normobaric hyperoxia on cerebral metabolism, intracranial pressure, and oxygen toxicity in severe traumatic brain injury. J Neurosurg 112:1080-1094, 2010.
Sajanti et al., "Rapid Induction of Meningeal Collagen Synthesis in the Cerebral Cisternal and Ventricular Compartments after Subarachnoid Hemorrhage", Acta Neurochir. (Wien), 2001, pp. 821-826.
Shprecher, et al., Normal Pressure Hydrocephalus: Diagnosis and Treatment, Current Neurology & Neuroscience Reports 8:5, pp. 371-376 (2008).
Tobinick et al., TNF-alpha Modulation for Treatment of Alzheimer's Disease: A 6-Month Pilot Study. MedGenWed. 2006; 8(2): 25.
Weaver, Lindell, "Hyperbaric Medicine for the Hospital-Based Physician", Hospital Practice, 2012, vol. 40, pp. 88-101 (Abstract only).
Whittaker et al., "The Molecular Organization of Collagen in Saccular Aneurysms Assessed by Polarized Light Microscopy", Connective Tissue Res. 17(1):43-54, 1988.
Zhi et al., Hyperbaric oxygenation therapy of Normal Pressure Hydrocephalus, European Underwater and Baromedical Society, Annual Meeting Abstract S.217, Sep. 4-8, 1996.
Kohsi et al., "Intracranial Pressure Responses During Hyperbaric Oxygen Therapy" Neurol Med Chir (Tokyo) 1991, 31: pp. 575-581.
Berisha et al., "Retinal Abnormalities in Early Alzheimer's Disease" IOVS 2007, 48: pp. 2285-2289.
McGrory et al., "The application of retinal fundus camera imaging in dementia: A systematic review" Alzheimer's & Dementia, Assessment & Disease Monitoring 2017, 6: pp. 91-107.
Tarkowski et al., "Normal pressure hydrocephalus triggers intrathecal production of TNF-alpha", Neurobiology of Aging, vol. 24, 2003, pp. 707-714.
Bateman et al., "The role of altered impedance in the pathophysiology of normal pressure hydrocephalus, Alzheimer's disease and syringomyelia", Medical Hypotheses, vol. 63, 2004, pp. 980-985.
Li et al., "Expression of TGF betas and TGF beta type II receptor in cerebrospinal fluid of patients with idiopathic normal pressure hydrocephalus", Neuroscience Letters, vol. 413, 2007, pp. 141-144.
Tada et al., "Intraventricular administration of hepatocyte growth factor treats mouse communicating hydrocephalus induced by transforming growth factor 8l", Neurobiology of Disease, vol. 21, 2006, pp. 576-586.
Noda et al., "Very Low-pressure Hydrocephalus: A New Clinical Entity and Issues of Treatment", Journal of Medical Science, vol. 23, No. 2, pp. 109-114, Jun. 2011.
Schmid et al., "Management of obstructive hydrocephalus secondary to posterior fossa tumors by steroids and subcutaneous ventricular catheter reservoir" J. Neurosurg., 1986, vol. 65, pp. 649-653.
Park et al., "Accuracy and Safety of Bedside External Ventricular Drain Placement at Two Different Cranial Sites: Kocher's Point versus Forehead" J. Korean Neurosurg. Soc., 2011, vol. 50, pp. 317-321.
Portnoy et al., "The relationship of intracranial venous pressure to hydrocephalus" Child's Nerv. Syst., 1994, vol. 10, pp. 29-35.
Speck et al., "Lumbar Catheter for Monitoring of Intracranial Pressure in Patients with Post-Hemorrhagic Communicating Hydrocephalus" Neurocrit. Care, 2010, vol. 14, pp. 208-215.
Hayakawa et al., "Response of cerebrospinal fluid pressure to hyperbaric oxygenation" Neurol. Neurosurg. Psychiat., 2017, vol. 34, pp. 580-586.
Yang et al., "The Clinical Effect of Postoperative Hyperbaric Oxygen Therapy on Idiopathic Normal Pressure Hydrocephalus: A Retrospective and Comparative Analysis of 61 Patients with Ventriculoperitoneal Shunt" World Neurosurg., 2017, vol. 103, pp. 376-380.
Mogami et al., "Clinical Application of Hyperbaric Oxygenation in the Treatment of Acute Cerebral Damage", J. Neurosurg., 1969, vol. 31, pp. 636-643.

* cited by examiner

Normal Brain

Hydrocephalic Brain

METHOD OF TREATING NORMAL PRESSURE HYDROCEPHALUS

CLAIM OF PRIORITY

The present application is a Continuation of U.S. Ser. No. 15/726,198, filed Oct. 5, 2017, which claims priority from U.S. Ser. No. 62/405,662, filed Oct. 7, 2016, which is incorporated by reference in its entirety.

BACKGROUND OF THE INVENTION

Hydrocephalus is a condition associated with ventricular enlargement caused by a net accumulation of fluid in the ventricles. Non-communicating (or obstructive) hydrocephalus is hydrocephalus associated with an obstruction in the ventricular system and is generally characterized by increased cerebrospinal fluid (CSF) pressure. In contrast, communicating (or non-obstructive) hydrocephalus is a form of hydrocephalus which does not arise from a visible blockage in the flow of cerebrospinal fluid. Normal Pressure Hydrocephalus (NPH), a form of communicating hydrocephalus, is a clinical condition which principally affects the elderly. It is characterized by a triad of symptoms: Motor disturbances (mostly gait impairment), incontinence and dementia; associated with ventricular enlargement in the absence of elevated intracranial pressure. (Hakim et al. (1965). *J Neurol Sci* 2: 307-327; Verees et al. Management of Normal Pressure Hydrocephalus. *American Family Physician* (2004) available at www.aafp.org/afp/2004/0915/p1071.html). In summary, NPH presents as an enlargement of the ventricles with a normal CSF pressure. NPH is a known and unique clinical entity justifying its own differential diagnosis with other brain atrophies.

There is a need in the art for improved treatments for NPH.

SUMMARY OF THE INVENTION

In this application, the following nomenclature is used:
$P_{csf}$=Intraventricular CSF pressure
$P_{sa}$=Subarachnoid CSF pressure
$P_v$=Extraparenchymal venous pressure, measured in the Superior Sagittal Sinus
$P_p$=Intraparenchymal venous pressure
$P_c$=Central Venous pressure measured in the Right Atrium
$P_{ei}$=Effective Differential Intraventricular CSF Pressure (Pcsf−Pp)

The brain is suspended in CSF within the cranial cavity. CSF formed in the ventricles eventually flows through the subarachnoid space and drains into the venous sinuses, including the superior sagittal sinus (SSS). An increase in CSF pressure (Pcsf) over intraparenchymal venous pressure (Pp) tends to increase the size of the ventricles, whereas an increase in intraparenchymal venous pressure (Pp) over CSF pressure (Pcsf) tends to reduce ventricular size. The intracranial venous system is composed of intraparenchymal veins and capillaries, veins of the subarachnoid space and the venous sinuses. The venous capillaries collect fluid from the extracellular space and form larger and larger veins ultimately traversing the subarachnoid space. The veins of the subarachnoid space are characterized by relatively thin walls and the majority of these veins are submerged in CSF. Partly because of their thin, flexible walls, changes in CSF pressure in the subarachnoid space (Psa) are transmitted to the veins which in turn results in a change in the lumenal cross-sectional area of the veins (Hakim, 1985. *The physics and physicopathology of the hydraulic complex of the central nervous system*. PhD Thesis, Massachusetts Institute of Technology). The change in the cross-sectional area of the veins then results in changed resistance of the parenchymal venous circulation before draining into the venous sinuses. In summary, changes in subarachnoid CSF pressure (Psa) are transmitted to the parenchymal venous system. The difference between intraparenchymal venous pressure (Pp) and CSF pressure (Pcsf) must be maintained in order to protect the brain tissue from distortion or deformation. Hydrocephalus has therefore been described as the result of an increased pressure differential between CSF and the intracranial venous pressures (Hakim 1985). The brain is essentially subject to two opposing pressures: the intraparenchymal venous pressure (Pp) and the CSF pressure (Pcsf). Provided that there is no difference between these two pressures, and that condition remains constant, the brain is not subjected to stress or distortion.

In summary, where there is no gradient, e.g., when Pcsf=Pp, the ventricular size does not change. When the gradient is such that Pcsf>Pp, the ventricles increase in size. This happens in high pressure hydrocephalus where Pcsf increases due to an obstruction in the circulation of the fluid and Pp remains normal, (Pcsf>Pp). This also happens in NPH, in which Pcsf remains normal, but Pp decreases below normal also producing a gradient such that Pcsf>Pp.

NPH is usually treated by implanting a ventricular shunt that drains excess CSF from the ventricles. These shunts are generally comprised of a cerebral catheter inserted through the brain into the ventricle and a one-way valve system that drains fluid from the ventricle into a reservoir of the body, such as the jugular vein or the peritoneum (see, for example, U.S. Pat. No. 3,886,948). The shunt causes CSF to drain from the ventricles so long as the CSF pressure is greater than the operating pressure of the valve. Treatment of NPH using a ventricular shunt requires that the valve have a lower operating pressure than normal CSF pressure (Pcsf) so that the ventricle can decrease in size. Because the intraparenchymal venous pressure (Pp) cannot be lowered below the pressure of the Superior Saggital Sinus, the venous pressure remains unchanged by the shunt. As the CSF pressure is decreased by the shunt, eventually, the intraparenchymal venous pressure (Pp) becomes greater than the CSF pressure (Pcsf) and as a result, unless an adjustment is made, the ventricles will continue to decrease in size. Excess decrease in ventricular size is itself associated with several complications, including, for example, slit ventricles and subdural hematomas. Therefore, once the ventricles have reached a normal size, the CSF pressure (Pcsf) must be restored to a normal level. Implantation of a ventricular shunt can often be a successful treatment for NPH, however, there are situations where the ventricles do not return to normal size after shunt implantation. In addition, surgical implantation is itself associated with serious risks such as over and under-drainage as well as infection (Jones et al. (2008). Cerebrospinal Fluid Research 5: 19. Shprecheret al. (2009). Curr Neurol Neurosci Rep 8(5): 371-376). It would therefore be advantageous to develop improved methods of treating and diagnosing normal pressure hydrocephalus that can optionally be utilized in conjunction with current available treatments for NPH.

The present invention is based on the discovery that normal pressure hydrocephalus (NPH) is characterized by and at least partially caused by a decreased flexibility or compliance of the veins in the subarachnoid space. This discovery has led to a number of diagnostic and treatment methods for the disorders disclosed herein.

In some aspects, the present disclosure provides a method of treating normal pressure hydrocephalus, low pressure hydrocephalus (LPH), or very low pressure hydrocephalus (VLPH), comprising increasing intraparenchymal venous pressure from a sub-normally low value to a normal value or to a value higher than normal, without substantially altering, e.g., without substantially increasing cerebrospinal fluid (CSF) pressure.

In some embodiments, increasing intraparenchymal venous pressure comprises placing the patient in a hyperbaric chamber and venting the CSF (e.g., via a ventricular shunt or spinal tap) to an area with pressure lower than the hyperbaric chamber, e.g., to outside the hyperbaric chamber. In embodiments, the ventricular shunt comprises a ventricular catheter, a distal catheter, and an adjustable valve disposed between the ventricular catheter and the distal catheter. In embodiments, the ventricular shunt comprises a reservoir disposed between the adjustable valve and the ventricular catheter.

In some embodiments, increasing intraparenchymal venous pressure comprises placing a compression boot around the patient's legs and/or feet, optionally in combination with removing CSF from the patient, e.g., through a ventricular shunt or spinal tap.

In some embodiments, increasing intraparenchymal venous pressure comprises performing a compression of the jugular veins when the patient is lying at an incline of +35° or less, e.g., at an incline of +30°, +25°, +20°, +15°, or +10° or less, optionally in combination with removing CSF from the patient, e.g., through a ventricular shunt or spinal tap.

In embodiments, performing the ventricular shunt or spinal tap comprises removing about 10-100, 20-90, 30-80, 40-70, or 50-60 ml of CSF fluid from the patient, e.g., from the patient's brain.

In some embodiments, the sub-normally low value of intraparenchymal venous pressure is between 70 and 120 mm $H_2O$, e.g., 70-80, 80-90, 90-100, 100-110, or 110-120 mm $H_2O$. In some embodiments, the sub-normally low value of intraparenchymal venous pressure is 80-110 or 90-100 mm $H_2O$.

In some embodiments, the value higher than normal of intraparenchymal venous pressure is between 1-5, 1-10, 1-15, 1-20, 1-25, or 1-30, 1-50, 1-100, 1-150, or 1-200 mm $H_2O$ above normal intraparenchymal venous pressure. In some embodiments, the value higher than normal of intraparenchymal venous pressure is 120-125, 120-130, 120-135, 120-140, 120-145, 120-150, 120-170, 120-220, 120-270, or 120-320 mm $H_2O$. In some embodiments the intraparenchymal venous pressure is maintained at a value higher than normal for a period of at least 1, 1.5, 2, 3, 4, 6, 12, or 24 hours. In some embodiments the intraparenchymal venous pressure is maintained at a value higher than normal for a period of 1-2, 2-3, 3-4, 4-6, 6-12, or 12-24 hours. In some embodiments, the intraparenchymal venous pressure is maintained at a value higher than normal until the ventricles have decreased in size, e.g., reached a normal size and/or wherein one or more symptoms of NPH have been diminished or resolved.

In some embodiments, during treatments described herein, the pressure differential between intraparenchymal venous pressure and CSF pressure (e.g., the amount by which intraparenchymal venous pressure is greater than CSF pressure) is 10-200, 10-20, 20-50, 50-100, or 100-200 mm $H_2O$. In some embodiments, the amount by which intraparenchymal venous pressure is greater than CSF pressure is at least 10, 20, 50, 100, or 150 mm $H_2O$.

In some embodiments, the intraparenchymal venous pressure is increased while maintaining the CSF pressure close to its normal value, by implanting a shunt or by venting the CSF fluid to atmospheric pressure.

In some embodiments, the CSF pressure is approximately 120 mm $H_2O$, e.g., about 115-125, 110-130, or 105-135 mm $H_2O$. In some embodiments, the CSF pressure changes by less than 1, 2, 3, 4, 5, or 10 mm $H_2O$ during the method.

In some embodiments, the method comprises narrowing the difference between the CSF pressure and the intraparenchymal venous pressure, e.g., to less than 50, 40, 30, 20, 10, 5, 4, 3, 2, or 1 mm $H_2O$.

In some embodiments, the method comprises raising the intraparenchymal venous pressure to above the CSF pressure, e.g., to at least 1, 2, 3, 4, 5, 10, or 20 mm $H_2O$ above the CSF pressure.

In some embodiments, the method further comprises implanting an externally programmable valve into the brain of the patient such that CSF can exit the ventricles through the externally programmable valve.

In an embodiment, the method comprises evaluating the patient for a symptom or characteristic of NPH. The symptom or characteristic may be, e.g., ventricle size. In embodiments, e.g., responsive to the evaluation, a treatment regime is selected. The treatment regime can comprise ceasing treatment, continuing treatment, continuing treatment under different conditions, e.g., a different dosage, or adding or ceasing an adjunctive treatment modality, e.g., exposure to a hyperbaric environment. In some embodiments, the CSF is vented to outside the hyperbaric environment, e.g., by a ventricular catheter or spinal tap.

The present disclosure also provides a method of diagnosing a patient with normal pressure hydrocephalus comprising increasing intraparenchymal venous pressure in said patient and monitoring said patient for symptom improvement. In some embodiments, the intraparenchymal venous pressure is increased by introducing said patient to a hyperbaric environment for a time and under conditions suitable for increasing intraparenchymal venous pressure. In some embodiments, the CSF is vented to outside the hyperbaric environment, e.g., by a ventricular catheter or spinal tap.

In an embodiment, the patient is evaluated for the triad of symptoms: motor disturbances (e.g. gait impairment), incontinence, and dementia; these symptoms are often associated with ventricular enlargement in the absence of elevated intracranial pressure, and if a basis for diagnosing NPH (e.g., ventricles enlarged and gait impairment at unacceptable level) is seen, a shunt is implanted.

In an embodiment, intraventricular pressure can be decreased relative to, e.g., below, the intraparenchymal venous pressure by decreasing the CSF pressure and/or increasing the intraparenchymal venous pressure.

In an embodiment, the venous pressure of the brain is increased by providing the patient with a hyperbaric environment, wherein said hyperbaric environment has a pressure greater than atmospheric pressure, and simultaneously venting the CSF, e.g., from the ventricles, to the exterior of the hyperbaric environment.

In an embodiment, the intraventricular pressure or the CSF pressure can be decreased by use, e.g., the implantation of, a CSF shunt (e.g., a shunt comprising a valve) that drains CSF from the ventricles into another part of the body. In embodiments, it drains to where it can be absorbed by the circulation (such shunts are also referred to herein as ventricular shunts). CSF shunts include, for example, ventriculoperitoneal, ventriculopleural and ventriculoatrial shunts.

In an embodiment, the shunt comprises a cerebral catheter that passes through the brain into the ventricle and a one-way valve system that drains fluid from the ventricle into a reservoir of the body.

In an embodiment, the method comprises one or more or all of:
(i) after surgical implantation of the shunt, setting the pressure of the valve, e.g., setting the pressure of the valve equal to the patient's pre-surgery ventricular CSF pressure so that a pressure change does not occur immediately after surgery;
(ii) after the patient has recovered from the surgery, decreasing the pressure of the valve, e.g., in order to reduce the size of the ventricles; and
(iii) after the ventricles have reduced sufficiently, setting, e.g., increasing, the pressure of the valve sufficiently to prevent further shrinking of the ventricles.

In an embodiment, the valve is an externally programmable valve. In an embodiment, the externally programmable valve is a differential pressure valve, which can be adjusted non-invasively by the clinician, e.g., by using an externally applied rotating magnetic field. In an embodiment, the shunt is an externally programmable shunt, e.g., a Codman Hakim Programmable Valve (Codman, Raynham, MA) or a Medtronic Strata valve, or any other adjustable or non-adjustable valve.

In embodiments, the CSF pressure can be decreased by lumbar drainage.

In embodiments, the pressure of the hyperbaric chamber can be adjusted to a pressure sufficient to increase the venous pressure of the brain. In embodiments, the hyperbaric chamber has a pressure that is increased, for example, from about 250 to about 350 mm $H_2O$ above atmospheric pressure. In embodiments, the patient remains in the hyperbaric chamber for at least about 30 to about 60, 90, or 120 minutes. In certain embodiments, the gas flowing into the chamber is oxygen.

In embodiments, the venous pressure of the brain can also be increased using mechanical means.

In yet another aspect, the invention is directed to a method of treating a patient suffering from NPH comprising introducing said patient into a hyperbaric environment. In some aspects, of the invention, the method further comprises implanting into the brain of said patient a shunt that decreases CSF pressure into the brain of said patient prior to introducing the patient to a hyperbaric environment while simultaneously venting the CSF to the exterior of the hyperbaric environment.

In an embodiment, the patient has a ventricular catheter, e.g., a catheter vented to the exterior of the hyperbaric environment.

In an embodiment, the method includes implantation of a ventricular shunt, e.g., a shunt comprising a valve. It will be understood that the shunt can be implanted before or after the patient is introduced to the hyperbaric environment.

In an embodiment, the patient has had a shunt for at least 1, 2, 3, 7, 14, 21, or 28 days prior to being introduced into the hyperbaric environment.

In an embodiment, a patient having a shunt has been evaluated, e.g., by imaging of the brain, e.g., by MRI of the brain, for a symptom of NPH, e.g., enlarged ventricles. In embodiments, e.g., responsive to the evaluations, the patent is introduced into the hyperbaric environment.

In embodiments, the patient is kept in the hyperbaric environment for 0.5, 1, 1.5, 2, 3, 5, or 12 hours, e.g., at least 0.5, 1, or 1.5 hours, and in some embodiments not more than 1.5, 2, 3, or 5 hours. In embodiments, the patient is kept in the hyperbaric environment for 0.5-1.5, 0.5-2, 0.5-3, 0.5-5, 1-1.5, 1-2, 1-3, 1-5, 1.5-2, 1.5-3, or 1.5-5 hours.

In an embodiment, the patient is kept in a hyperbaric environment for at least 30, 60, 90, or 120 minutes/day for at least 1, 2, 3, 7, 14, 21, or 28 days. In an embodiment, the days are consecutive. In an embodiment, 1, 2, 3, 7, 14, 21, or 28 days, e.g., at least 1, 2, 3, or 7 but not more than 7, 14, 21, or 28 days without hyperbaric environment treatment can be interposed between days of treatment.

In embodiments, the patient is introduced into the hyperbaric environment for a time and under conditions suitable to decrease the size of the ventricles.

In an embodiment, after, or in response to an insufficient reduction in symptoms, e.g., an insufficient reduction in the size of ventricles, the patient is introduced into a hyperbaric environment. In some embodiments, the CSF is vented to outside the hyperbaric environment, e.g., by a ventricular catheter or spinal tap. In embodiments, this follows other treatment, e.g., the use of a shunt and/or a pharmacologic agent.

In an embodiment, the patients CSF pressure is reduced (e.g., via the ventricular catheter or spinal tap) and the venous pressure increased (e.g., via the hyperbaric environment). In some embodiments, the patient also has a ventricular shunt, e.g., a shunt comprising a valve.

In some aspects, the disclosure provides a method of treating a patient suffering from normal pressure hydrocephalus comprising increasing the intraparenchymal venous pressure in the patient.

In some aspects, the disclosure provides a method of decreasing ventricular size in a patient in need thereof comprising increasing the intraparenchymal venous pressure in the patient.

The disclosure contemplates all combinations of any one or more of the foregoing aspects and/or embodiments, as well as combinations with any one or more of the embodiments set forth in the detailed description and examples.

Headings, including numeric and alphabetical headings and subheadings, are for organized presentation and are not intended to be limiting. All references, publications, patent documents, mentioned herein are incorporated by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5A illustrates the normal brain, with normal size ventricles and normal subarachnoid veins. FIG. 5B illustrates a brain with Normal Pressure Hydrocephalus, in which the ventricles are enlarged and the Subarachnoid Veins are hardened.

FIG. 8A is a photograph of a cross-section of a normal brain with normal ventricles and FIG. 8B is a photograph of a hydrocephalic brain with enlarged ventricles.

In FIG. 11A, a tube that is flexible and responsive to compression is placed at the opening of a balloon filled with liquid. It is possible to maintain the internal pressure of the balloon by applying pressure to the flexible tube. In contrast, in FIG. 11B, a rigid tube is placed at the opening of a balloon filed with liquid. Because applying pressure on the tube does not result in compression, the interior pressure of the balloon is not maintained and the liquid flows out of the balloon. The flexible tube is analogous to a healthy vein or artery, whereas the rigid tube is analogous to a hardened vein or artery.

In FIG. 12A, the pressure of the liquid entering the chamber is able to influence the tube attached to the sponge and the sponge does not deform. In FIG. 12B, the pressure of the liquid entering the chamber is not able to transmit the increased pressure to the tube and the liquid in the sponge escapes and the sponge compresses.

FIG. 14A shows the chamber at atmospheric pressure and the ventricles in the brain of the patient are enlarged. In FIG. 14B, the pressure inside the chamber has been increased above atmospheric pressure (Hyperbaric chamber) and the ventricles have reduced in size because the intraparenchymal venous pressure was increased above the intraventricular CSF pressure.

FIG. 16A illustrates the cranial cavity with enlarged ventricles inside a hyperbaric chamber, with the pressure inside the chamber being atmospheric pressure. The CSF is vented outside the chamber. In FIG. 16B, the pressure inside the chamber is increased above atmospheric pressure. As the pressure in the chamber is increased above atmospheric pressure, the venous pressure will increase but not the CSF pressure, since it is vented outside the chamber to atmospheric pressure. This creates a gradient such that the venous pressure will be higher than the CSF pressure and the ventricles will reduce in size.

FIG. 35A depicts electron micrographs showing collagen fibers present in the veins affected by normal pressure hydrocephalus. FIG. 35B shows optical activity in veins in a region where hydrocephalus developed, and an absence of optical activity in an unaffected region. FIG. 35C shows veins from a normal brain and from a brain with high pressure hydrocephalus, as seen under normal light and under polarized light. FIG. 35D shows optical activity on the veins from two brains with NPH.

DETAILED DESCRIPTION OF THE INVENTION

Figure 1:
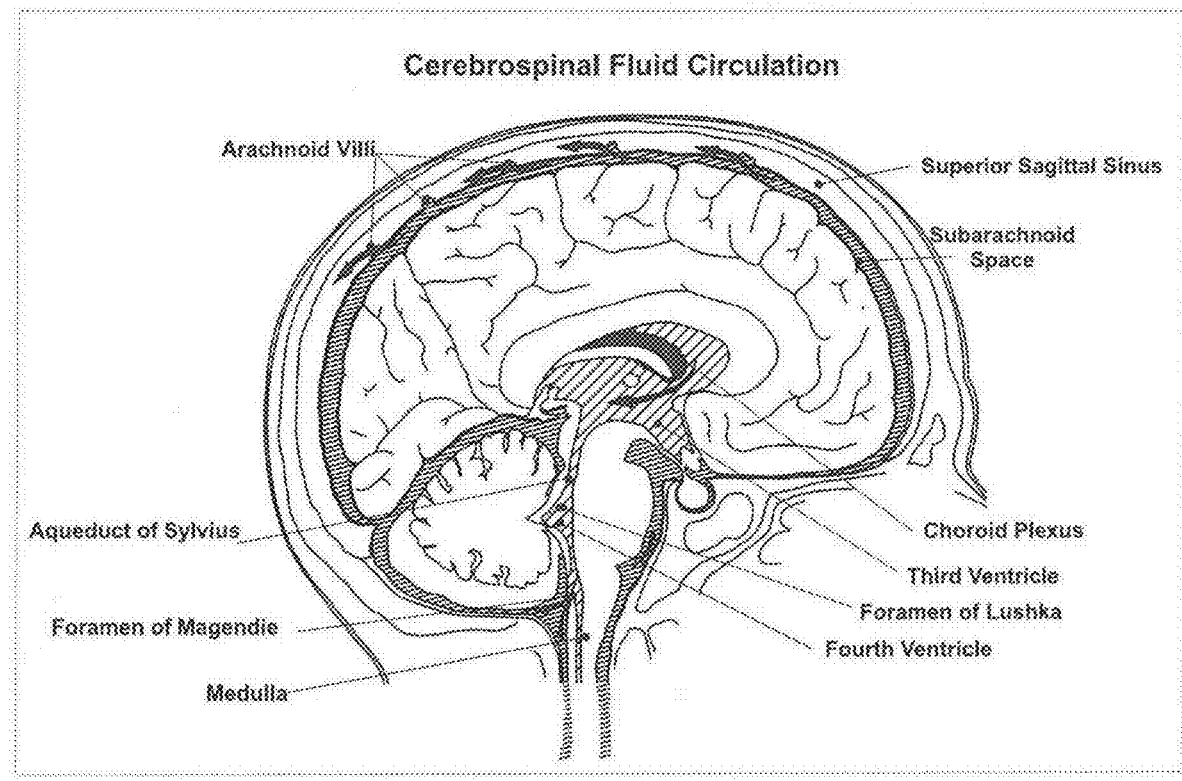
FIG. 1 is a drawing showing a sagittal cross-section of the human head, CSF circulation, and various anatomical structures including the sagittal sinus, the arachnoid villi, the subarachnoid space, the medulla, the Foramen of Magendie, the cerebral aqueduct, the choroid plexus, the third and fourth ventricles, and the Foramen of Lushka.

A description of preferred embodiments of the invention follows.

NPH, CSF Pressure, and Intraparenchymal Venous Pressure

As discussed above, the methods of treatment and diagnosis herein are based at least in part on the discovery that NPH is at least partially caused by an imbalance between CSF pressure (Pcsf) and the intraparenchymal venous pressure (Pp). High pressure hydrocephalus is normally produced by an obstruction in the pathways of the CSF which leads to an increase in CSF pressure. This increase in CSF pressure makes the CSF pressure greater than the intraparenchymal venous pressure resulting in an enlargement of the ventricles and an abnormal accumulation of CSF or hydrocephalus. In contrast, NPH is produced by a decrease in the intraparenchymal venous pressure (while CSF pressure remains normal), which also results in an enlargement of the ventricles and an accumulation of CSF, or hydrocephalus. It has been discovered that in the pathology samples of brains from patients with NPH, the blood vessels in the subarachnoid space of the brain exhibit a marked increase in the formation/accumulation of collagen in the adventitia or external layer of the blood vessels. It is believed that when the walls of the veins become hardened by collagen formation on their exterior, the CSF pressure can no longer be transmitted through the walls of the veins. Thus, the intraparenchymal venous pressure decreases in value below the pressure of the CSF, resulting in a pressure gradient such that the CSF pressure will be greater than the intraparenchymal venous pressure. This results in an increase in ventricular size (hydrocephalus) and the accumulation of CSF, which characterizes NPH.

The Brain: Material and Structure; Reaction to Pressures and Liquid Flow

To appropriately understand the brain, as well as many of its disease processes, it should be studied and understood, from a mechanical point of view, as material and structure. This approach is important to the characterization of the brain within the cranial cavity, in its normal and pathological physio-anatomical states.

The brain as material, while a biological tissue composed of neurons and glial cells, behaves as a visco-elasto-plastic solid (much more plastic than elastic). It can only absorb and tolerate for a short time the expansive force of the CSF pressure acting upon the ventricular walls. A living tissue, it senses any stress and yields rapidly in order to dissipate and relieve these stresses.

The brain, as a structure, is a submicroscopic open-cell sponge made of visco-elasto-plastic material. Its potential for volumetric change, "the give," arises from several factors. For example, "give" resides in the parenchymal extracellular fluid, probably lipids and proteins contained within the cells, and the intraparenchymal venous system. The "give" is regulated via the intraparenchymal venous system, which drains into the SSS (extraparenchymal venous system), which being open to atmosphere, permits fluid transfers from the parenchymal sponge. Based on the experiments described herein regarding patients with an open bone cranial defect, the intraparenchymal venous system seems to be the largest contributor to the volumetric changes.

The compressibility of the brain parenchyma as it occurs within the cranial cavity must be understood more as a structure (sponge) and less as a tissue (material). This distinction is of great significance especially in the presence of the very small pressures involved. A piece of brain, separated from its natural environment and hydraulic connections, loses its characteristics as a sponge, and if treated as a constrained volume becomes an almost incompressible material, with a very high bulk modulus. The observed changes and reversals in ventricular size discussed herein develop in a matter of hours only because the sponge-like parenchyma can be compressed and refilled via the small pressure changes encountered in the fluids of the cranial cavity.

Figure 2A:
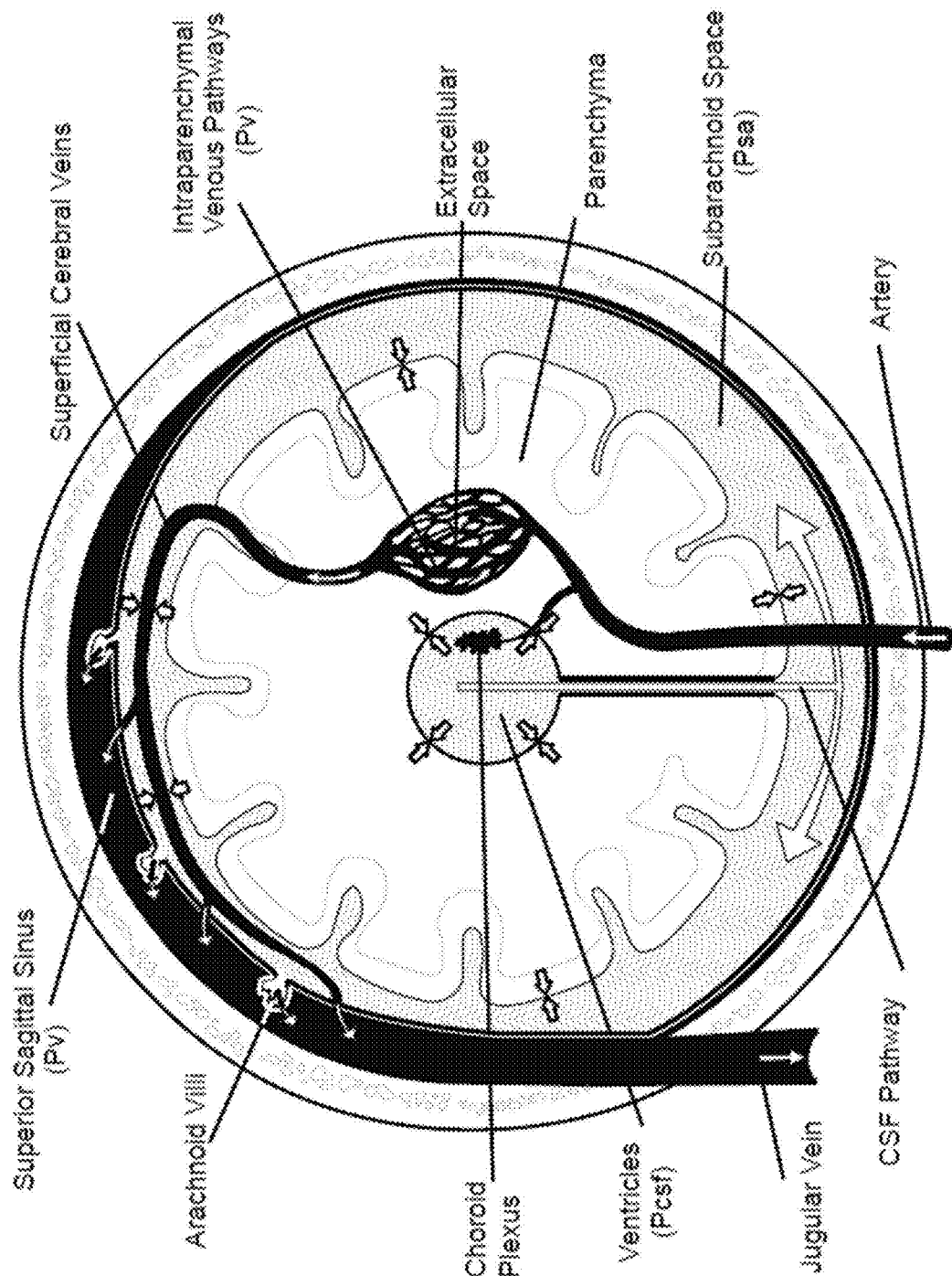
FIG. 2A is a drawing depicting a coronal cross-section of the cranial cavity and showing the pathway of the CSF from the ventricles into the Subarachnoid Space and finally draining into the SSS. Also illustrated is the pathway of the Intraparenchymal Venous Blood through the Superficial Cerebral Veins into the SSS.
Figure 2B:
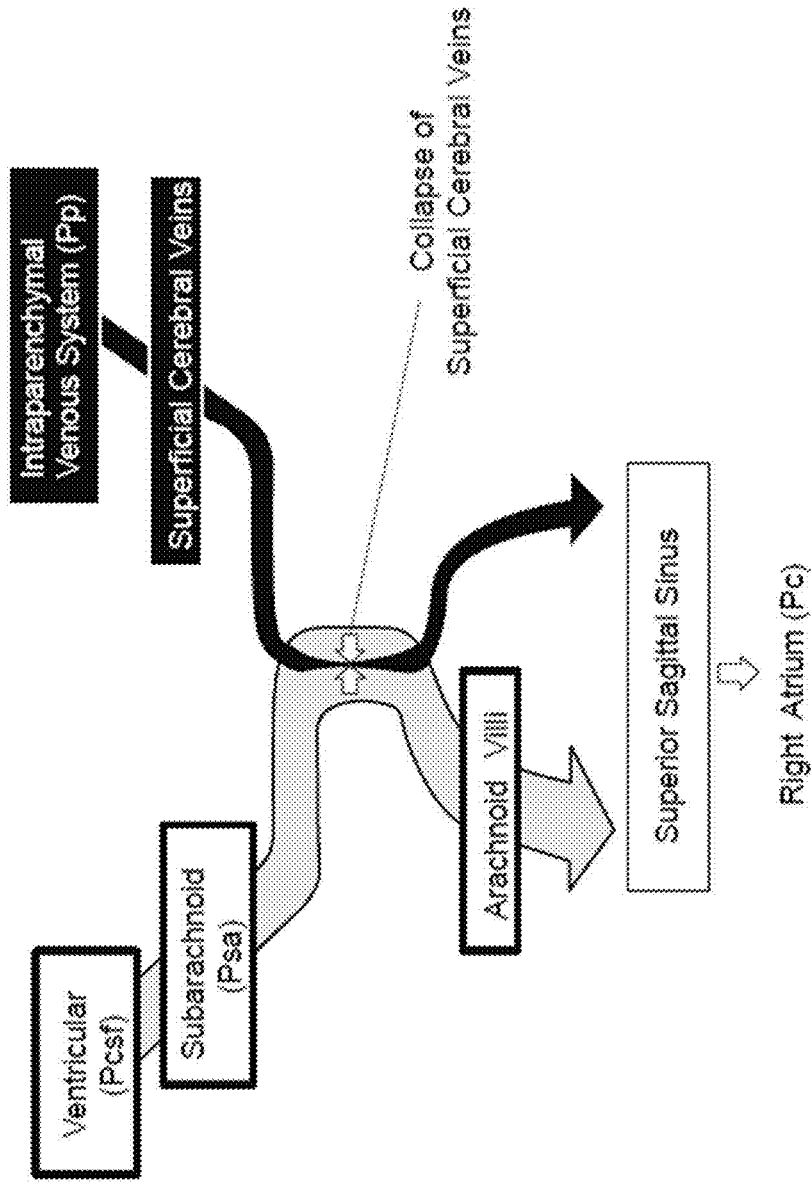
FIG. 2B is a schematic representation of the hydraulic mechanisms which keep the Ventricular Cerebrospinal Fluid Pressure (Pcsf) equal to the Intraparenchymal Venous Blood Pressure (Pp) and maintain the brain tissue under a dynamic equilibrium condition.
Figure 3:
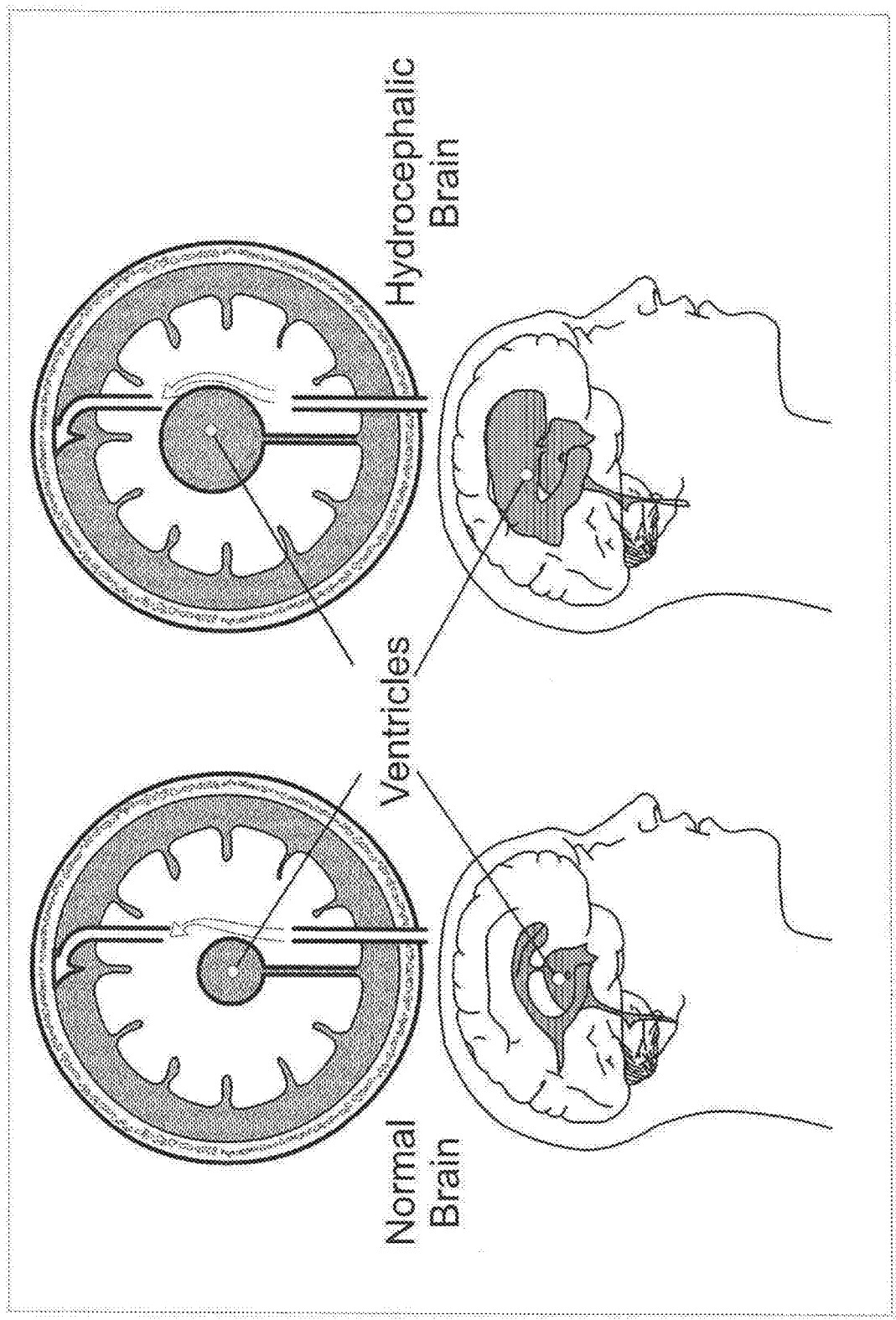
FIG. 3 is a drawing comparing the size of the ventricles in a normal brain and in a hydrocephalic brain.
Figure 4:
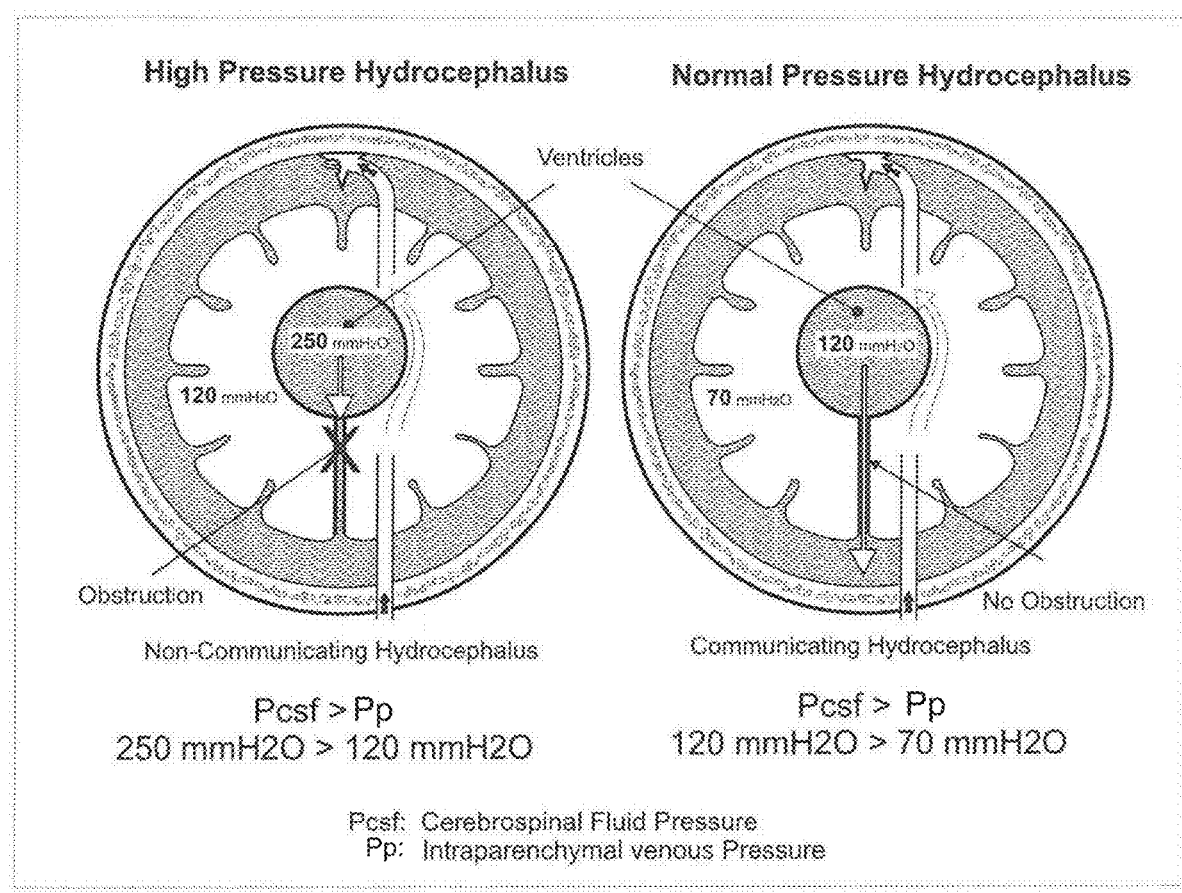
FIG. 4 is a drawing contrasting the pressures of the CSF in the ventricles and of the intraparenchymal veins of patients with high pressure hydrocephalus and patients with normal pressure hydrocephalus. Notice that in both types of hydrocephalus, the CSF Pressure is higher than the intraparenchymal venous pressure. In the case of High Pressure Hydrocephalus, Pcsf is high while Pp is normal. In the case of Normal Pressure Hydrocephalus, Pcsf is normal while Pp is below normal.
Figure 5A:
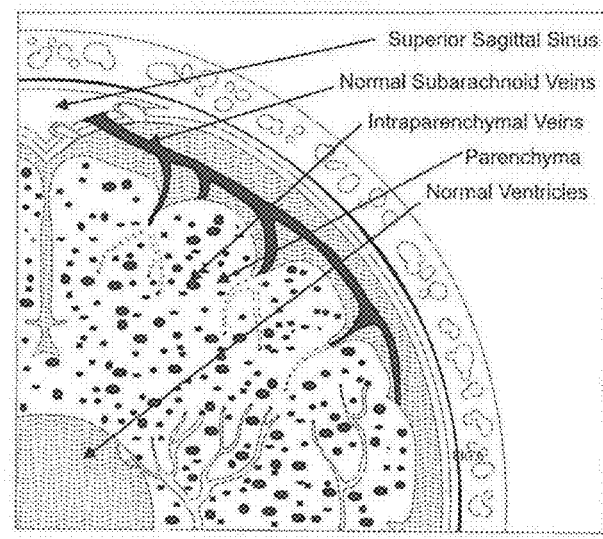
FIGS. 5A and 5B are drawings showing several anatomical structures in the brain including subarachnoid veins, intraparenchymal veins, sagittal sinus, parenchyma and ventricles.
Figure 5B:
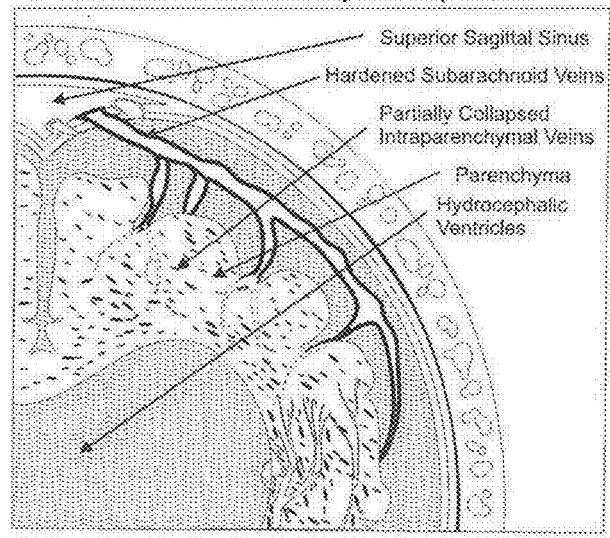

The veins emerging from the brain surface travel through the subarachnoid space, submerged in CSF, to join the dural venous sinuses and drain into the SSS, see, e.g., FIG. 2A. The normal pressure in the SSS in a horizontal position is approximately 70 mm $H_2O$ ($P_v$, =Extraparenchymal venous pressure, measured in the SSS). Therefore, this would also be the pressure of the subarachnoid veins and of the brain parenchyma if these veins were either not surrounded by CSF or if they were rigid tubes.

The CSF also drains into the SSS, but through a different pathway, the arachnoid villi. The resistance through these villi is greater than the pressure of the SSS. Therefore, the normal pressure of the CSF in the subarachnoid space ($P_{sa}$=Subarachnoid CSF pressure) is approximately 120 mm $H_2O$ in a horizontal position. Since the subarachnoid veins have very thin and flexible walls, the CSF surrounding them will flatten the veins and increase their resistance until the internal pressure of the veins is equal to that of the CSF surrounding them (see Example 8). Any variation of the CSF pressure in the subarachnoid space is immediately transmitted to these veins, either decreasing or increasing their luminal cross-sectional area, changing the resistance of the parenchymal venous outflow before draining into the SSS. Therefore, subarachnoid CSF pressure induces parallel variations in the intraparenchymal venous system pressure. Likewise, a venous pressure variation at the level of the SSS or thereafter is transmitted to both intraparenchymal venous and CSF systems equally, because both drain into the SSS. This venous pressure variation can be caused by, e.g., a normal subject changing from a prone to upright posture or vice versa. When the subject changes positions, the SSS changes pressure, and this change is communicated to both the parenchymal veins and the CSF. These two systems then remain in equilibrium with no gradient, even though their absolute values may rise or fall. In conclusion, these two mechanisms assure a constant hydrostatic loading of the brain tissue or sponge-like parenchyma.

The brain tissue or parenchyma is subjected to two opposing pressures. One is produced by the CSF system, which tends to enlarge the ventricles, and the other is produced by the intraparenchymal venous system, which tends to reduce the ventricles. As long as these two pressures remain equal regardless of their absolute values, the tissue is not submitted to the slightest degree of stress or distortion, and the ventricular size remains unchanged in a steady state condition.

The gradient which controls the degree to which liquids may be squeezed out or into the parenchymal sponge, and in consequence change and control ventricular size, is the differential existing between the intraventricular CSF pressure ($P_{csf}$) and the intraparenchymal venous pressure ($P_p$). This gradient is designated the effective differential intraventricular CSF pressure ($P_{ei}=P_{csf}-P_p$). When $P_{csf}>P_p$, $P_{ei}>0$ and the fluid is squeezed out of the parenchyma; when $P_{csf}<P_p$, $P_{ei}<0$ and the fluid is squeezed into the parenchyma.

Depending on the hardening of the walls of the veins in NPH, the CSF will not be able to flatten them as much and their internal pressure will drop as low as the pressure of the SSS.

For hydrocephalus to occur, the effective differential intraventricular CSF pressure ($P_{ei}$) must increase. This can be accomplished by either increasing intraventricular CSF pressure ($P_{csf}$) above $P_p$, or by decreasing intraparenchymal venous pressure ($P_p$) below $P_{csf}$, since $P_{ei}=P_{csf}-P_p$. An increase in $P_{ei}$ produces an increase in the tangential and radial stresses of the parenchyma, pushing the ventricular wall towards the periphery of the brain. If $P_{ei}$ thereafter returns to its normal value (therefore $P_{csf}=P_p$), the parenchymal tissue will have yielded bioplastically and will remain in this new steady state condition of permanent set with dilated ventricles, having reached the mechanics of NPH.

The present invention is also based on the discovery that normal pressure hydrocephalus (NPH) is characterized by decreased flexibility or compliance of veins in the subarachnoid space (also referred to herein as subarachnoid veins). This decreased flexibility of the subarachnoid veins means that changes in CSF pressure are not transmitted to the veins and the lumenal cross-sectional area of the veins does not change in response to CSF pressure.

As discussed above, in the normal brain, changes in CSF pressure in the subarachnoid space essentially compress the veins, which in turn results in a change in the lumenal cross-sectional area of the veins. Because the veins in the subarachnoid space are thin-walled and flexible, the veins are able to respond to an increase in CSF pressure by decreasing their lumenal cross-sectional area. Thus, the pressure difference between CSF pressure and venous pressure remains in equilibrium and the ventricles remain in their normal state. In contrast, in the brain of a patient with NPH, the walls of the veins are characterized by decreased flexibility. In NPH, because the pressure of the venous system does not increase in response to an increase in CSF pressure, the differential between the CSF pressure and venous pressure increases and the ventricles increase in size.

In addition, it is believed that the accumulation of collagen on the arteries is another contributing factor in NPH. For example, we have observed that the arteries in the subarachnoid space in patients with NPH have an accumulation of collagen in the adventitia.

Low Pressure Hydrocephalus and Very Low Pressure Hydrocephalus

While many of the methods herein are described with reference to NPH, it is understood that the methods herein can also be applied to related diseases including low pressure hydrocephalus (LPH) and very low pressure hydrocephalus (VLPH). VLPH is characterized by enlarged ventricles with lower than normal CSF pressure in the ventricles. VLPH is described, e.g., in Noda et al., "Very Low-Pressure Hydrocephalus: A New Clinical Entity and Issues of Treatment" Showa Univ J Med Sci 23(2), 109-114 Jun. 2011.

Definitions

As used herein, the words "a" or "an" are meant to encompass one or more, unless otherwise specified.

"Acquire" or "acquiring" as the terms are used herein, refer to obtaining possession of a physical entity (e.g., a sample), or a value, e.g., a numerical value, or image, by "directly acquiring" or "indirectly acquiring" the physical entity or value. "Directly acquiring" means performing a process (e.g., performing a synthetic or analytical method, contacting a sample with a detection reagent, or capturing a signal from a sample) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance. Exemplary changes include making a physical entity from two or more starting materials, shearing or fragmenting a substance, separating or purifying a substance, combining two or more separate entities into a mixture, or performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; inducing or collecting a signal, e.g., a light based signal, e.g., a fluorescent signal, or by changing the structure of a reagent, or a fragment or other derivative thereof, e.g., by breaking or forming a covalent or non-covalent bond, between a first and a second atom of the reagent. Directly acquiring a value includes methods in which a computer or detection device, e.g., a scanner is used, e.g., when a change in electronic state responsive to impingement of a photon on a detector. Directly acquiring a value includes capturing a signal from a sample.

A "patient" is a human subject in need of treatment.

As used herein, the term "inhibiting" or "decreasing" or "reducing" encompasses causing a net decrease by either direct or indirect means. The term "increasing" or "raising" means to cause a net gain by either direct or indirect means.

The term "agent" is used herein to denote a chemical compound, a mixture of chemical compounds, a biological macromolecule (including, for example, a nucleic acid, an antibody, a protein or portion thereof, e.g., a peptide), a naturally occurring chemical compound or biologic macromolecule, or an extract made from biological materials such as bacteria, plants, fungi, or animal (particularly mammalian) cells or tissues.

"Treating" or "treatment" includes the administration of the compositions, compounds or agents described herein to prevent or delay the onset of the symptoms, complications, or biochemical indicia of a disease, alleviating or ameliorating the symptoms or arresting or inhibiting further development of the disease, condition, or disorder.

A "therapeutically effective amount" or an "effective amount" is an amount which, alone or in combination with one or more other active agents, can control, decrease, inhibit, ameliorate, prevent or otherwise affect one or more symptoms of a disease or condition to be treated and/or achieves a specifically recited objective.

Methods of Increasing Intraparenchymal Venous Pressure without Substantially Altering CSF Pressure There are numerous ways to increase intraparenchymal venous pressure in a patient. First, for example, increasing intraparenchymal venous pressure can comprise placing the patient in a compression boot, a device that fits over the feet and/or legs and applies pressure. Second, increasing intraparenchymal venous pressure can comprise performing compression of the neck, e.g., Queckenstedt's compression method. Third, increasing intraparenchymal venous pressure can comprise placing the patient in a hyperbaric chamber and venting the CSF to an area with pressure lower than the hyperbaric chamber, e.g., to outside the hyperbaric chamber. The venting can involve inserting a shunt into the patient's CSF, e.g., into the ventricles, and having the tube run outside the hyperbaric chamber. These methods may be performed in conjunction with use of a shunt or valve to drain CSF from the ventricles or spine into another part of the body or outside the body.

More specifically, a compression boot, or similar device, can be used to increase intraparenchymal venous pressure in a patient. In some embodiments, a compression boot, elastic bandages, or medical anti-shock trousers (MAST) are wrapped tightly around the patient's legs. In conjunction, the method can include lowering CSF pressure slightly or preventing CSF pressure from rising significantly, e.g., by performing a lumbar tap using a ventricular shunt or valve. In embodiments, about 10-100, 20-90, 30-80, 40-70, or 50-60 ml of fluid is withdrawn in a lumbar puncture. In some embodiments, CSF is removed from the subject's body, e.g., via a spinal tap.

Queckenstedt's compression method can be performed by placing a subject at an incline, e.g., having the subject lie horizontally or be at an incline of about +10° to +35°. Without being bound by theory, at an incline of about +35° or less, the jugular veins are typically substantially open such that most of the venous return occurs through the jugular veins; at higher inclines the jugular veins can be partially collapsed. Pressure is then applied to the neck of the subject to compress the external jugular veins. See, e.g., Hakim, 1985. *The physics and physiopathology of the hydraulic complex of the central nervous system*. PhD Thesis, Massachusetts Institute of Technology. Without wishing to be bound by theory, compression of the jugular veins causes venous return to instead occur through the vertebral veins; thus, Queckenstedt's compression method can increase the resistance of venous blood returning to the heart, thereby increasing the venous pressure in the brain. In conjunction, the method can include lowering CSF pressure slightly or preventing CSF pressure from rising significantly, e.g., by performing a lumbar tap or by using a ventricular shunt or valve. In some embodiments, CSF is removed from the subject's body, e.g., via a lumbar tap. In some embodiments, CSF is removed from the subject's brain, e.g., into another part of the body, e.g., into the right atrium or peritoneal cavity, e.g., via a shunt.

One way to vent the CSF to an environment of lower pressure is to vent the CSF to outside the hyperbaric environment, e.g., by a ventricular catheter or spinal tap. In an embodiment, the CSF is vented to the exterior of the hyperbaric chamber using a catheter that vents the CSF at the spine (e.g., a spinal tap) to the outside of the chamber. The environment of lower pressure can be at atmospheric pressure, less than atmospheric pressure (e.g., a hypobaric chamber), or pressure that is greater than atmospheric but lower than that in the hyperbaric chamber (e.g., a solution raised a specified amount above the patient). The area outside the hyperbaric environment may be, e.g., outside the hyperbaric chamber, or may be a lower-pressure area (e.g., a sub-chamber) within the hyperbaric chamber.

In embodiments, as is discussed in more detail below, the method comprises the use of a shunt, or other device, that decreases the CSF pressure, e.g., relative to the intraparenchymal venous pressure, in the brain of the patient; and/or administration of an additional, or adjunctive, treatment that increases intraparenchymal venous pressure, e.g., relative to the CSF pressure, e.g., by providing the patient with a hyperbaric environment, e.g., a hyperbaric chamber, while simultaneously venting the CSF to the exterior of the hyperbaric environment, for example, by venting CSF from the ventricles. In some embodiments, the use of the shunt comprises implanting the shunt or adjusting the shunt.

In one aspect of the invention, implanting a shunt into the brain of the patient decreases the CSF pressure. The shunt may comprise a ventricular catheter, which is in contact with CSF in the ventricle, and a distal catheter, which is in contact with another area of the body. The shunt may comprise a valve, e.g., and adjustable valve, disposed between the ventricular catheter and the distal catheter. Optionally, the shunt comprises a reservoir on the ventricular side of the valve. In some embodiments, the shunt is adapted to allow the ventricular catheter to be connected to an area of defined pressure, e.g., outside a hyperbaric environment.

In embodiments, the method further comprises decreasing the intraventricular pressure. In embodiments, after the ventricles become normal size, the pressure of the cerebrospinal fluid is equilibrated with the venous pressure.

As described above, the intraventricular pressure or the CSF pressure can be decreased by implantation of a shunt that drains CSF from the ventricles into another part of the body where it can be absorbed by the circulation (such shunts are also referred to herein as ventricular shunts). CSF shunts include, for example, ventriculoperitoneal, ventriculopleural and ventriculoatrial shunts. Non-limiting examples of such shunts are described, for example, in U.S. Pat. Nos. 3,288,142, 3,516,410, 3,527,226, 3,877,137, 3,886,948, 3,889,687, 3,958,562, 4,106,510, 4,312,293, 4,332,255, 4,387,715, 4,551,128, 4,595,390, 4,608,992, 4,615,691, 4,772,257, 5,928,182 and in Pujari et al. (2008), J Neurol Neurosurg Psychiatry 79: 1282-1268 and Vaneste et al. (1992), Neurology 42(1): 54-9, the contents of each of which are expressly incorporated by reference herein. These shunts are usually comprised of a cerebral catheter inserted through the brain into the ventricle and a one-way valve system that drains fluid from the ventricle into a reservoir of the body. After surgical implantation of the shunt, the pressure of the valve is set equal to the patient's pre-surgery ventricular CSF pressure so that a pressure change does not occur immediately after surgery. Once the patient has recovered from the surgery, the pressure of the valve is decreased in order to reduce the size of the ventricles. Once the ventricles have reduced sufficiently, the pressure of the valve is then increased to prevent further shrinking of the ventricles. Because patients often require several pressure adjustments after implantation of the shunt, externally programmable valves are commonly utilized. One such example of an externally programmable valve is a differential pressure valve which can be adjusted non-invasively by the clinician using an externally applied rotating magnetic field. Several externally programmable shunts are commercially available and include, for example, the Codman Hakim Programmable Valves (Codman, Raynham, MA) and Medtronic Strata valves.

In another example, the CSF pressure can be decreased by lumbar drainage.

As described above, for the treatment of NPH, the intraventricular pressure can be reduced relative to the intraparenchymal venous pressure of the brain by increasing the venous pressure of the brain. In one aspect of the invention, the intraparenchymal venous pressure of the brain can be increased by introducing the patient to a hyperbaric environment while concomitantly equilibrating the CSF pressure with atmospheric pressure or while venting the CSF from the ventricles to the exterior of the hyperbaric environment as described above. The patient's CSF pressure can be equilibrated with atmospheric pressure, for example, by lumbar puncture wherein the spinal needle is open to atmospheric pressure, for example, by means of a tube or catheter vented to an environment of atmospheric pressure. As used herein, a hyperbaric environment is an environment that has a pressure greater than atmospheric pressure. An example of a hyperbaric environment is a hyperbaric chamber. A hyperbaric chamber is a sealed chamber or compartment in which one or more individuals can enter. The use of hyperbaric chambers has been described for the treatment of decompression sickness, carbon monoxide poisoning, and wound healing. In one aspect of the invention, the hyperbaric chamber is a monoplace hyperbaric chamber. The pressure of the hyperbaric chamber can be adjusted to a pressure sufficient to increase the venous pressure of the brain. In some aspects, the hyperbaric chamber has a pressure that is increased, for example, from about 250 to about 350 mm $H_2O$ above atmospheric pressure. The patient can remain in the hyperbaric chamber for at least about 30 to about 60, 90, or 120 minutes. In certain embodiments, the gas flowing into the chamber is oxygen.

Venous pressure of the brain can also be increased using mechanical means.

The invention is also directed to a method of treating a patient suffering from normal pressure hydrocephalus comprising introducing said patient to a hyperbaric environment. In some embodiments, the CSF is vented to outside the hyperbaric environment, e.g., by a ventricular catheter or spinal tap. The introduction of the patient into a hyperbaric environment can also be conducted in combination with implantation of a ventricular shunt, wherein the ventricular shunt is capable of venting to an area of lower pressure, e.g., to outside the hyperbaric environment. It will be understood that the shunt can be implanted before or after the patient is introduced to the hyperbaric environment. In certain aspects of the invention, the patient is implanted with a ventricular shunt and some time after implantation of the shunt, the patient is introduced into the hyperbaric environment, and the shunt is vented to an area of lower pressure, for a time and under conditions suitable to decrease the size of the ventricles. This method can be especially useful in the case where a patient's ventricles do not sufficiently reduce in size after initial implantation of the shunt. Such patients may benefit from combined treatment of CSF pressure reduction (via the ventricular shunt), venous pressure increase (via the hyperbaric environment), and avoiding an increase in CSF pressure (by venting CSF to outside the hyperbaric environment).

In embodiments, the methods of treatment described herein (e.g., methods that comprise increasing the intraparenchymal venous pressure) comprise administration of a pharmacologic agent that increases the intraparenchymal venous pressure, e.g., that increases the flexibility of the subarachnoid veins and/or arteries, e.g., for the treatment of NPH. In certain aspects of the invention, an effective amount of a pharmacologic agent that increases the flexibility of the subarachnoid veins is administered to a patient suffering from NPH. In yet additional aspects of the invention, an effective amount of a pharmacologic agent that increases the flexibility of the subarachnoid arteries is administered to a patient suffering from NPH. In an embodiment, administration of a pharmacologic agent reduces the fibrosis of the subarachnoid veins. In an embodiment, administration of a pharmacologic agent reduces stiffening of the veins. In some embodiments, the agent increases the flexibility of the subarachnoid veins. In additional embodiment, the agent increases the flexibility of the subarachnoid arteries. In yet other embodiments, the agent increases the flexibility of the subarachnoid veins and/or arteries. The flexibility of the subarachnoid veins and/or arteries is increased after administration of a pharmacologic agent when the vein and/or artery has greater flexibility than that before administration of the agent to the patient. In some aspects, the flexibility of the veins and/or arteries is increased when there is change in the luminal cross-sectional of the veins and/or arteries in response to CSF pressure compared to the change in the luminal cross-sectional area in response to the same CSF pressure before administration of the pharmacologic agent. In an embodiment, administration of a pharmacologic agent increases the ability of the subarachnoid veins to change in the luminal cross-sectional in response to CSF pressure, e.g., as compared to the change in the luminal cross-sectional area in response to the same CSF pressure before administration of the pharmacologic agent. The agents that increase the flexibility of the subarachnoid veins and/or arteries can be tested in a number of animal models of disease. For example, a dog model for NPH is described in Examples 4 and 5.

In certain aspects of the invention, the pharmacologic agent is an anti-fibrotic agent. Anti-fibrotic agents include, for example, aprotinin, aprotinin derivatives, C1-esterase inhibitors, ε-amino-n-caproic acid (EACA), α-2-macroglobulin, α-2-plasmin inhibitor, α-1-plasmin inhibitor, plasminogen activator inhibitor, inhibitor or inactivator of activated protein C, a plasmin-binding substance, tranexamic acid, cis-hydroxyproline (cHYP), interferon, hepatocyte growth factor, TGFβ1 inhibitors, TGFβ2 inhibitors and PDGF inhibitors. Inhibitors of TGFβ1, TGFβ2 and PDGF include, for example, antibodies, soluble proteins, binding proteins that directly or indirectly inhibit the binding of these proteins to their receptors by binding to the growth factor itself, antisense oligonucleotides, RNAi or ribozymes, which act to inhibit the expression of these proteins.

Figure 9A:
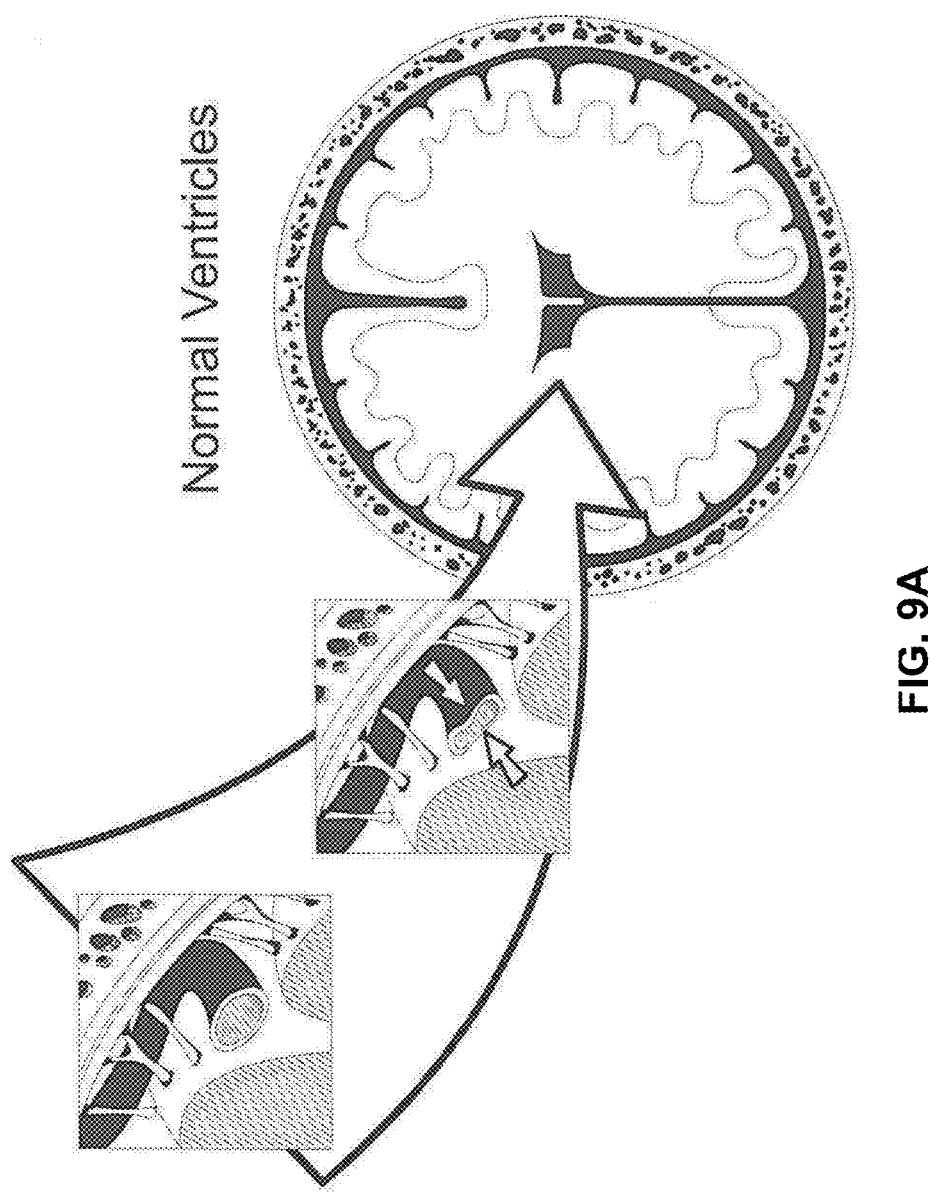
FIG. 9A is a series of drawings showing the normal state of subarachnoid veins: i) in the normal state, the veins are flexible and thin-walled, ii) the circulation of CSF is normal, iii) the veins respond to the pressure of the CSF by collapsing, iv) the pressure of the CSF and the parenchymal venous pressure are at equilibrium and v) the ventricles remain at normal size.
Figure 9B:
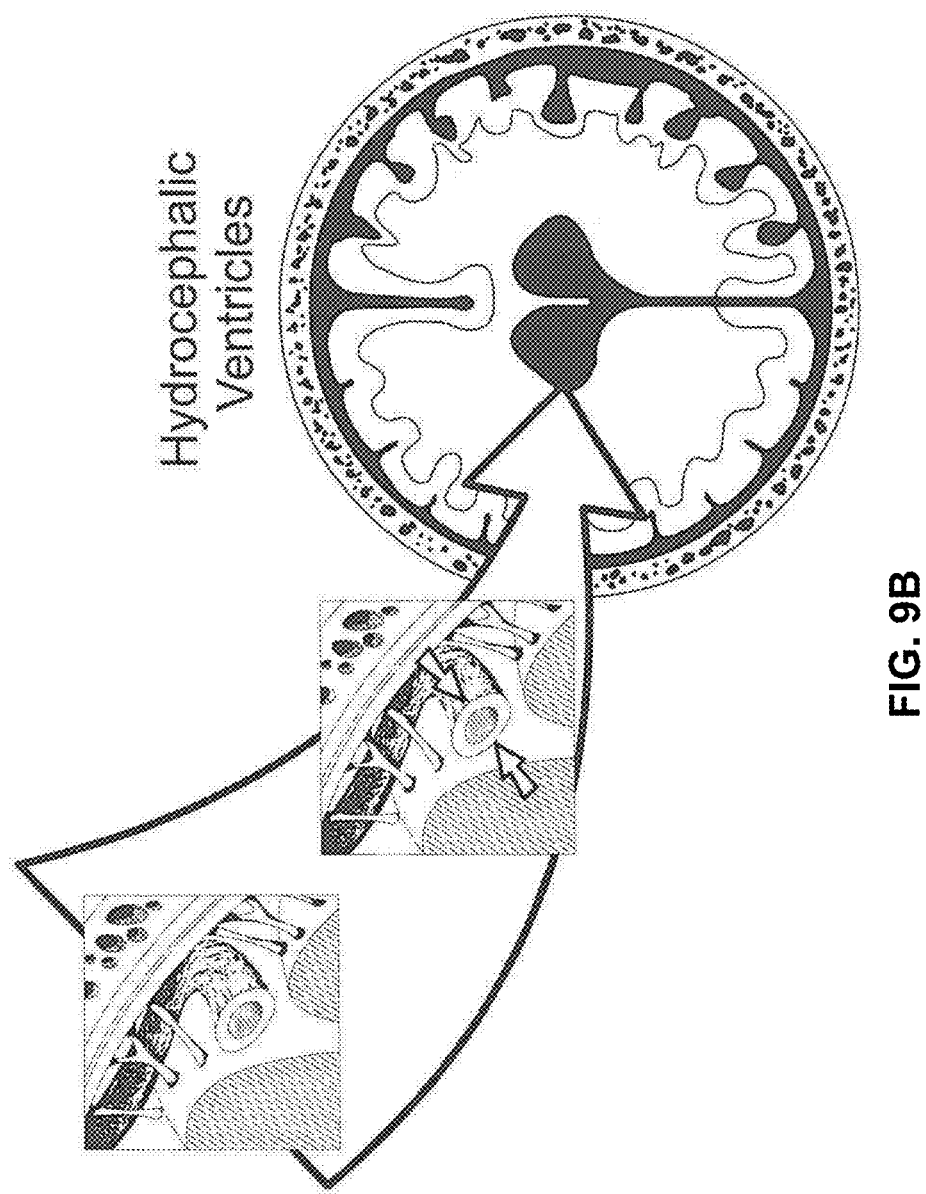
FIG. 9B is a series of drawings showing the state of veins in the brain of a patient with NPH: i) the veins have lost their flexibility and have stiffened walls, ii) the circulation of the CSF remains normal, iii) the veins are unable to collapse in response to pressure of the CSF, iv) the parenchymal venous pressure becomes lower than the pressure of the CSF, and v) the ventricles increase in size.
Figure 10:
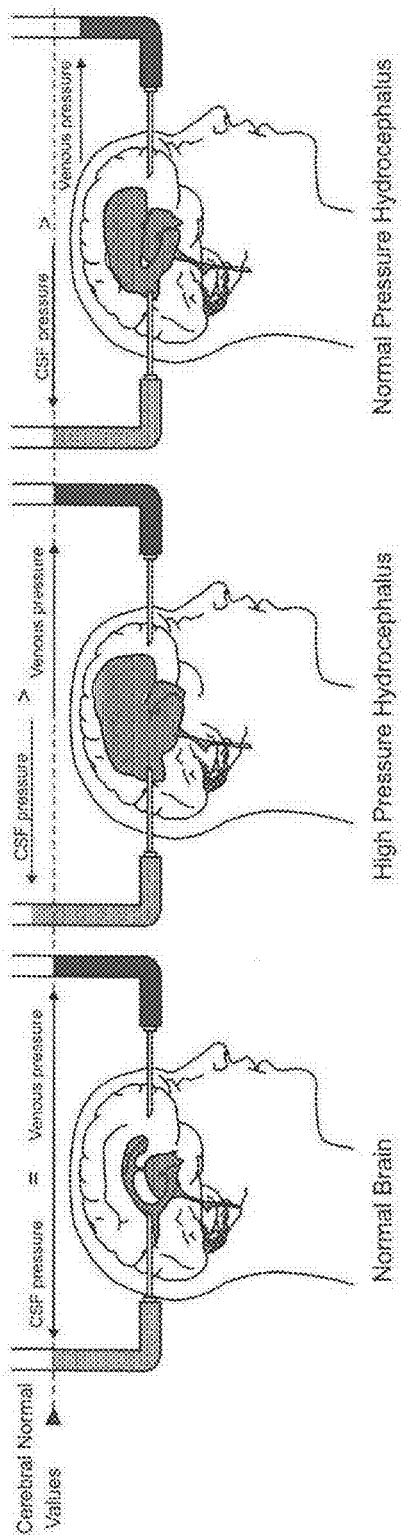
FIG. 10 illustrates three different states of the brain. In the normal brain, the CSF Pressure and the Intraparenchymal Venous Pressure are equal. In the brain with High Pressure Hydrocephalus, the ventricles are enlarged, the CSF pressure is increased and the intraparenchymal venous pressure is normal. In the brain with Normal Pressure Hydrocephalus, the ventricles are enlarged, the CSF pressure is normal and the intraparenchymal venous pressure is below normal.
Figure 11A:
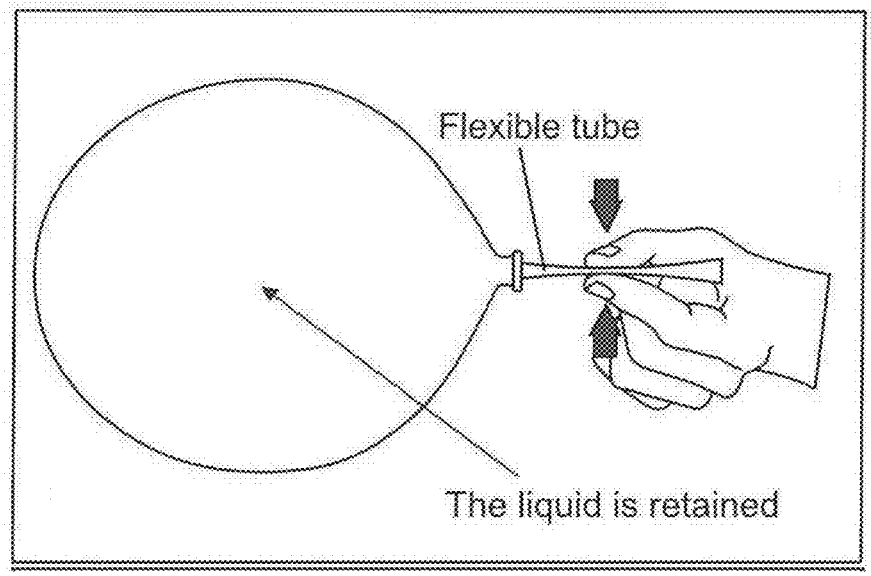
FIGS. 11A and 11B are drawings of a simple model demonstrating the importance of flexibility in the subarachnoid veins.
Figure 11B:
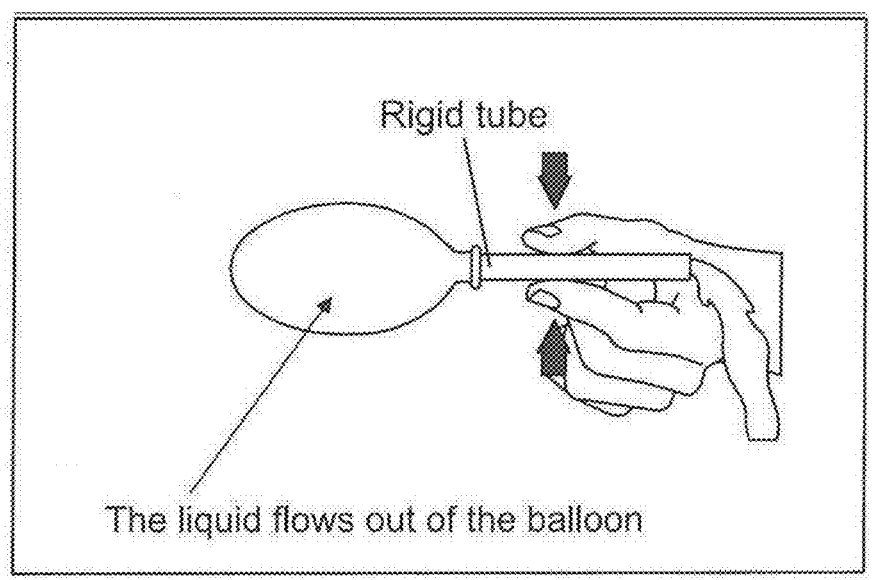
Figure 12B:
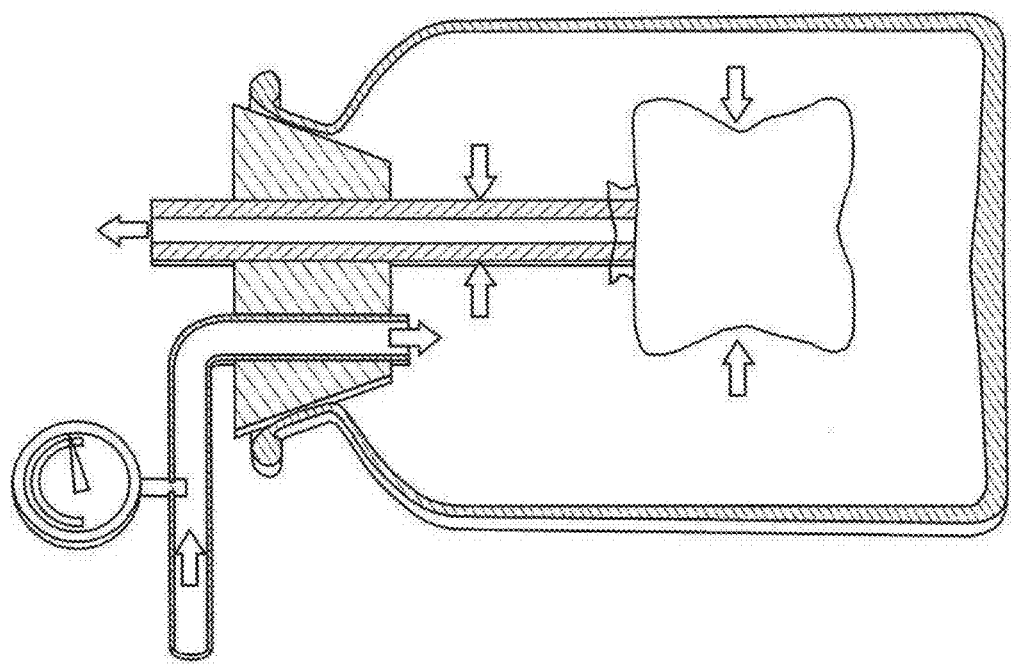
FIGS. 12A and 12B are drawings of another model demonstrating the importance of maintaining flexibility of the subarachnoid veins. The model shows a system comprising a closed chamber housing a sponge; the sponge is attached to a tube which is open to the outside of the chamber. The chamber also includes a path for liquid to be injected into the chamber, which path is attached to a manometer that measures the pressure of the liquid entering the chamber. The only difference between FIGS. 12A and 12B is that tube in FIG. 12A is flexible whereas the tube in FIG. 12B is rigid.
Figure 12A:
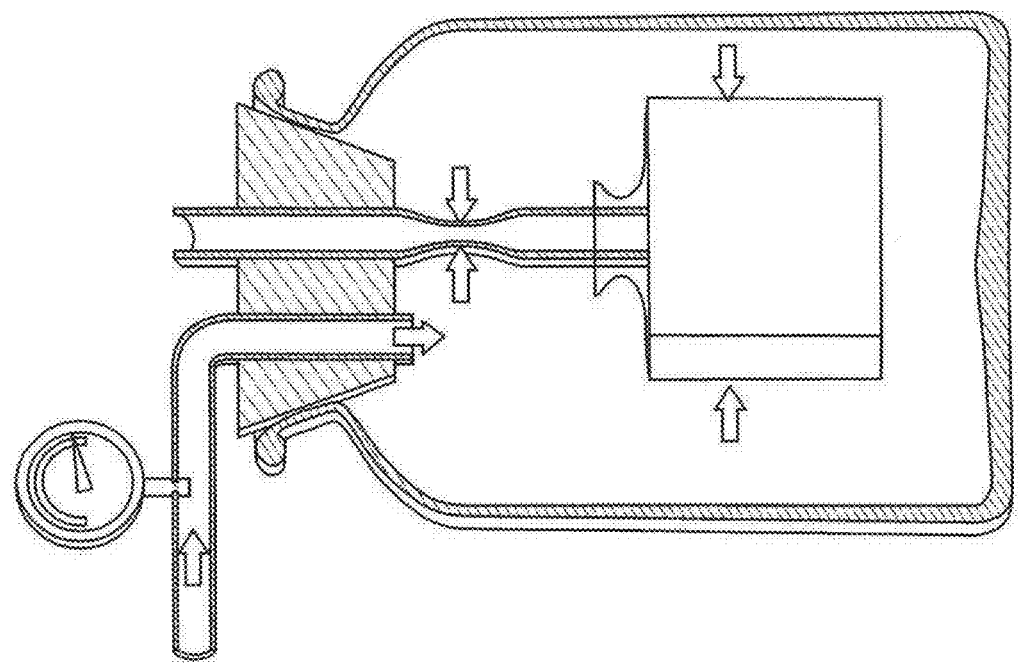
Figure 13:
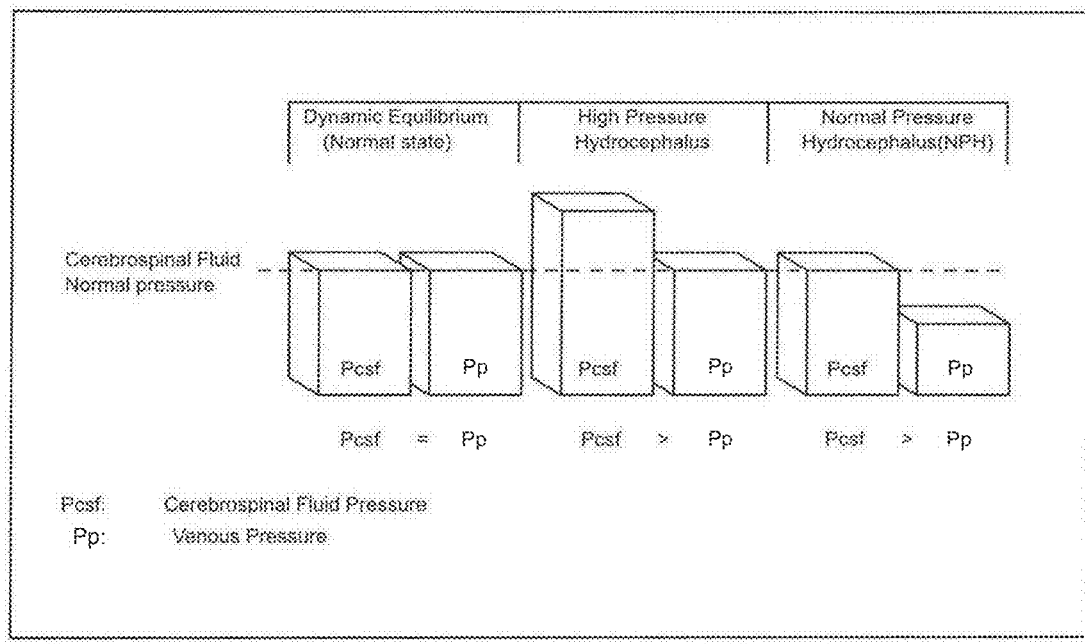
FIG. 13 is a bar graph comparing the pressure of the CSF and the venous pressure in the normal brain, in the brain of a patient with high pressure hydrocephalus and in the brain of a patient with normal pressure hydrocephalus.

As shown in FIGS. 9A and 9B, the decreased flexibility of the subarachnoid veins can be at least partially attributed to the accumulation of collagen fibrils on the exterior of the wall of the veins. Therefore, in some aspects of the invention, the pharmacologic agent is an agent that inhibits collagen accumulation or degrades collagen. Agents that inhibit collagen accumulation and/or degrade collagen include, for example, agents that inhibit collagen synthesis, agents that enhance collagen degradation, agents that inhibit formation of collagen fibrils and/or agents that inhibit folding of the protein. Such agents include, for example, anti-collagen antibodies, collagenase enzymes, phorbol 12-myristate 13-acetate (Goldstein et al. (1990). JBC 265: 13623-8), cis-4-hydroxyproline and derivatives thereof, proline and derivatives thereof, L-azetidine-2-carboxylic acid and derivative thereof, tranexamic acid, TNF-a (Pischon et al. (2004). JBC 279: 30060-5 and prolyl-4-hydroxylase inhibitors (Nwogu et al. (2001). Circulation 104: 2216-21). In some embodiments, the pharmacologic agent comprises a derivative, salt, or prodrug of any of the above-mentioned agents.

In an embodiment, the method comprises acquiring knowledge that the patient is in need of increase in the flexibility of the veins of the subarachnoid space. In an embodiment, the method comprises acquiring knowledge that the patient is in need of an anti-fibrotic agent or anti-collagen agent to treat the NPH. In an embodiment, the method comprises acquiring knowledge of the level of flexibility of the subarachnoid veins, or knowledge of the level of, e.g., the existence of, collagen deposition on the subarachnoid veins of the patient. In an embodiment, the method comprises selecting the pharmacologic agent on the basis that it will relieve a symptom or characteristic of the NPH. In an embodiment, the method comprises selecting the pharmacologic agent on the basis that it will reduce the amount of collagen, or impede the deposition of collagen, on the veins of the subarachnoid space. In an embodiment, the method comprises selecting the pharmacologic agent on the basis that it will increase the flexibility of the veins of the subarachnoid space.

The pharmacologic agent can be administered in any suitable manner that allows the agent to exert its effects in the brain, e.g., on the subarachnoid vessels of the brain, particularly the adventitia. In some aspects of the invention, the agent is administered directly or indirectly into the CSF. Systemic and intracerebral routes have been reported for the purpose of delivering drugs to the CSF. A consideration in intravascular administration is of course penetration through the blood brain barrier (BBB), especially for polar or hydrophilic agents. However, a number of techniques for systemic delivery of drugs into the CSF and brain have been described, for example, encapsulation of drugs into liposomes and the use of nanomedicines (Merkus et al. (2002). Br. J. Clin. Pharmacol. 54(5): 560 and Nowacek et al. (2009). Nanomedicine 4(5): 557-74). In yet another aspect, the agent is administered intrathecally or intracerebroventricularly. In an embodiment, the pharmacologic agent is administered directly into the CSF. In an embodiment, the pharmacologic agent is administered indirectly into the CSF. For example, the pharmacologic agent can be administered to a part of the patient's body other than the CSF, in a manner that allows it to access the CSF. For instance, the agent can be administered with an excipient that improves its uptake into CSF or can be conjugated to a moiety that improves its uptake into the CSF.

In an embodiment, the patient has been diagnosed with a non-NPH dementia, e.g., Alzheimer's disease. In an embodiment, the patient has been incorrectly diagnosed with a non-NPH dementia, e.g., Alzheimer's disease. In an embodiment, the patient has been treated for a non-NPH dementia, e.g., Alzheimer's disease, e.g., with an acetylcholinesterase inhibitor (e.g., tacrine, rivastigmine, galantamine, or donepezil) or an NMDA receptor antagonist (e.g., memantine), and in an embodiment, the result of such treatment have been unsatisfactory.

In an embodiment, the patient has diabetes, and e.g., has been treated with an anti-diabetic drug, e.g., insulin, an insulin analog, or an agent that increases insulin sensitivity (e.g., biguanides such as metformin, or thiazolidinediones such as rosiglitazone, pioglitazone, and troglitazone), an agent that increases insulin secretion (e.g., sulfonylureas), or Alpha-glucosidase inhibitors (e.g., miglitol). In embodiments, the method further comprises administering an anti-diabetic drug, e.g., insulin, an insulin analog, or an agent that increases insulin sensitivity (e.g., biguanides such as metformin, or thiazolidinediones such as rosiglitazone, pioglitazone, and troglitazone), an agent that increases insulin secretion (e.g., sulfonylureas), or alpha-glucosidase inhibitors (e.g., miglitol).

In an embodiment, the patient has, or has had, cancer, and, e.g., has been treated with a chemotherapeutic, e.g., an alkylating agent such as cisplatin, an anti-metabolite such as methotrexate, an anti-microtubule agent such as paclitaxel, a topoisomerase inhibitor such as irinotecan, or a cytotoxic antibiotic such as actinomycin. In embodiments, the method further comprises administering a chemotherapeutic, e.g., an alkylating agent such as cisplatin, an anti-metabolite such as methotrexate, an anti-microtubule agent such as paclitaxel, a topoisomerase inhibitor such as irinotecan, or a cytotoxic antibiotic such as actinomycin. While not wishing to be bound by theory it is believed that treatments of the invention will modulate undesirable effects of the chemotherapeutic, e.g., methotrexate.

The present invention also encompasses methods of diagnosing NPH in a patient. In one aspect, NPH is diagnosed by detecting decreased flexibility or fibrosis of the subarachnoid veins, or detecting a marker thereof. In a further aspect, the invention comprises increasing the intraparenchymal venous pressure in a patient and monitoring said patient for an improvement in symptoms. Persons of skill in the art are familiar with methods of monitoring patients for an improvement in symptoms associated with NPH. NPH is currently identified in patients by CSF fluid diversion by lumbar puncture and drainage and monitoring the patient for an improvement in symptoms (Verees et al. (2004)). In some aspects, the intraparenchymal venous pressure can be increased by introducing the patient to a hyperbaric environment. In some embodiments, the CSF is vented to outside the hyperbaric environment, e.g., by a ventricular catheter or spinal tap.

The results of any of the diagnostic methods described herein can be used to evaluate or select a patient for a treatment for NPH, e.g., a treatment described herein. The treatment can be an initial treatment, the continuation of a treatment already started, or the addition of a new treatment modality to, or in place of, an existing treatment regime. In an embodiment, a diagnostic method described herein can be used to evaluate the stage or level of advancement of the NPH, or of the efficacy of a treatment, e.g., a treatment described herein.

EXAMPLES

Example 1: Hypothesis and Model for the Development of NPH

This Example describes the hypothesis for how NPH develops. The subsequent examples provide support for this hypothesis.

The following abbreviations are used herein:
$P_{csf}$=Intraventricular CSF pressure
$P_{sa}$=Subarachnoid CSF pressure
$P_v$=Extraparenchymal venous pressure, measured in the SSS
$P_p$=Intraparenchymal venous pressure
$P_c$=Central Venous pressure measured in the Right Atrium
$P_{ei}$=Effective Differential Intraventricular CSF Pressure (Pcsf-Pp)

The Superficial Cerebral veins, which emerge from the brain surface, travel through the subarachnoid space, submerged in Cerebrospinal Fluid (CSF), to join the dural venous sinuses and drain into the Superior Sagittal Sinus (SSS). The normal pressure in the SSS in a horizontal position is approximately 70 mm $H_2O$ (Pv=Extraparenchymal venous pressure, measured in the SSS). Therefore, this would also be the pressure of the subarachnoid veins and of the brain parenchyma, if these veins were either not surrounded by CSF, or if they were rigid tubes.

The CSF also drains into the SSS, but through a different pathway, the arachnoid villi. The resistance through these villi is greater than the pressure of the SSS. Therefore, the normal pressure of the CSF in the subarachnoid space (Psa=Subarachnoid CSF pressure) is approximately 120 mm $H_2O$ in a horizontal position. Because the subarachnoid veins have very thin and flexible walls, the CSF surrounding them will flatten the veins and increase their resistance until the internal pressure of the veins is equal to that of the CSF surrounding them. Any variation of the CSF pressure in the subarachnoid space is immediately transmitted to these veins, either decreasing or increasing their luminal cross-sectional area, changing the resistance of the parenchymal venous outflow before draining into the SSS. Therefore, subarachnoid CSF pressure induces parallel variations in the intraparenchymal venous system pressure. Likewise, a venous pressure variation at the level of the SSS or thereafter is transmitted to both intraparenchymal venous and CSF systems equally, because both drain into the SSS. These two mechanisms assure a constant hydrostatic loading of the brain tissue or sponge-like parenchyma.

The brain tissue or parenchyma is subjected to two opposing pressures. One is produced by the CSF system (Pcsf), which tends to enlarge the ventricles, and the other is produced by the intraparenchymal venous system (Pp), which tends to reduce the ventricles. As long as these two pressures remain equal regardless of their absolute values, the tissue is not submitted to the slightest degree of stress or distortion, and the ventricular size remains unchanged in a steady state condition.

The gradient which controls the degree to which liquids may be squeezed out or into the parenchymal sponge, and in consequence change and control ventricular size, is the differential existing between the intraventricular CSF pressure ($P_{csf}$) and the intraparenchymal venous pressure ($P_p$). This gradient is designated the effective differential intraventricular CSF pressure ($P_{ei}=P_{csf}-P_p$). When $P_{csf}>P_p$, then $P_{ei}>0$ and the fluid is squeezed out of the parenchyma; when $P_{csf}<P_p$, then $P_{ei}<0$ and the fluid is squeezed into the parenchyma.

Depending on the hardening of the walls of the veins in NPH, the CSF will not be able to flatten them as much and their internal pressure will drop as low as the pressure of the SSS.

For hydrocephalus to occur, the effective differential intraventricular CSF pressure ($P_{ei}$) must increase. This can be accomplished by either increasing intraventricular CSF pressure ($P_{csf}$) above $P_p$, or by decreasing intraparenchymal venous pressure ($P_p$) below $P_{csf}$, since $P_{ei}=P_{csf}-P_p$. An increase in $P_{ei}$ produces an increase in the tangential and radial stresses of the parenchyma, pushing the ventricular wall towards the periphery of the brain. If $P_{ei}$ thereafter returns to its normal value (therefore $P_{csf}=P_p$), the parenchymal tissue will have yielded bioplastically and will remain in this new steady state condition of permanent set with dilated ventricles, having reached the mechanics of NPH.

Figure 6:
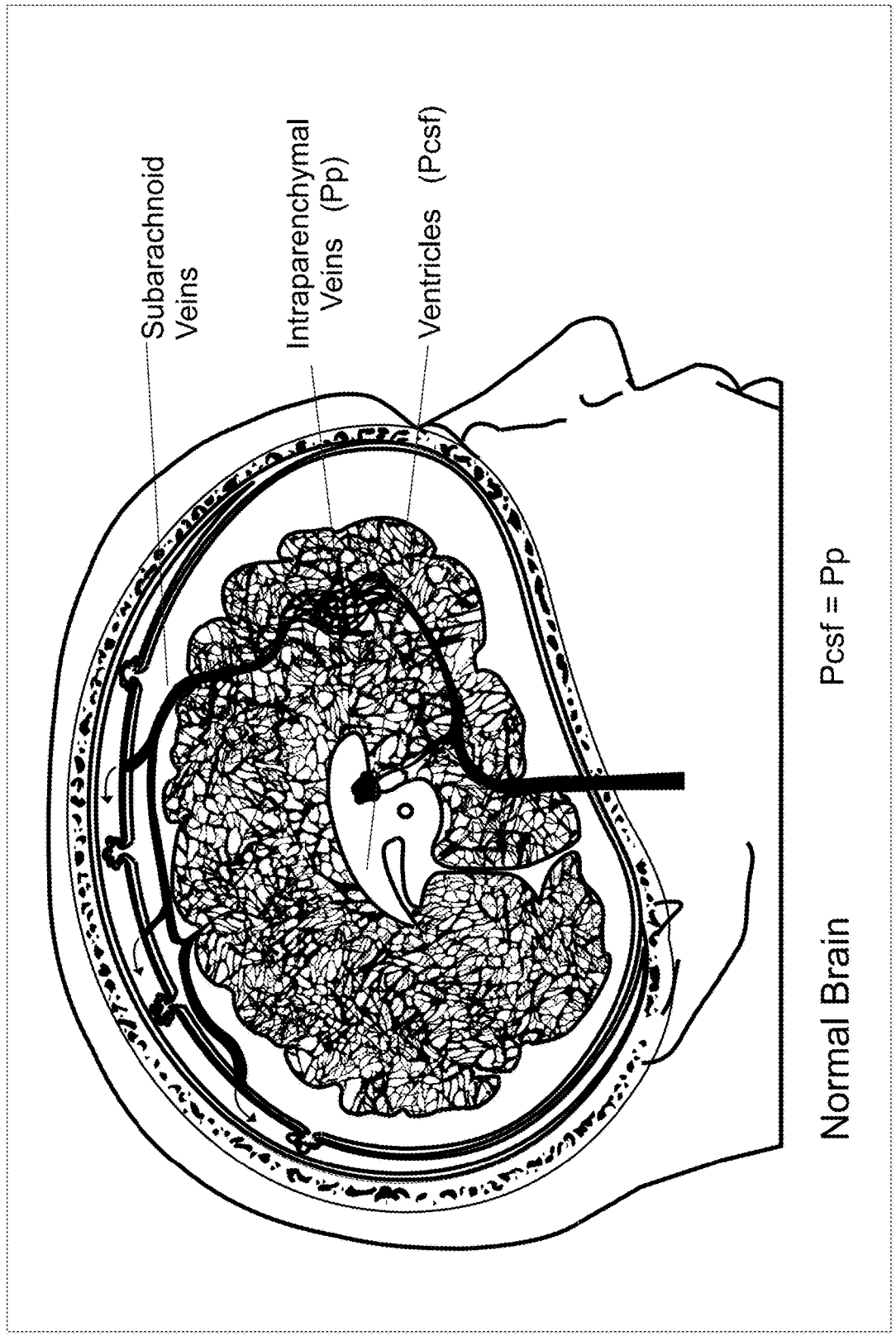
FIG. 6 is a drawing showing the cross-section of a normal brain where the subarachnoid veins and intraparenchymal veins are indicated. Ventricular size is normal and the veins are normal.
Figure 7:
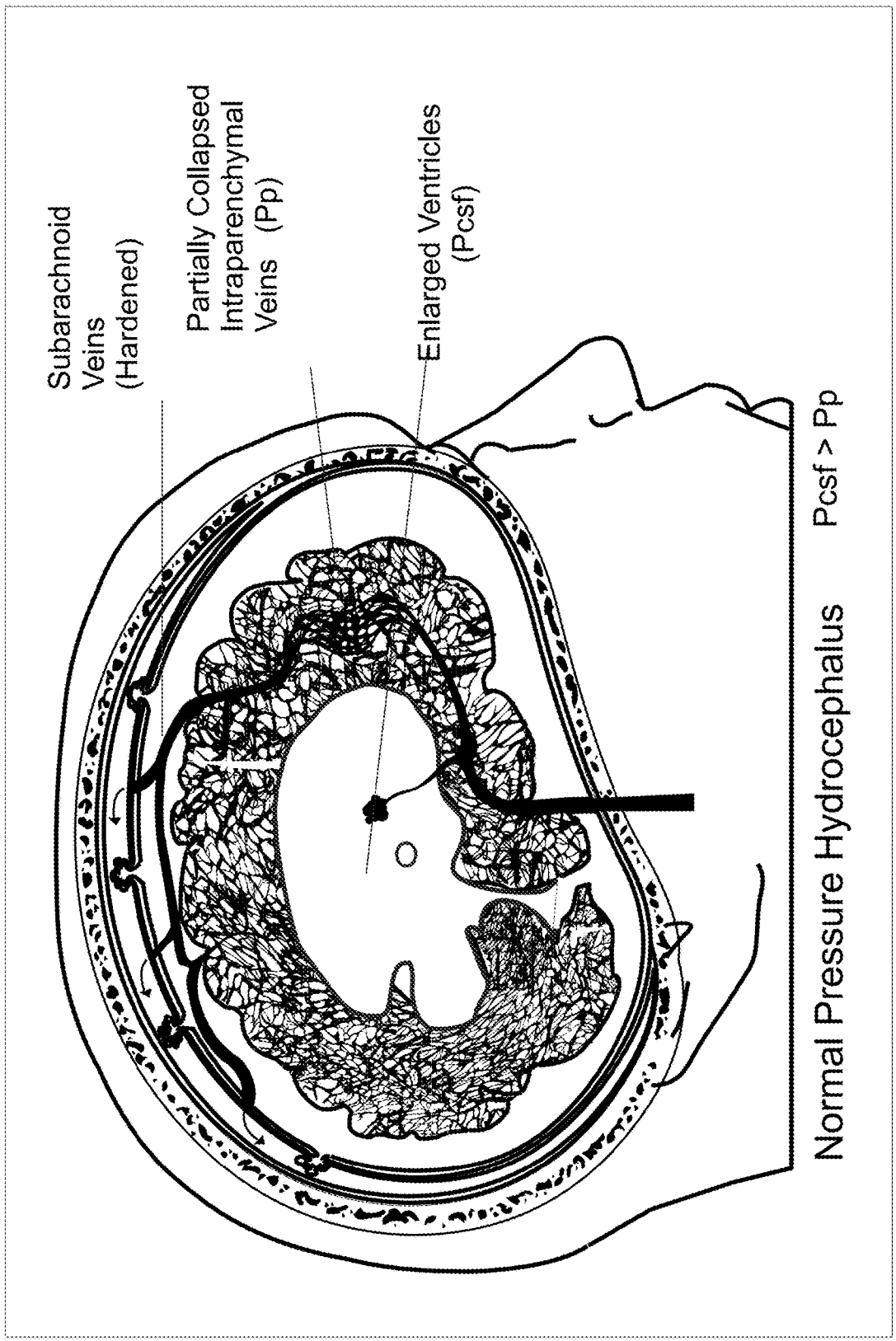
FIG. 7 is a drawing depicting the hardened subarachnoid veins, the partially collapsed intraparenchymal veins and the enlarged ventricles of a patient with Normal Pressure Hydrocephalus.
Figure 8A:
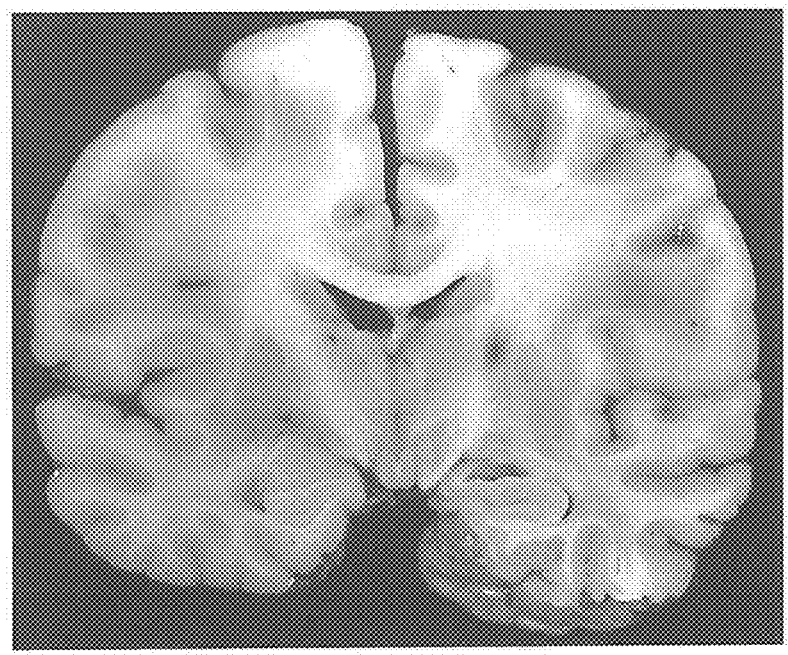
FIGS. 8A and 8B are photographs of brain cross-sections.
Figure 8B:
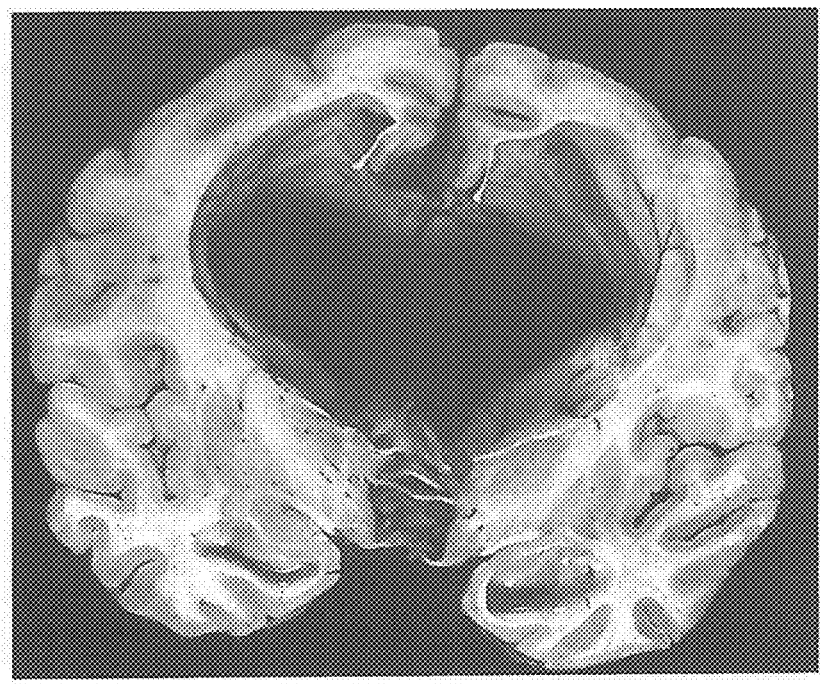

FIGS. 6 and 7 represent normal and NPH brains according to this hypothesis.

Example 2: Observations Regarding CSF Pressure Measurements in Humans Inside a Hyperbaric Chamber CSF pressure measured by lumbar puncture in patients in a horizontal position remained constant as the patient's environment changed from sea level to a high altitude (9,000 ft above sea level). These preliminary observations precipitated further studying of CSF pressure in a hyperbaric chamber.

Figure 14A:
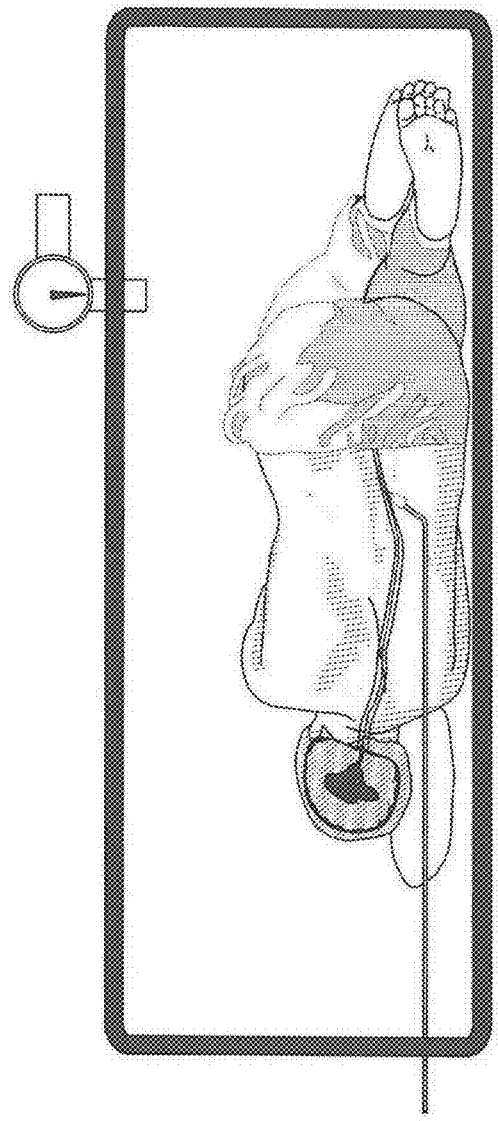
FIGS. 14A and 14B illustrate a patient inside a variable altitude chamber with a catheter venting the CSF at the spine (spinal tap) to the outside of the chamber.
Figure 14B:
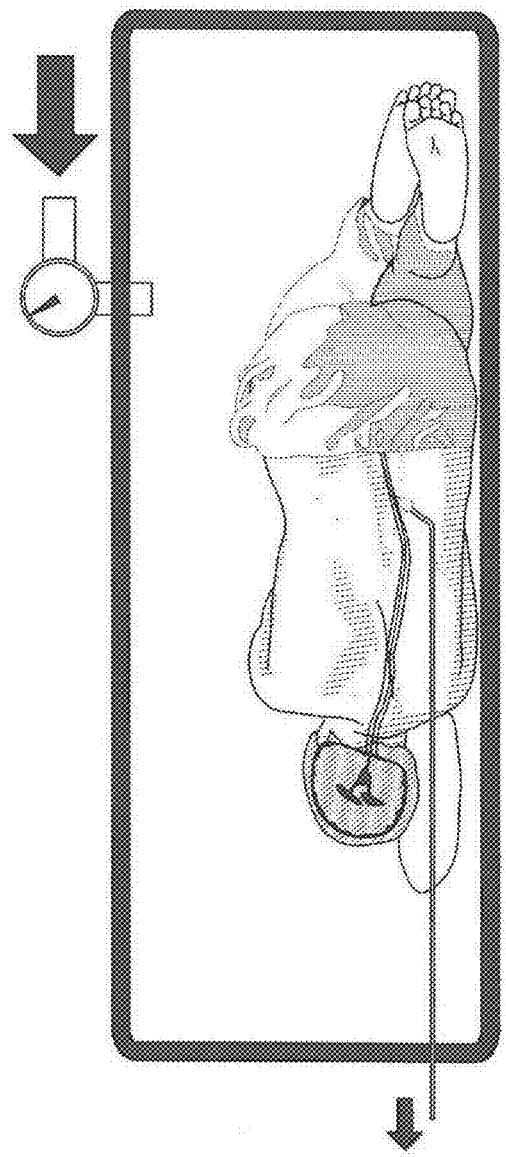
Figure 15A:
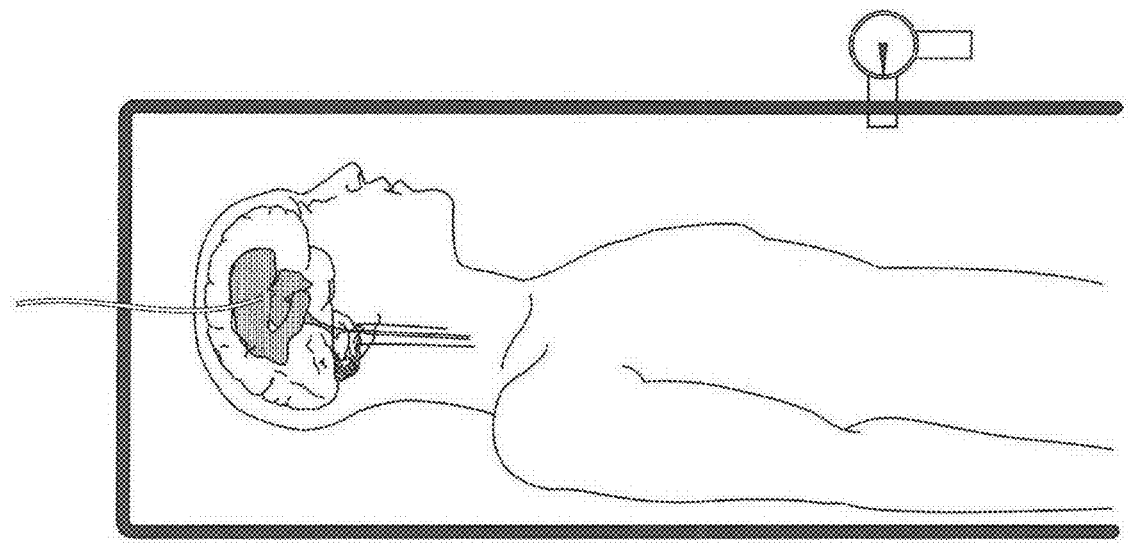
FIGS. 15A and 15B illustrate the same examples as those in FIGS. 14A and 14B, the only difference being that the CSF is vented directly from the ventricles to the outside of the chamber.
Figure 15B:
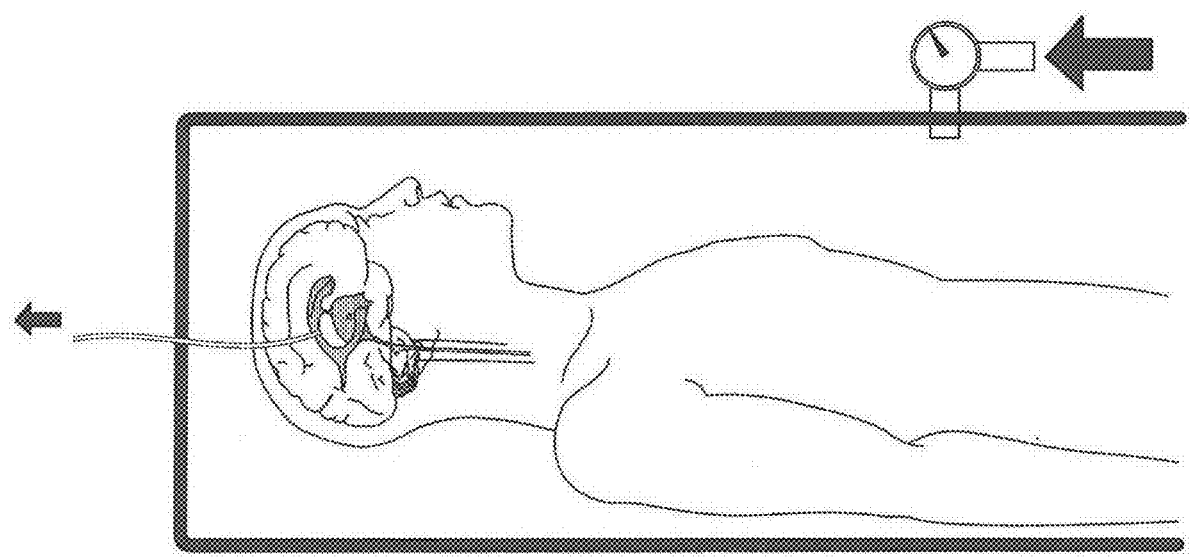
Figure 16A:
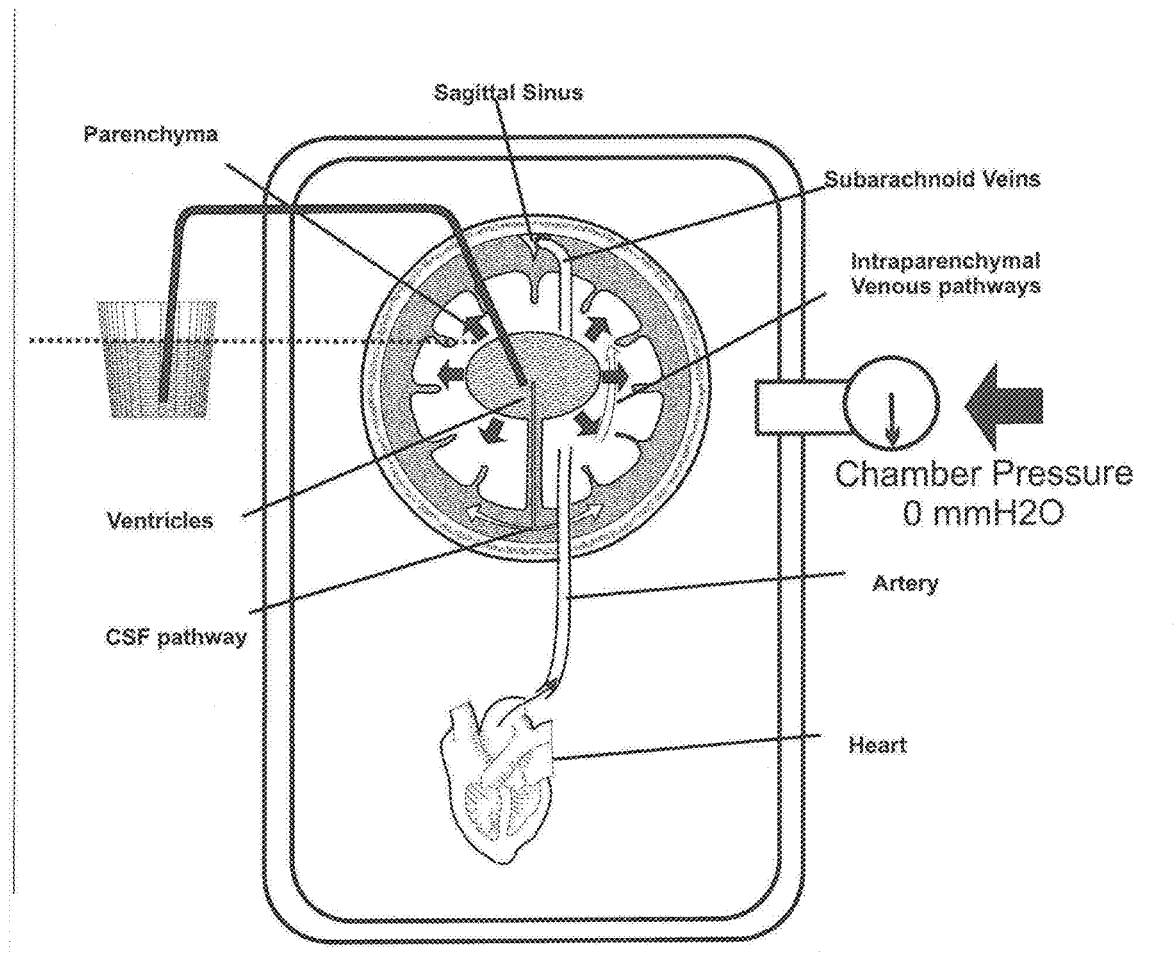
FIGS. 16A and 16B illustrate the same concept as that of FIGS. 14 and 15.
Figure 16B:
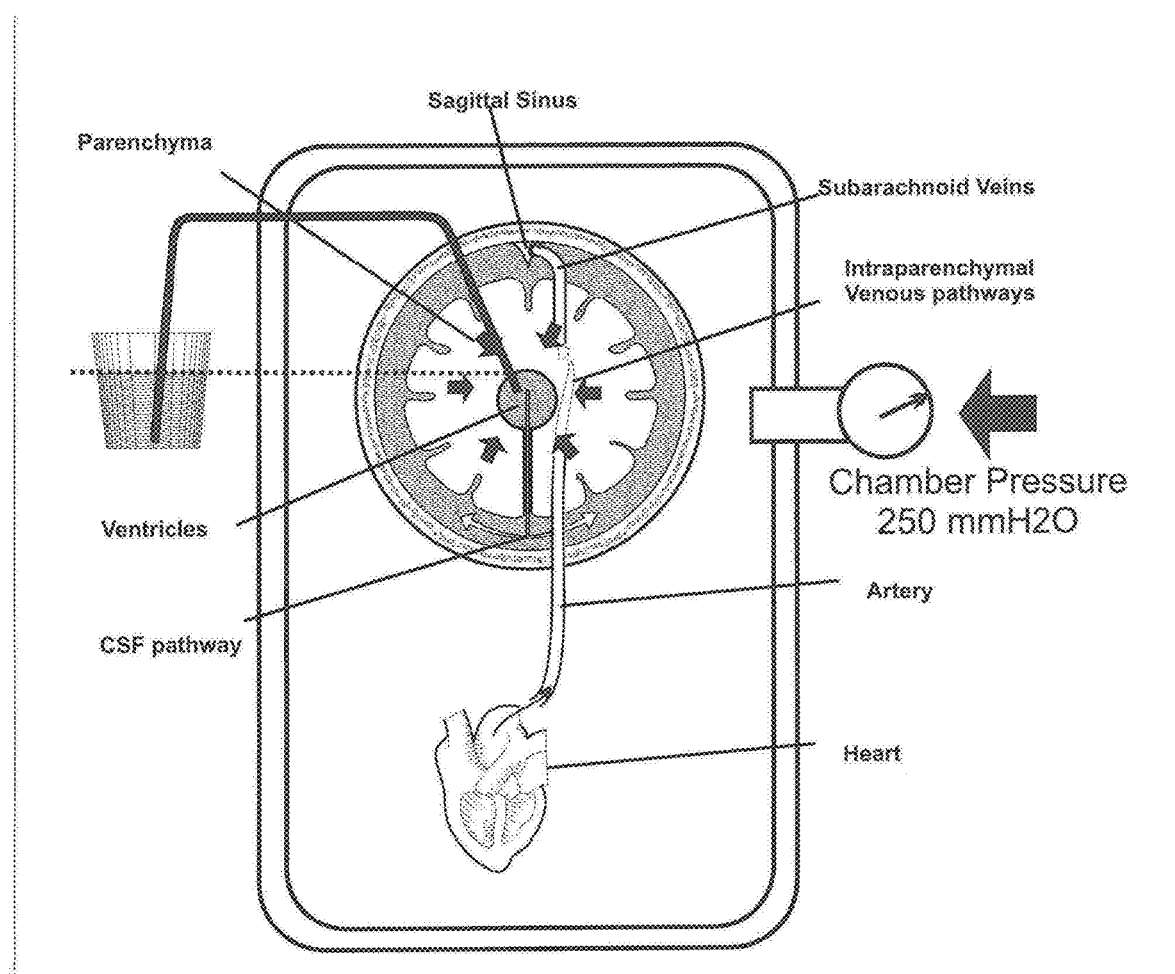

Measurements of CSF pressure were taken in five normal subjects as shown in FIGS. 14A and 14B. Patients were placed in a hyperbaric chamber in the lateral decubitus position. Two manometers, both of the open bore type, were connected to needles tapped in the lumbar region between L3-L4 and L5-S1, respectively. One of the manometers was open to the interior of the hyperbaric chamber, while the other was open to atmospheric pressure by means of a small tube vented outside the chamber. Both manometers showed the same initial reading, but as the pressure inside the chamber was slowly raised from 0 mm of water to 400 mm of water above atmospheric, only the manometer vented to the outside of the chamber, showed an increased reading exactly equivalent to the increment of pressure inside the chamber. The reading of the manometer open to the interior of the chamber remained essentially unchanged.

From this data one can conclude that the CSF system is open to the atmospheric pressure through the venous system. The CSF reading in the manometer vented outside the chamber increased in step with chamber pressure because the increasing chamber pressure was communicated to the closed CSF system via the venous system. The reading of the manometer vented to the interior of the chamber did not change because the fluid in the manometer was subjected to equal pressure increments on both ends of the manometer; one due to CSF increase and the other due to chamber pressure increase.

Example 3: Cranial Cavity Pressure Measurements in Dogs

The essence of this portion of the research program was to simultaneously measure and correlate Ventricular (Pcsf), Parenchymal (Pp), SSS (Pv) and Central Venous Pressures (Pc) of dogs. These measurements were done outside the variable altitude pressure chamber, inside the hyperbaric chamber and inside the hypobaric chamber.

Figure 17:
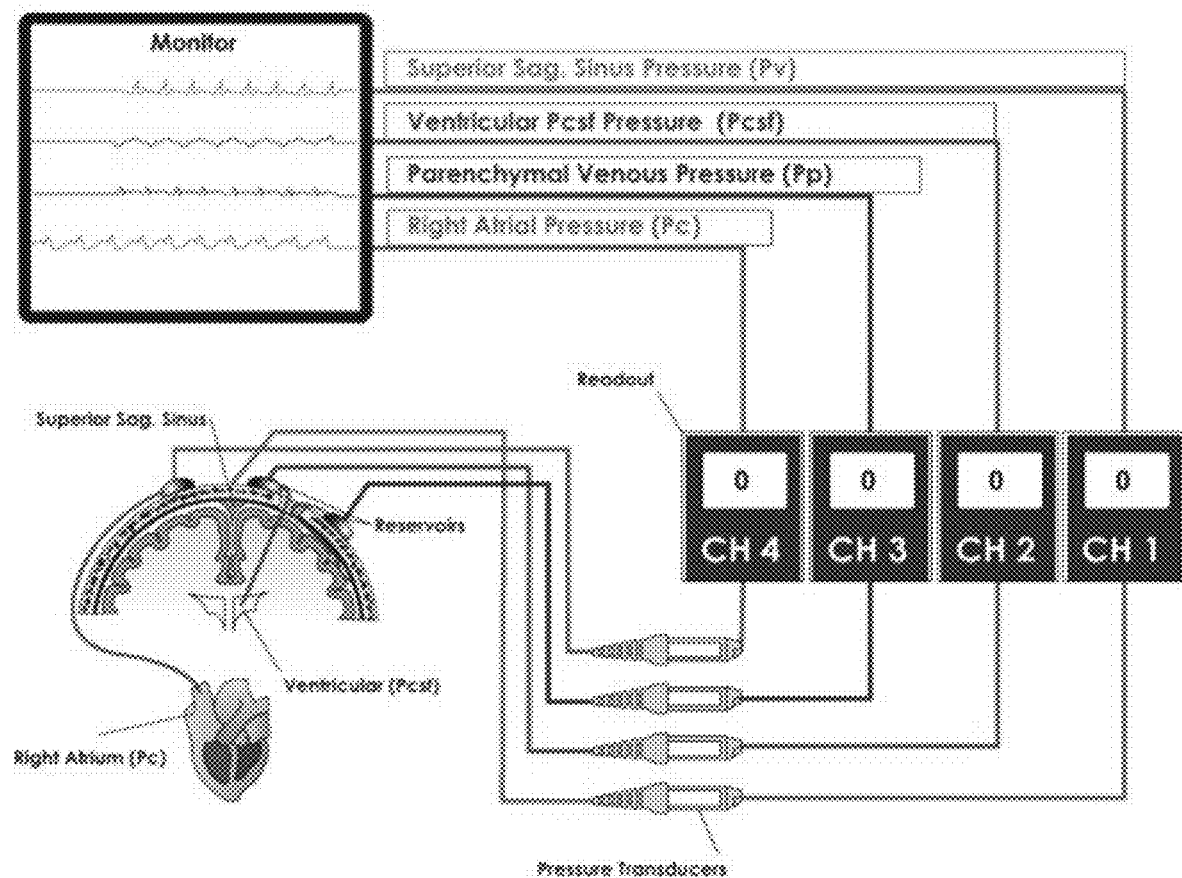
FIG. 17 illustrates the arrangement of catheters, reservoirs and sensors for determining CSF system parameters and their interrelationships.

It is desirable to take the measurements of the relevant parameters not only simultaneously, but also without disturbing the normal cranial cavity mechanics to avoid introducing error. The CSF system parameters and their interrelationships should be determined within a closed cranial cavity. To enable this, a set of catheters, reservoirs and sensors were designed and built specifically for this purpose. These were implanted and connected as illustrated in FIG. 17. Throughout the experimental procedures and while measurements were being taken, the animals were under gas anesthesia administered through a respirator in which the tidal volume and rate were kept constant, enabling the animals to be relaxed and not to hyperventilate.

Figure 18:
FIG. 18 depicts the average pressures of the right atrium, SSS, ventricle, and venous parenchyma in an animal model.

Average Pressures measured (in mm $H_2O$) as seen in FIG. 18:

Right Atrium Pc=20+20
Superior Sagittal Sinus Pv=80+20
Ventricular Pcsf=130+30
Parenchymal Venous Pp=130+30

In normal animals, Pcsf and Pp are always equal and any change in Pcsf produces an immediate and equal change in Pp.

Figure 19:
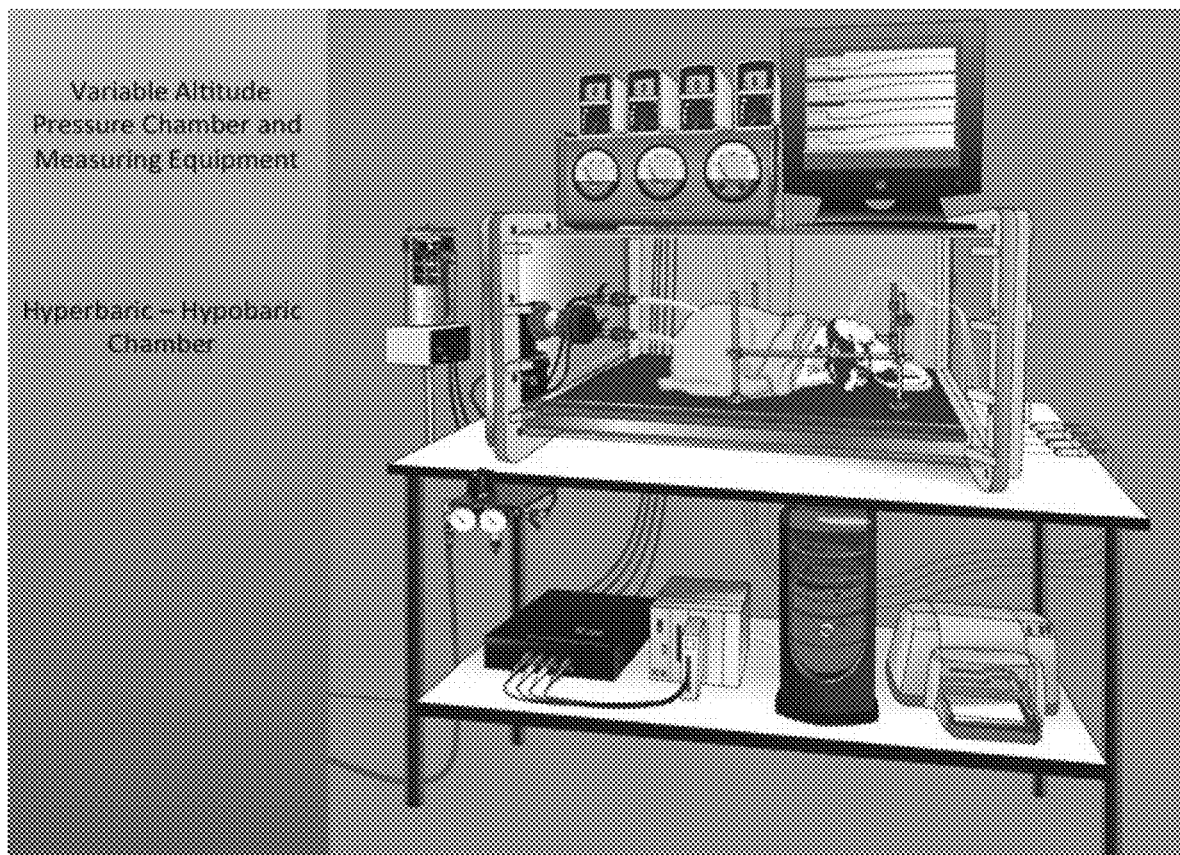
FIG. 19 illustrates the variable altitude pressure chamber used in Example 3.
Figure 20:
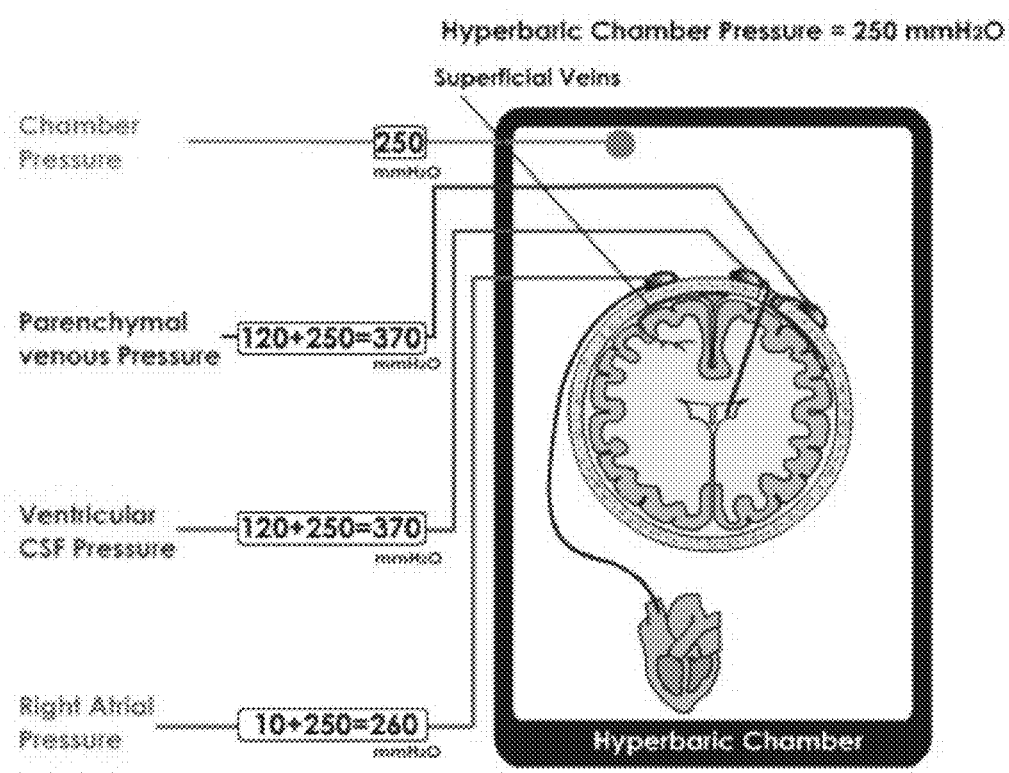
FIG. 20 illustrates the connections between the reservoirs for the hyperbaric chamber experiments.

A variable altitude pressure chamber was constructed. The animals were introduced into the chamber as illustrated in FIG. 19. The reservoirs were connected as illustrated in FIG. 20. Throughout the experimental procedure, the animals were under gas anesthesia administered through a respirator in which the tidal volume and rate were kept constant.

Figure 21:
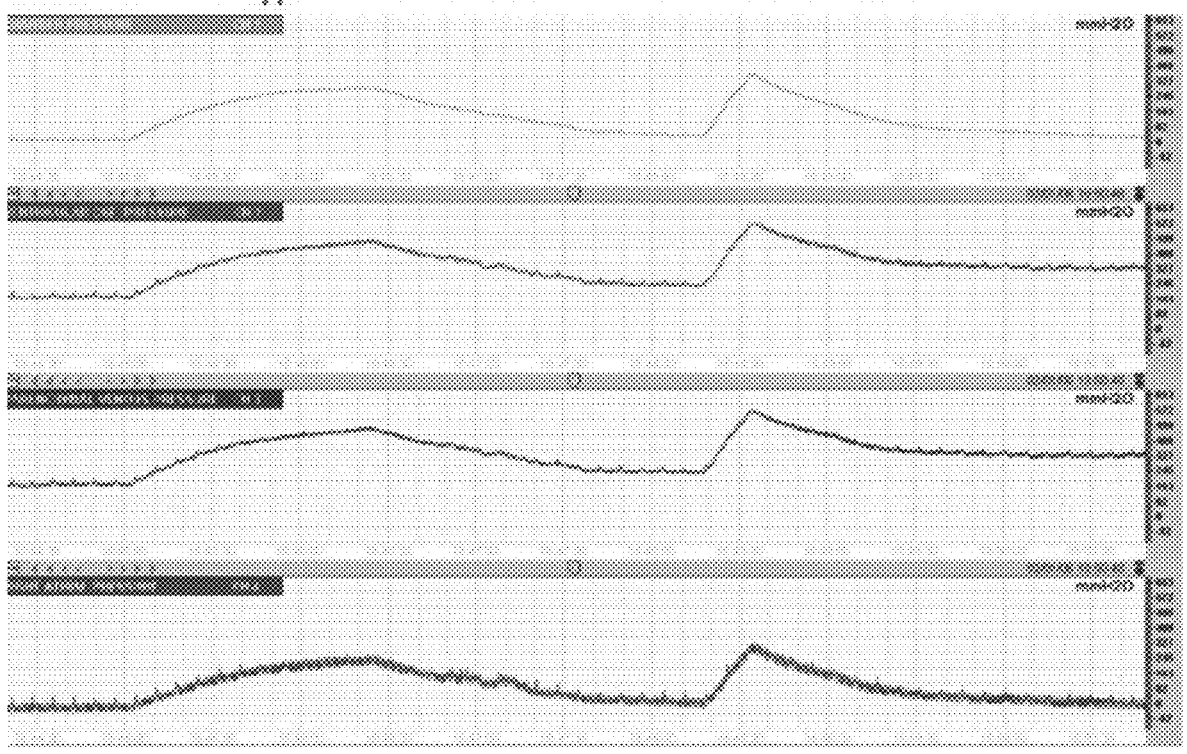
FIG. 21 depicts the parameters measured in the hyperbaric chamber experiments.

As illustrated in FIG. 21, the parameters that were measured were:

Channel 1: Hyperbaric Chamber Pressure
Channel 2: Ventricular Pressure (Pcsf)
Channel 3: Intraparenchymal Venous Pressure (Pp)
Channel 4: Right Atrial Pressure (Pc)

Before the pressure of the chamber was increased, the chamber pressure was at 0 mm $H_2O$; Pc was at 10 mm $H_2O$; and Pcsf and Pp were equal at 150 mm $H_2O$, as seen in the graph. As the chamber is pressurized from 0 mm $H_2O$ to 250 mm $H_2O$, all four pressures increase in equivalent amounts and as the chamber's pressure is decreased back to atmospheric pressure, all four pressures decrease by equivalent amounts. This is due to the fact that the cranial cavity is open to atmospheric pressure through the right atrium of the heart. When the pressure in the chamber is increased (or decreased), this produces an increase (or decrease) in pressure in the right atrium (Pc) or central venous pressure, which produces equivalent changes in Pcsf and Pp. When the pressure of the right atrium is increased, all intracranial pressures are increased and the system remains in equilibrium. This is the reason why a person, who is at the top of a mountain peak or at sea level, even though the atmospheric pressures are quite different, will remain in hydrostatic equilibrium.

Figure 22:
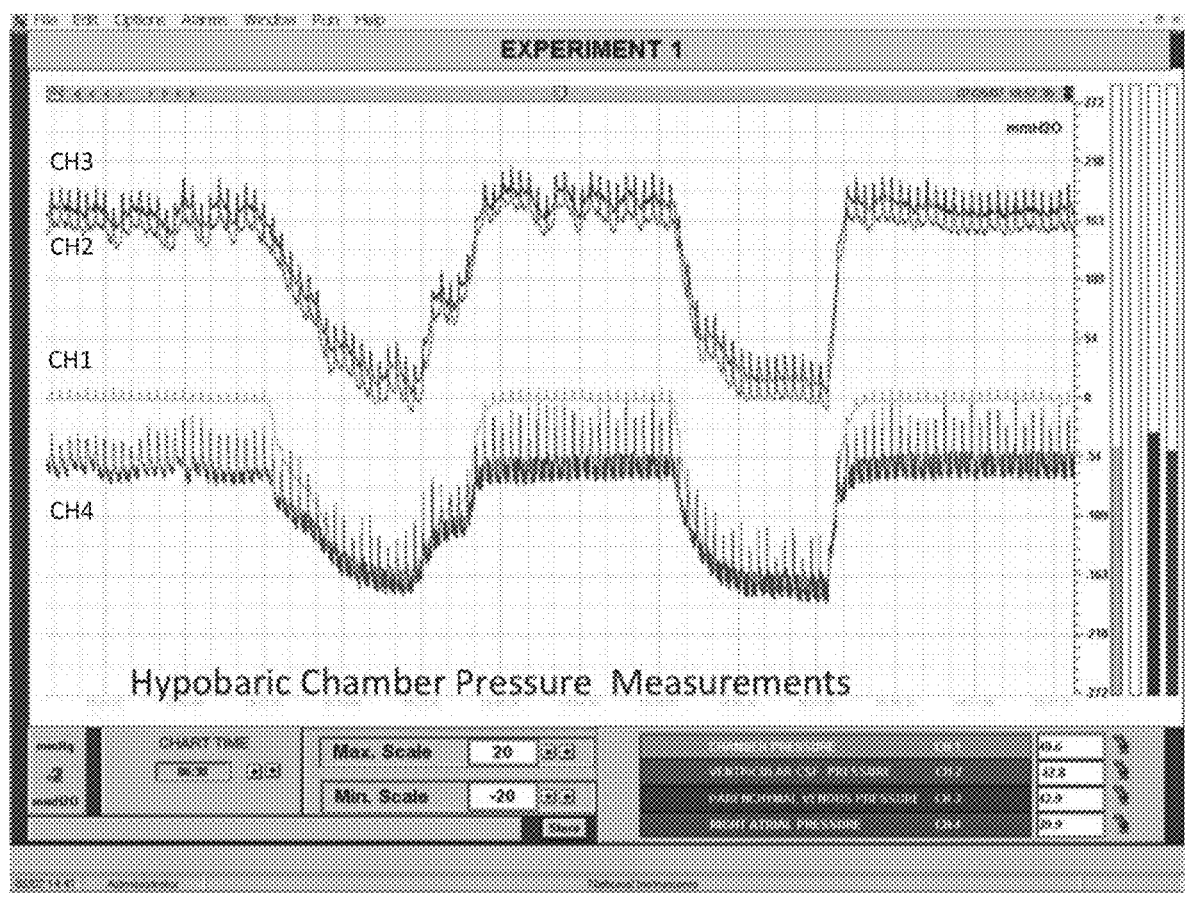
FIG. 22 depicts the parameters measured in the hypobaric chamber experiments.

Following what was done with the hyperbaric chamber, the pressure of the chamber was now reduced from atmospheric pressure to −150 mm $H_2O$ (that is 150 mm $H_2O$ below atmospheric pressure). Notice in FIG. 22 how all the pressures that are being measured will now decrease in approximately the same values as the decrease in pressure inside the hypobaric chamber.

Example 4: Production of Hydrocephalus

Experimental production of hydrocephalus was attempted by ventricular infusion and artificially increased CSF inflow into the ventricles.

Figure 23:
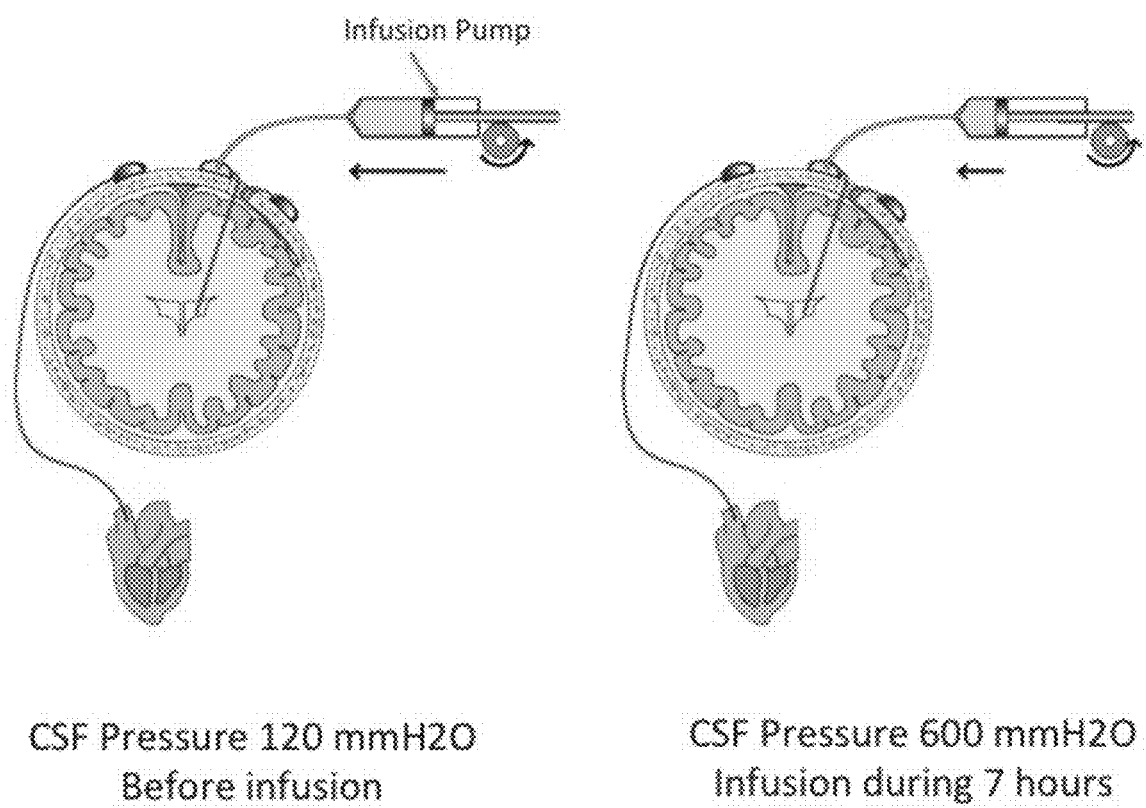
FIG. 23 illustrates the experimental setup for an attempt to produce hydrocephalus by ventricular infusion and artificially increased CSF inflow into the ventricles.

The idea that hydrocephalus is due to an increase in CSF pressure and that this increase results in the enlargement of the cerebral ventricles, is a simplistic concept. Following this idea, it was thought that a simple way of increasing intraventricular CSF pressure to gradually enlarge the ventricles, was by infusing sterile saline solution directly into the cerebral ventricles, as illustrated in FIG. 23.

Before starting the infusion, ventricular size was verified. Contrast medium was injected intraventricularly through the ventricular catheter, followed by lateral and antero-posterior X-ray pictures. This procedure was repeated every two hours to assess ventricular size while the infusion was being performed.

Figure 24:
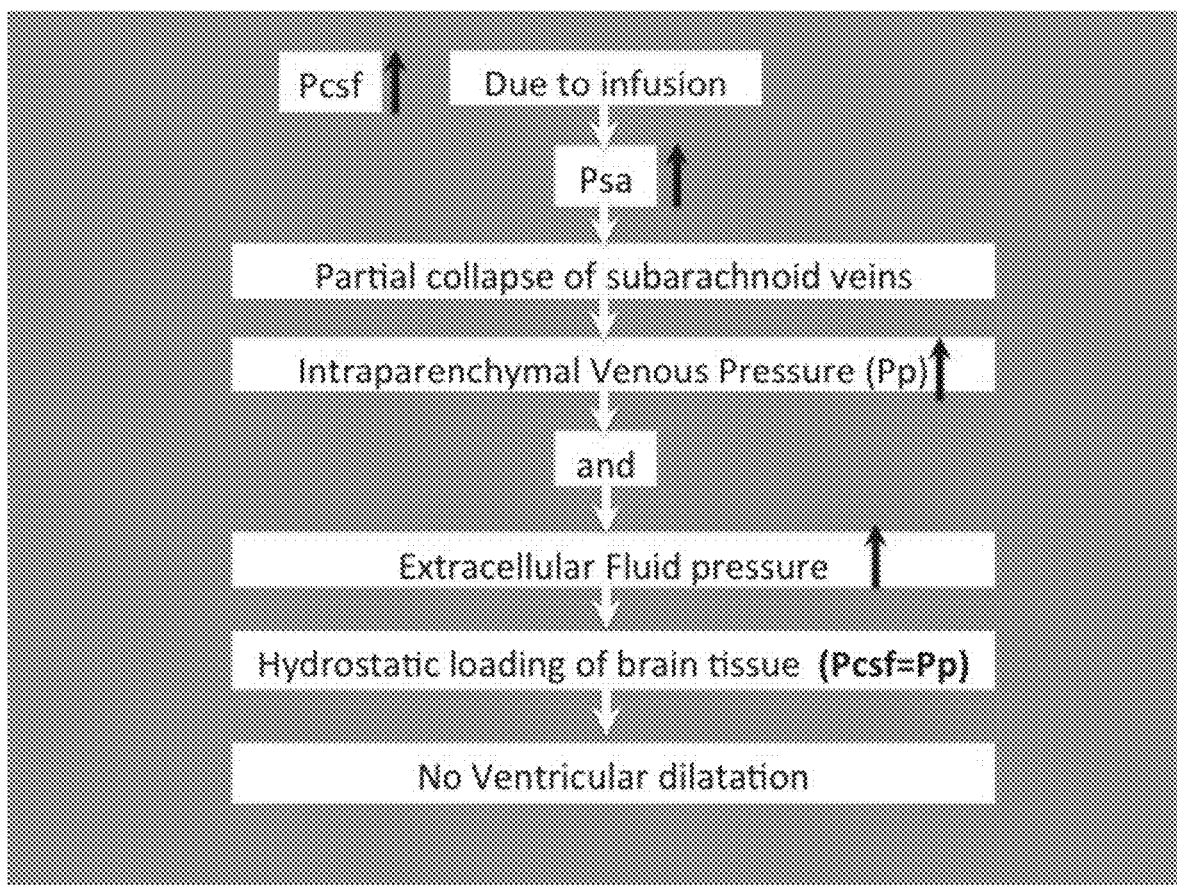
FIG. 24 summarizes the results of the experimental attempt to produce hydrocephalus by ventricular infusion and artificially increased CSF inflow into the ventricles.

The infusion was tried for periods of up to seven hours and the CSF pressure was increased up to 600 mm $H_2O$. Contrary to what was expected, this procedure did not produce any ventricular enlargement whatsoever. The results obtained are interesting and can be interpreted as follows:

As summarized in FIG. 24, ventricular CSF pressure (Pcsf) increases due to the infusion. This produces an immediate increase in subarachnoid CSF pressure (Psa), which in turn produces a partial collapse of the subarachnoid veins and causes an equal increase of pressure in the intraparenchymal veins (Pp). Even though all the pressures are elevated, they are equal and this results in a hydrostatic loading or dynamic equilibrium of the brain tissue, with no ventricular enlargement. For ventricular enlargement to occur, Pcsf has to be greater than Pp.

Next, a hypobaric chamber was tested for the ability to produce hydrocephalus.

Figure 25:
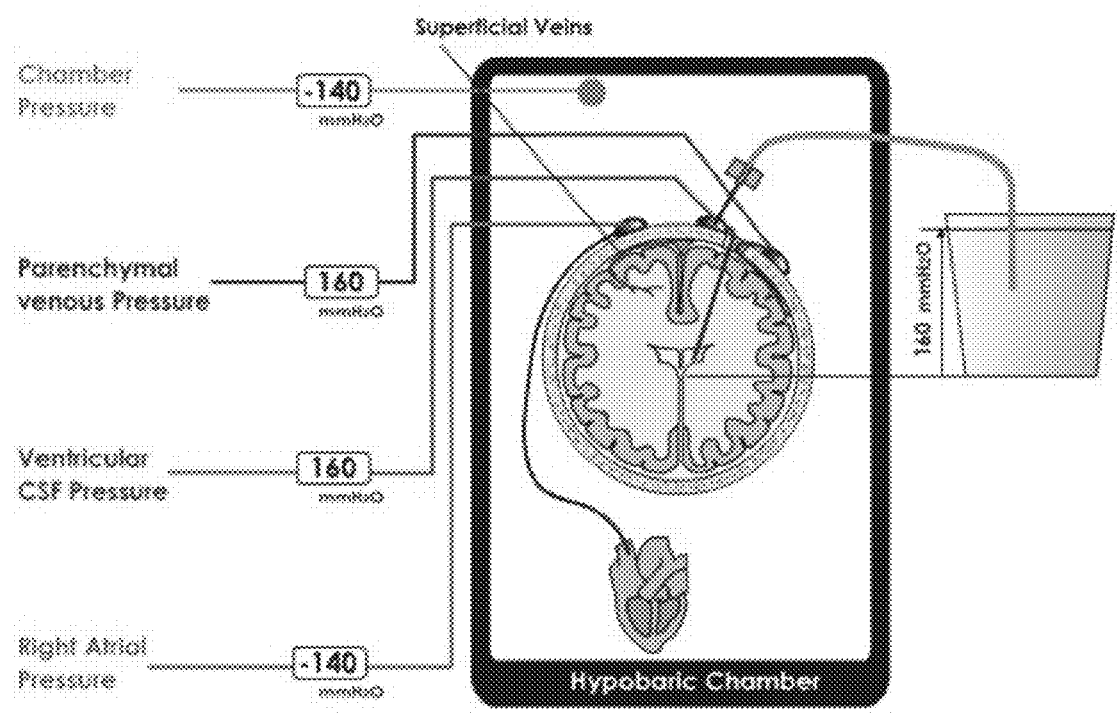
FIG. 25 illustrates the experimental setup for an attempt to produce hydrocephalus using a hypobaric chamber.

Experimental enlargement of the ventricles was attempted by introducing the animals inside the hypobaric chamber, as illustrated in FIG. 25. The reservoirs and catheters were connected as in the previous experiments, but this time, the ventricular catheter was vented to the outside of the hypobaric chamber, into a container with sterile saline solution. This container was elevated in such a way so as to always maintain the intraventricular pressure (Pcsf) at a value of 160 mm $H_2O$, regardless of the pressure inside the chamber. As the chamber's pressure was reduced below atmospheric pressure, all intracranial pressures would be reduced following the chamber's reduction in pressure, with the exception of the ventricular pressure, which was maintained constant at a value of 160 mm $H_2O$, due to the fact that it was vented outside the chamber.

The rationale behind this experiment was that if the ventricular pressure (Pcsf) was kept at a positive value, and the intraparenchymal venous pressure (Pp) was reduced below atmospheric pressure and below the ventricular pressure, due to the reduction in pressure inside the chamber, this would yield a gradient such that Pp<Pcsf, and the ventricles would increase in size.

Figure 26:
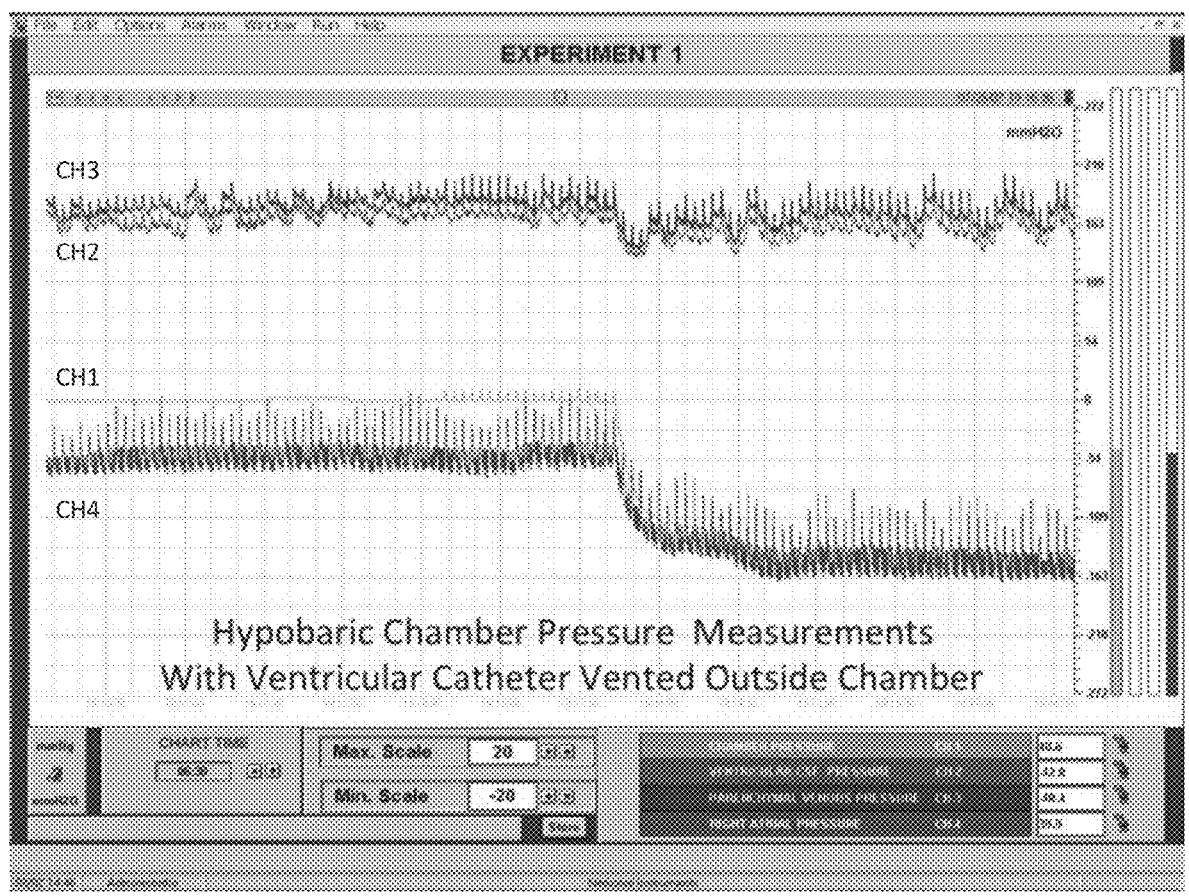
FIG. 26 depicts the pressures resulting from the attempt to produce hydrocephalus using a hypobaric chamber.

As illustrated in FIG. 26, as the pressure inside the hypobaric chamber was reduced, the right atrial pressure (Pc) followed an equal reduction in pressure and the ventricular pressure (Pcsf) stayed at a stable value of approximately 160 mm $H_2O$, as dictated by the container outside the chamber into which the ventricular catheter was connected. Contrary to what was expected, but in agreement to the main feedback hypothesis explained in Example 1, the intraparenchymal pressure (Pp) did not follow the reduction in pressure of either the inside of the chamber or of the right atrium.

The explanation is as follows: normally, the intraparenchymal venous pressure (Pp) follows any change in pressure from the right atrium (Pc), since the intraparenchymal veins ultimately drain into the right atrium. As previously described, the veins emerging from the brain surface travel through the subarachnoid space, submerged in CSF, to join the dural venous sinuses and drain into the SSS, and eventually into the right atrium, as described in Example 1. Because the subarachnoid veins have very thin and flexible walls, the CSF surrounding them will flatten the veins and increase their resistance until the internal pressure of the veins is equal to that of the CSF surrounding them. In this case, the pressure of the CSF in the subarachnoid space was equal to the pressure to which the ventricular catheter was connected outside the chamber, or 160 mm H2O. Therefore, regardless of the reduction of pressure inside the chamber and the fact that the right atrial pressure (Pc) was also reduced, the intraparenchymal venous pressure (Pp) was kept at exactly the same value as that of the ventricular pressure (Pcsf) because of the regulatory mechanism of the CSF pressure in the subarachnoid space over the veins that travel through that space and in turn control the intraparenchymal venous pressure. In conclusion, throughout the experiment, Pp=Pcsf. Since there was no gradient between these two pressures, the ventricles remained at their normal size.

Next, implantation of a ventriculo-atrial shunt with simultaneous blockage of the fourth ventricle was used to produce Normal Pressure Hydrocephalus.

Since neither the ventricular infusion nor the hypobaric chamber experiments produced the expected ventricular enlargement, a different method to induce hydrocephalus was pursued. Following the hypothesis which was presented earlier, it was thought that if the feedback mechanism between the CSF and the veins that travel in the subarachnoid space could be isolated in such a way that the intraventricular CSF pressure (Pcsf) would not be communicated to the CSF in the subarachnoid space, perhaps hydrocephalus with normal pressure could be produced.

Figure 27:
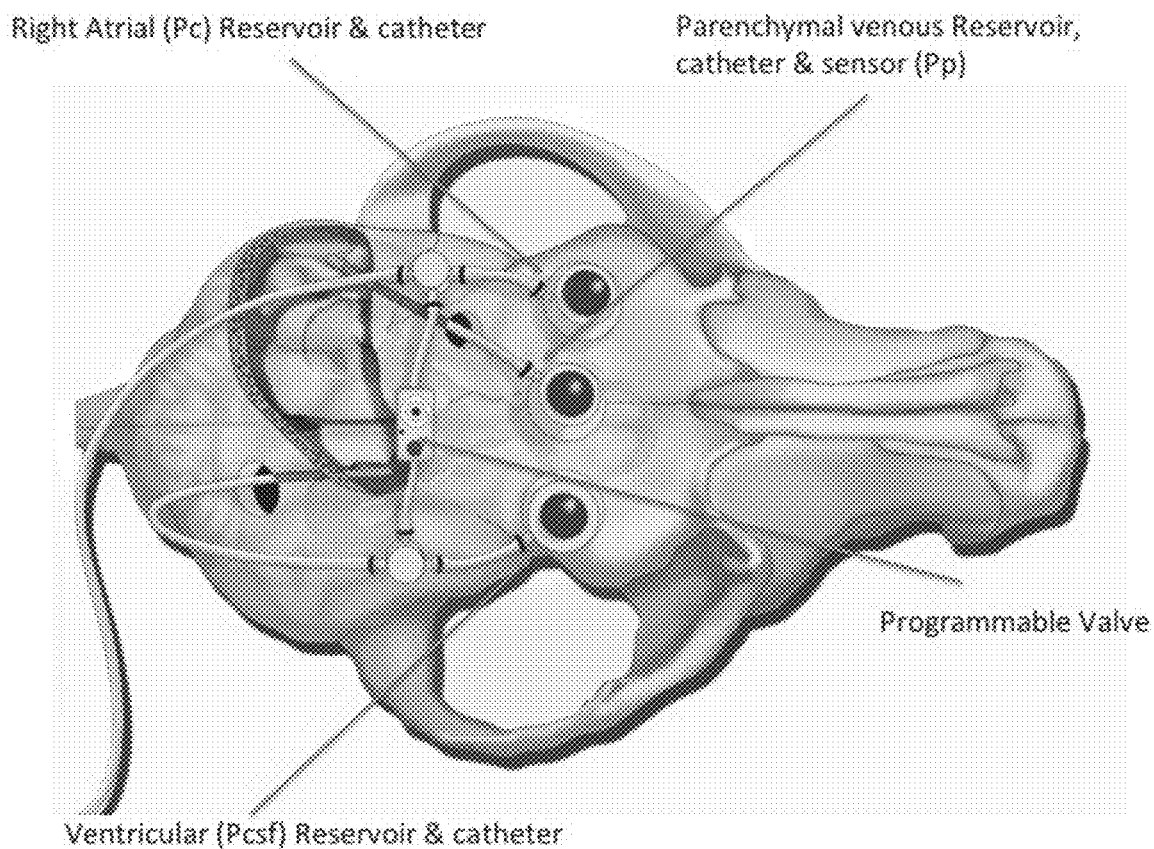
FIG. 27 illustrates the system of sensors used to detect production of NPH by implantation of a ventriculo-atrial shunt with simultaneous blockage of the fourth ventricle.

Using a similar dog model as before, the ventricular, parenchymal and atrial catheters, sensor and their corresponding reservoirs were implanted. Additionally, this time, a programmable valve was implanted between the ventricular catheter and the right atrial catheter, as illustrated in FIG. 27. The pressure of the valve was programmed to 150 mm $H_2O$, which was exactly the same pressure as the intraventricular CSF pressure measured in that dog, before the valve was implanted.

A few days following the implantation of the catheters, sensor, reservoirs and programmable valve, as illustrated in FIG. 27, a surgical procedure was done to produce a complete blockage of the CSF circulation at the level of the fourth ventricle. Using cyanoacrylate (superglue) in gel form, 1.5 cc were injected directly into the fourth ventricle to produce a complete blockage of the CSF circulation. Now, the CSF produced in the lateral and third ventricles would not be able to continue its normal path through the fourth ventricle and into the subarachnoid space. The CSF produced in the lateral and third ventricles would now flow exclusively through the programmable shunt that was implanted between ventricular catheter and right atrial catheter. It is important to note that since the shunt had been previously programmed at 150 mm $H_2O$, which was the normal intraventricular CSF pressure found in the dog before the implants were done, the intraventricular pressure (Pcsf) would continue at its normal value, in spite of the fact that the fourth ventricle was completely obstructed.

Figure 28:
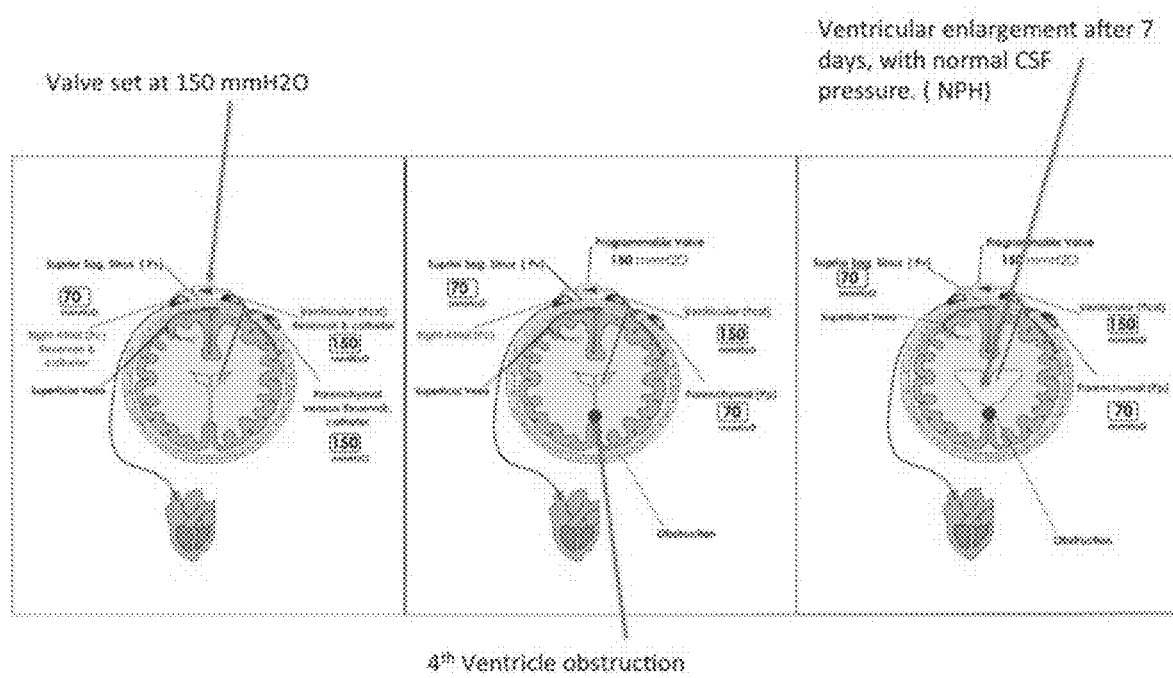
FIG. 28 is a schematic illustrating the experimental setup for producing NPH by implantation of a ventriculo-atrial shunt with simultaneous blockage of the fourth ventricle.

As illustrated in FIG. 28, ventricular pressure (Pcsf), intraparenchymal pressure (Pp) and right atrial pressure (Pc) were monitored on a daily basis. Ventricular size was also monitored every four days by means of lateral X-Rays after introducing contrast medium into the ventricles. It was observed that the ventricles started to enlarge during the first week following the blockage of the fourth ventricle.

What is most interesting to note is that even though the ventricular pressure (Pcsf) was constantly kept at a normal value, the ventricles enlarged. This is due to the fact that because a blockage had been done at the level of the fourth ventricle, the CSF could not flow to the subarachnoid space and therefore the subarachnoid pressure decreased below its normal value. If the CSF pressure in the subarachnoid space decreases, then the pressure acting on the surface of the subarachnoid veins to collapse them is no longer active and this will result in the intraparenchymal pressure (Pp) being reduced to the value of the SSS pressure, which is where the intraparenchymal veins eventually drain.

Figure 29:
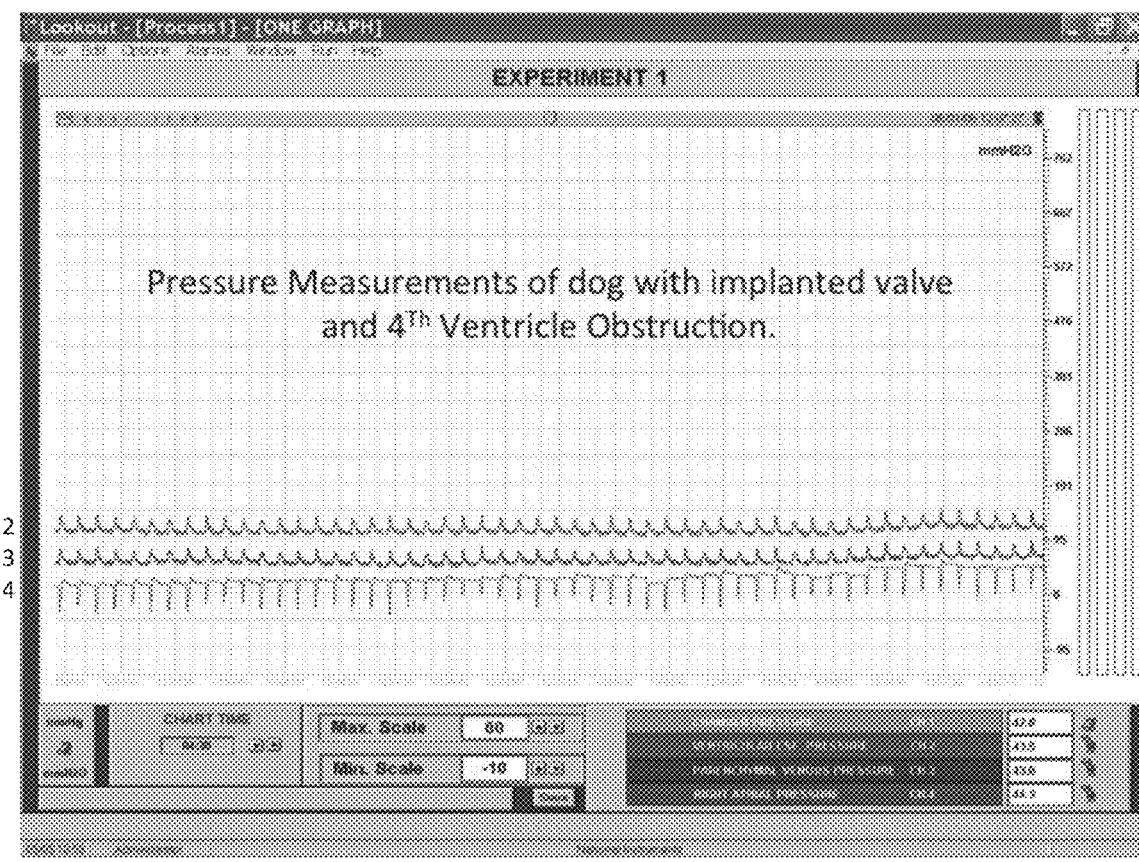
FIG. 29 is a graph of the measured ventricular (Pcsf) and intraparenchymal (Pp) pressures during the first week following the implantation of the ventriculo-atrial shunt and the obstruction of the fourth ventricle.

FIG. 29 is a graph of the measured ventricular (Pcsf) and intraparenchymal (Pp) pressures during the first week following the implantation of the ventriculo-atrial shunt and the obstruction of the fourth ventricle. Notice that the ventricular pressure (Pcsf) is normal and at the value set by the shunt, which is 150 mm $H_2O$. Also notice that the intraparenchymal venous pressure (Pp) is at a lower than normal value, but at a value equivalent to that of the SSS pressure, of approximately 70 mm $H_2O$. This indicates that what produces ventricular enlargement is the gradient between the ventricular pressure (Pcsf) and the intraparenchymal venous pressure (Pp). In hydrocephalus with elevated pressure, the ventricular pressure (Pcsf) is high and greater than the intraparenchymal pressure (Pp) in a way that Pcsf>Pp, and therefore the ventricles enlarge. In Normal Pressure Hydrocephalus, the ventricular pressure (Pcsf) is normal and the intraparenchymal pressure (Pp) is below normal, such that there is also a gradient and Pcsf>Pp, also producing ventricular enlargement.

Figure 30:
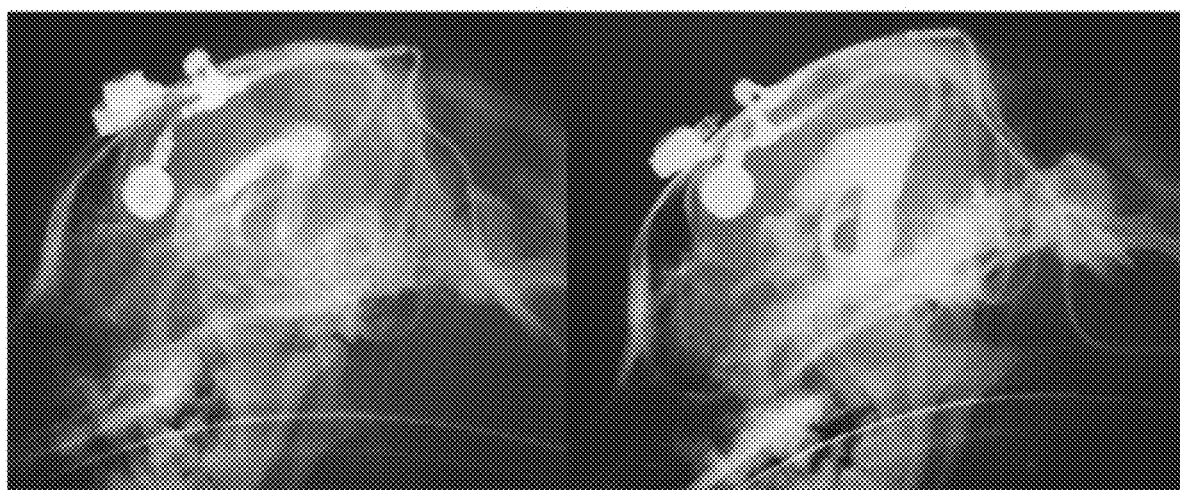
FIG. 30 illustrates two lateral X-rays of the experimental animal's head following the implantation of the ventriculo-atrial shunt and the obstruction of the fourth ventricle.

FIG. 30 illustrates two lateral X-Rays of the dog's head. The left image was taken on Day 1 following the implantation of the ventriculo-atrial shunt and the blockage of the fourth ventricle. Notice the normal size of the ventricles. The right image was taken on Day 8 after the surgical procedure. Even though ventricular pressure (Pcsf) was kept at its normal value, the ventricles greatly increased in size, achieving hydrocephalus with normal ventricular pressure.

Example 5: Hyperbaric Treatment of NPH in Dogs

After having produced Normal Pressure Hydrocephalus as described above (i.e., implantation of a ventriculo-atrial shunt with simultaneous blockage of the fourth ventricle) it was thought that by introducing the hydrocephalic dog into the hyperbaric chamber, an opposite gradient could be created such that Pp>Pcsf, and the enlarged ventricles could then be reduced in size.

Figure 31:
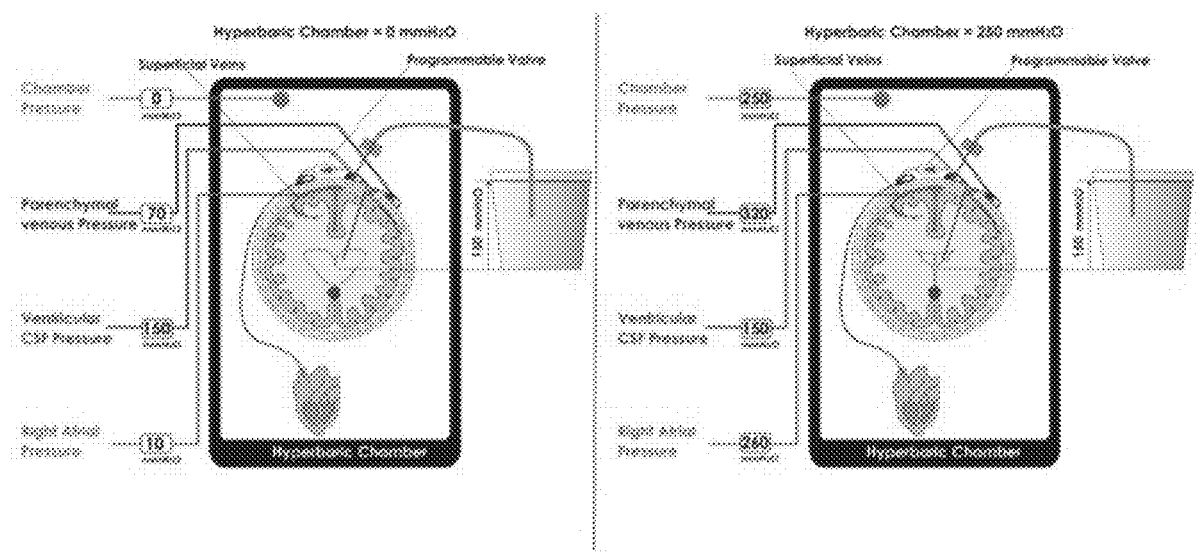
FIG. 31 illustrates the experimental setup for reversing NPH using a hyperbaric chamber.

As illustrated in FIG. 31, the dog was introduced into the hyperbaric chamber. In order to create a gradient between the intraparenchymal pressure (Pp) and the ventricular pressure (Pcsf) such that Pp>Pcsf, the ventricular pressure was vented outside the hyperbaric chamber into a container with sterile saline solution which was maintained at a height of 150 mm above the ventricles, so that ventricular pressure would be constantly maintained at 150 mm $H_2O$, regardless of the hyperbaric chamber's pressure.

Before increasing the pressure inside the hyperbaric chamber above atmospheric pressure, the values of the parenchymal pressure (Pp), ventricular pressure (Pcsf) and right atrial pressure (Pc) were measured and from that moment in time, these values were constantly measured, as illustrated in the left diagram of FIG. 31. The pressure of the chamber was slowly increased to a value of 250 mm $H_2O$ above atmospheric pressure and was kept at this value for a period of 90 minutes. As illustrated in the right diagram of FIG. 31, when the chamber's pressure was increased, all the parameters which were being measured also increased by an amount of 250 mm $H_2O$ over the values that were measured before the chamber was pressurized, except the ventricular pressure (Pcsf) which was vented to the outside of the chamber and constantly remained at a value of approximately 150 mm $H_2O$.

Figure 32:
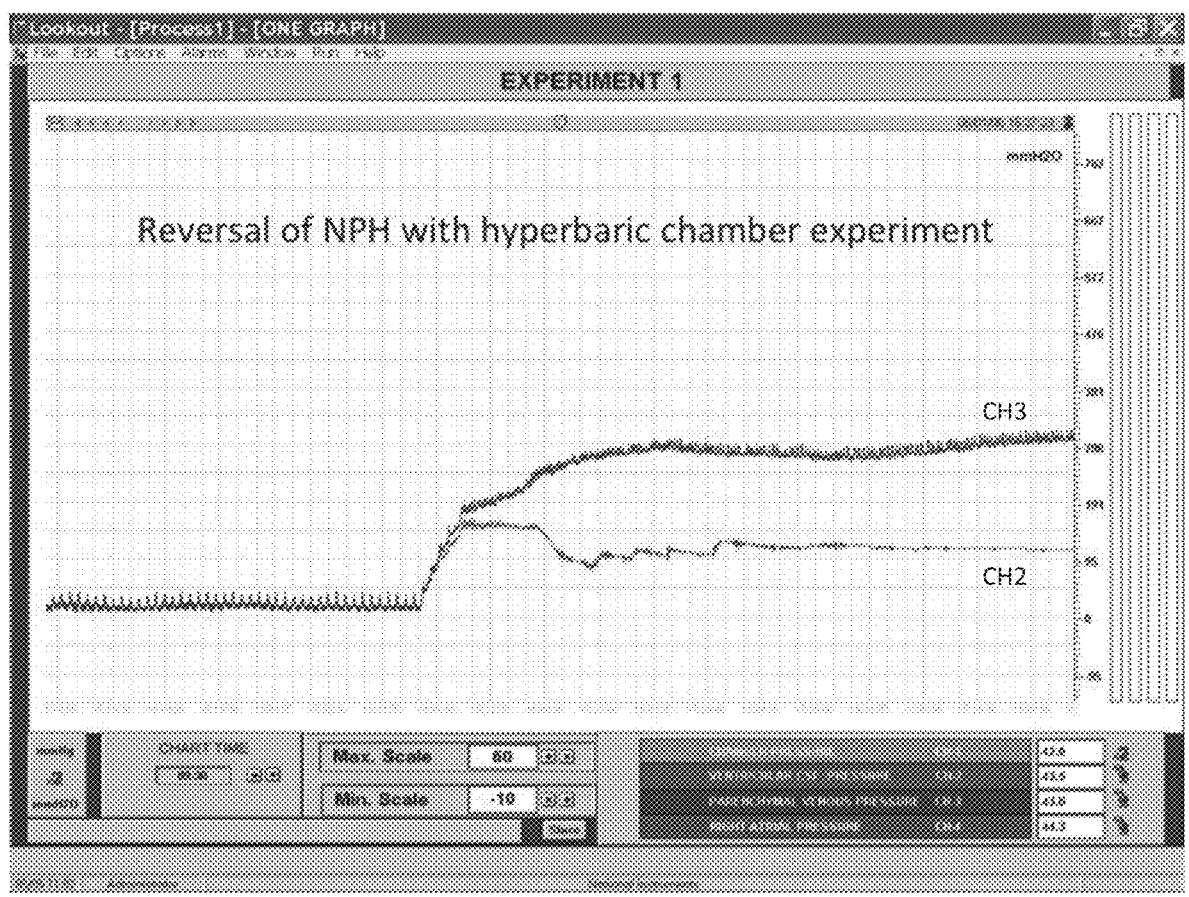
FIG. 32 depicts the pressure gradient when NPH was reversed using a hyperbaric chamber, when CSF was vented to the outside of the chamber.

As illustrated in FIG. 32, the pressure gradient, which was created between the ventricular CSF and the parenchymal veins, is clearly seen. While the ventricular pressure (Pcsf) was kept at a normal value of approximately 150 mm $H_2O$, the parenchymal venous pressure (Pp) was kept at approximately 320 mm $H_2O$.

Figure 33:
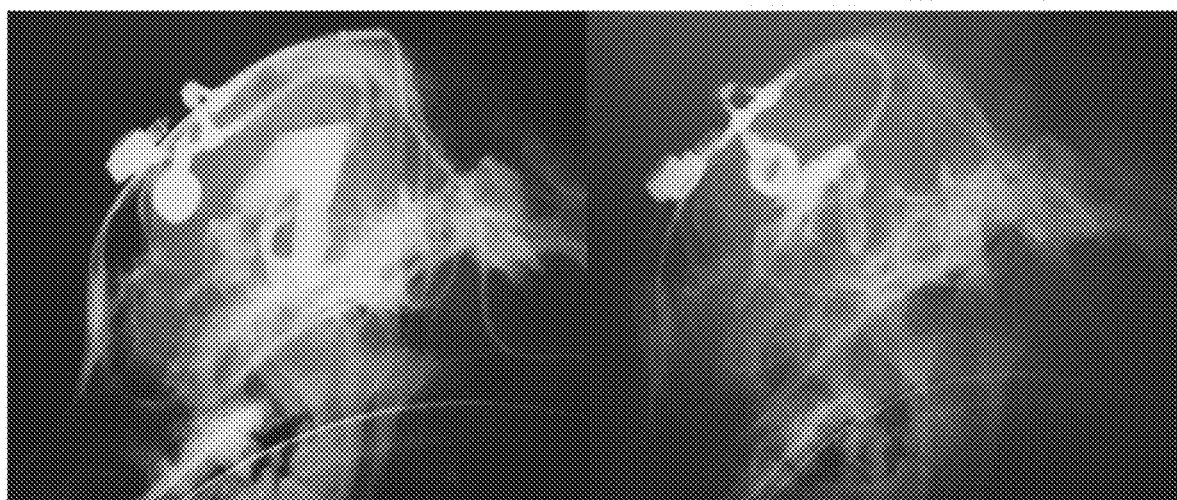
FIG. 33, left panel, illustrates a lateral X-Ray of the dog's head with the enlarged ventricles, just before the pressure of the hyperbaric chamber is increased. The right panel illustrates a lateral X-Ray of the dog's head 90 minutes after being in the hyperbaric chamber.

The left picture of FIG. 33 illustrates a lateral X-Ray of the dog's head with the enlarged ventricles, just before the pressure of the hyperbaric chamber is increased. The right image of FIG. 33 illustrates a lateral X-Ray of the dog's head 90 minutes after being in the hyperbaric chamber under the influence of a gradient of 120 mm $H_2O$ between Pp and Pcsf, in which Pcsf had a value of approximately 150 mm $H_2O$ and Pp had a value of approximately 320 mm $H_2O$.

As seen in FIG. 33, one can easily compare the two lateral X-Rays; one taken 90 minutes after the other and after being under the influence of the hyperbaric chamber's pressure. It is an unexpected result that the ventricles went back to normal size in only this short period of time.

It is important to note that during this experiment, both during the production of hydrocephalus (ventricular enlargement) as well as during the reversal of hydrocephalus (ventricular regression), the ventricular pressure (Pcsf) was at all times kept at its normal value, and only the parenchymal pressure was modified. From this, one can conclude that indeed it is the gradient between these two pressures, Pcsf and Pp, which controls ventricular size. When Pcsf>Pp, the ventricles will enlarge, even if Pcsf is at a normal value and Pp is below its normal value. When Pcsf<Pp, the ventricles will decrease in size, even if Pcsf is at its normal value and Pp is greater than normal.

In conclusion, Normal Pressure Hydrocephalus occurs because, even though Pcsf remains at its normal value, Pp is below its normal value and a gradient between these two pressures produces ventricular enlargement.

Example 6: Autologous Blood Injected into the Cisterna *Magna* (Equivalent to Subarachnoid Hemorrhage) Produces Normal Pressure Hydrocephalus A common cause of hydrocephalus and normal pressure hydrocephalus is a subarachnoid hemorrhage. A method that simulates this cause, the injection of autologous blood into the cisterna *magna*, was chosen to produce hydrocephalus in laboratory animals. A gauge 22 needle was placed into the cisterna *magna*, and 1 ml of CSF was removed. Fresh autologous venous non-heparinized blood (2 ml) was injected at a rate of 2 ml/minute. This procedure was performed every four days for a total of six times.

Figure 34:
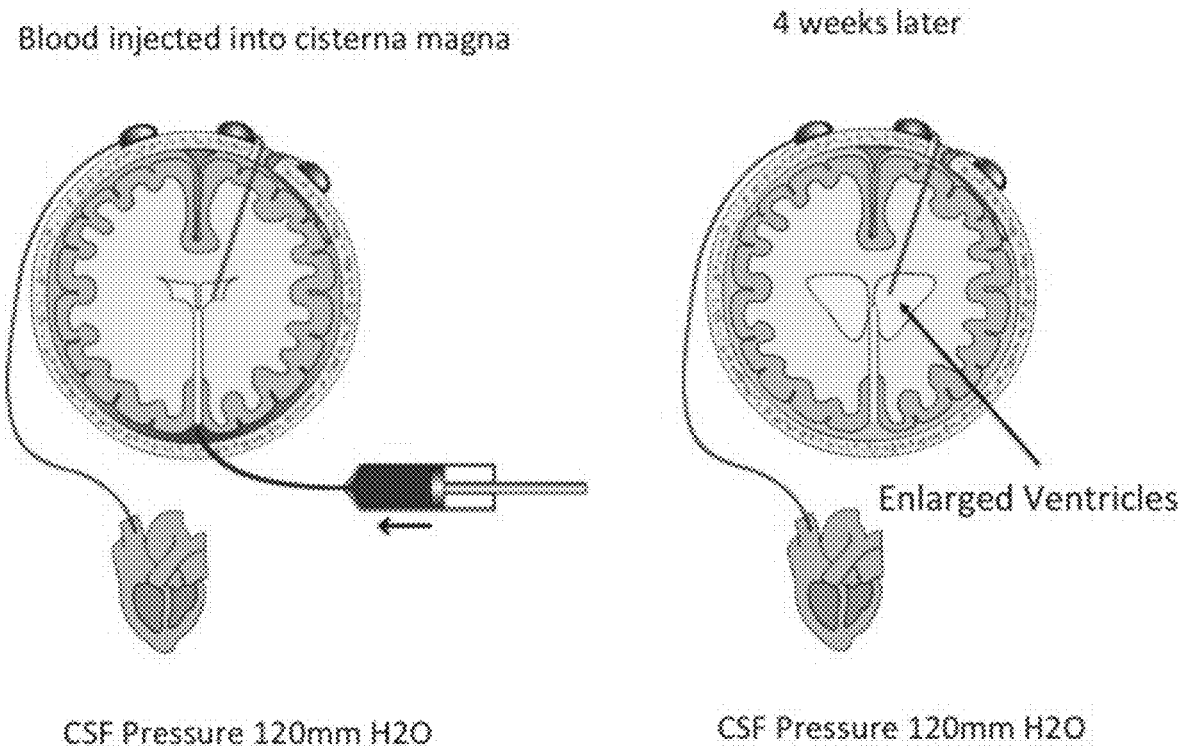
FIG. 34 illustrates the experimental setup for producing NPH by injecting autologous blood into the cistern *magna*.

Ventricular pressure (Pcsf) was monitored every day and was constantly measured as normal at approximately 150 mm $H_2O$. To assess ventricular size, X-Rays were taken every four days, after introducing contrast medium into the ventricles. As illustrated in FIG. 34, the dogs developed normal pressure hydrocephalus approximately two weeks after commencement of the blood injections.

Since the ventricular pressure was measured as normal during the whole time in which normal pressure hydrocephalus was developing, it was concluded that no obstruction to the flow of CSF was occurring during this process. Therefore, it was concluded that for the ventricles to enlarge with a normal CSF pressure, the parenchymal venous pressure was probably being reduced below its normal level, in order to produce a pressure gradient such that Pcsf>Pp, and produce ventricular enlargement. This could happen if the veins in the subarachnoid space had become hardened due to the exposure of the blood around them, after having injected the blood into the cisterna *magna*, which had most probably flowed into the subarachnoid space.

Example 7: Detection of Collagen on Subarachnoid Veins in Bilateral or Unilateral NPH in Dogs One particular case of interest was that of a dog which developed unilateral hydrocephalus, that is, hydrocephalus on only one side of the brain.

Figure 35A:
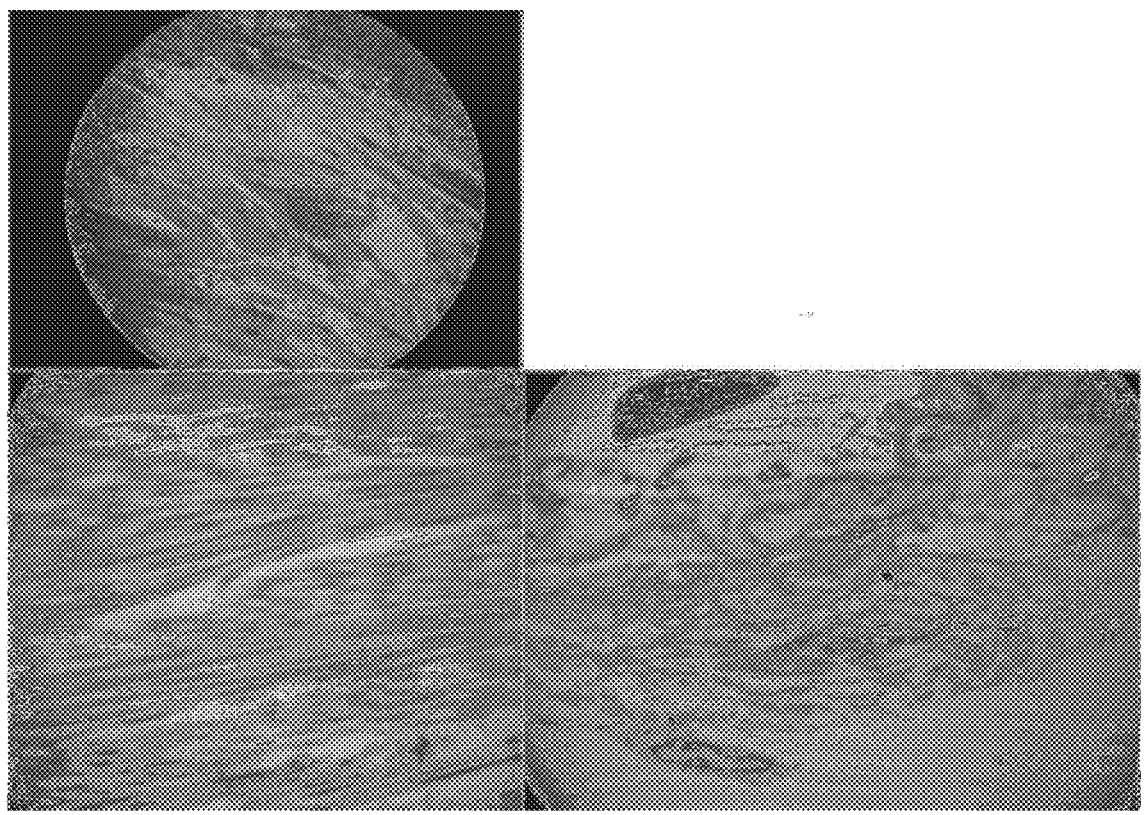
FIGS. 35A, 35B, 35C, and 35D show collagen fibers present in the veins affected by normal pressure hydrocephalus.

Studies were performed using the electron microscope on the adventitia of the subarachnoid veins of cases that had developed NPH. As seen in FIG. 35A, these studies with the electron microscope clearly show that the amount of collagen fibers present in the veins that were affected by NPH is much higher than the normal veins. Therefore, the walls of the veins appear to have become hardened due to the additional amount of collagen now present.

Figure 35B:
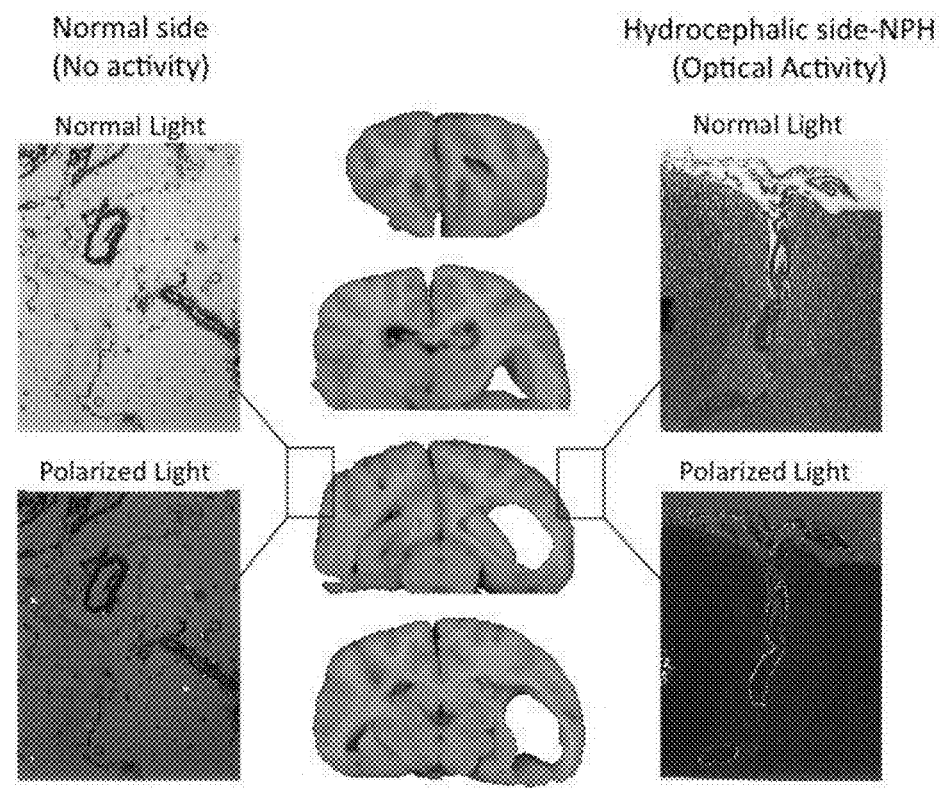
Figure 35C:
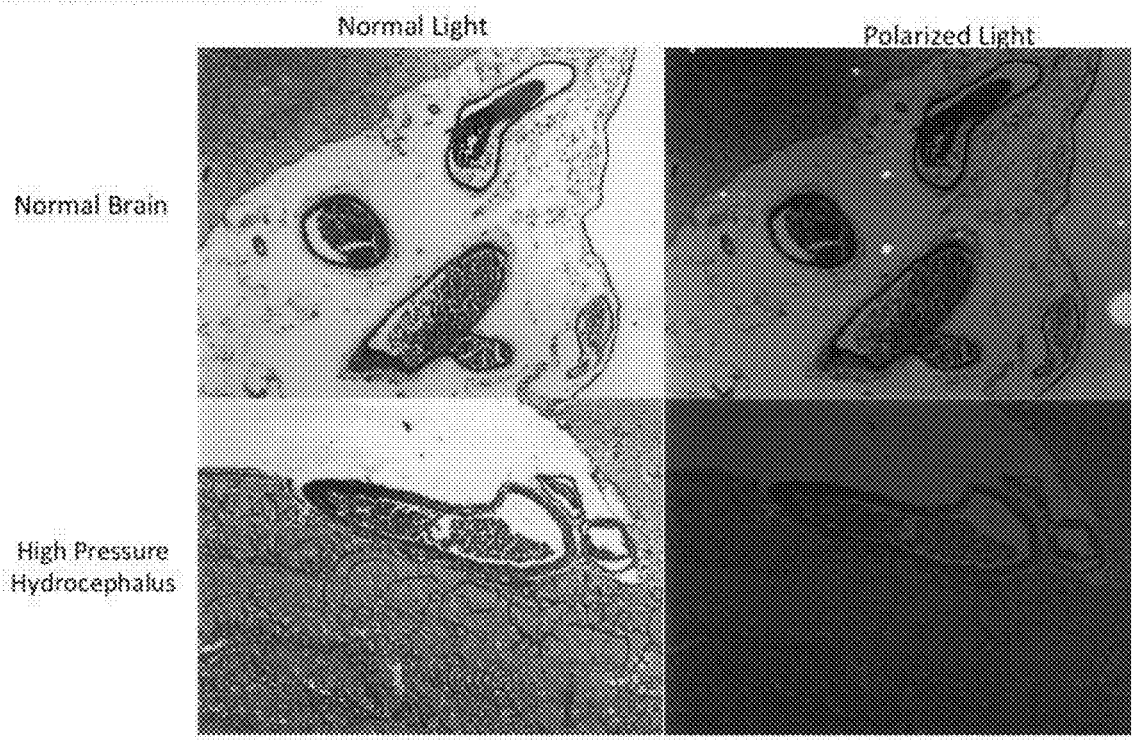
Figure 35D:
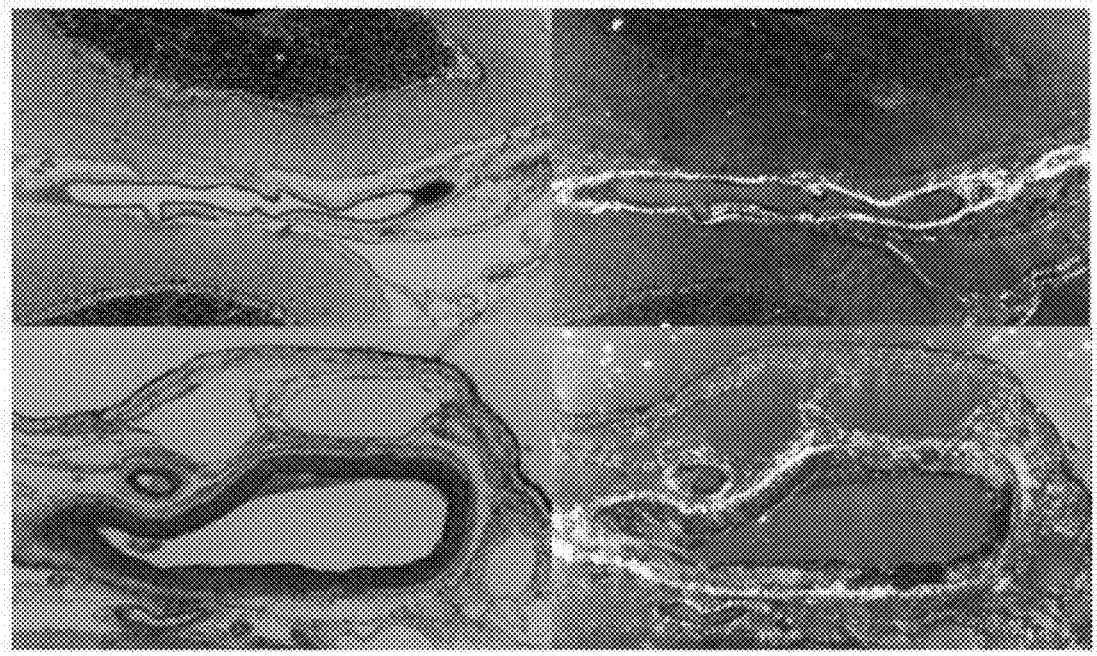

This would corroborate the hypothesis, which was earlier presented, that if the veins in the subarachnoid space become hardened, they will not be able to collapse under the surrounding pressure of the CSF in the subarachnoid space and therefore, the CSF pressure will not be transmitted to these veins and the parenchymal pressure will now be reduced to the pressure of the SSS. FIG. 35B shows the cross section of a dog's brain, in which normal pressure hydrocephalus only developed on one side. Upon examination of the veins with polarized light, the side of the brain that developed hydrocephalus was observed to show a marked optical activity, whereas the side that did not develop hydrocephalus does not show optical activity. FIG. 35C illustrates both veins from a normal brain and from a brain with High Pressure Hydrocephalus, as seen under normal light and under polarized light. There is no optical activity on the adventitia of the veins from the normal brain or the one with High Pressure Hydrocephalus. FIG. 35D shows the optical activity on the veins from two brains with NPH. The optical activity is due to the accumulation of collagen on the outer layer of the vein walls.

Example 8: In Vitro Experiment with Material that Simulates Veins

Figure 36:
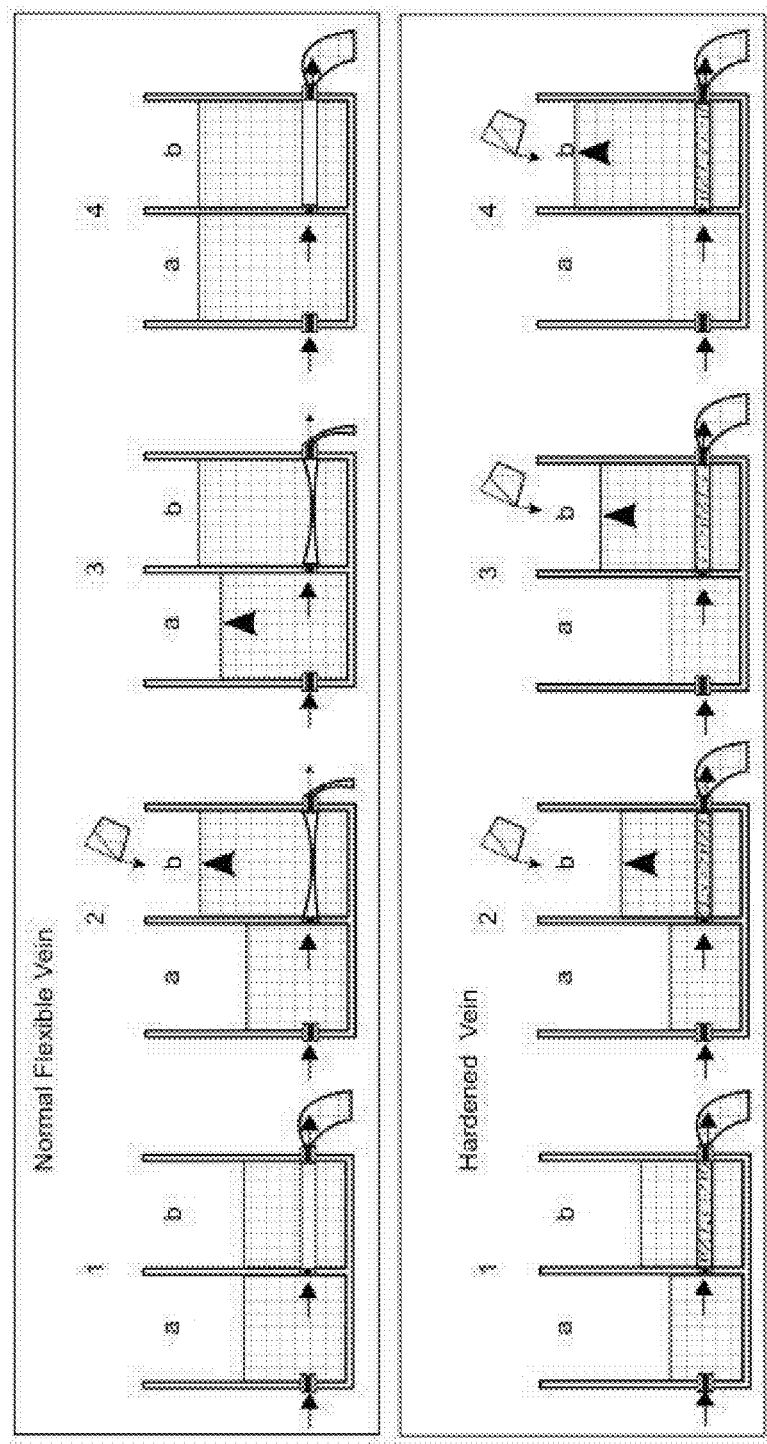
FIG. 36 illustrates an apparatus used as an in vitro model for vein flexibility.

In order to study the significance that the flexibility, or degree of hardness, the veins in the subarachnoid space might have over the intraparenchymal venous pressure, an in-vitro experiment was done. An acrylic container, with a vertical division, was built, as illustrated in FIG. 36. This container had two distinct compartments, a left one (a) and a right one (b). A very thin-walled and soft tube, such as the ones used for the outer cover of hot dogs or sausages, was used to connect the inlet and the outlet of compartment (b). The fluid that goes into compartment (a), must exit through this thin-walled tube in compartment (b). It is important to note that compartment (a) represents the intraparenchymal venous pressure and compartment (b) represents the subarachnoid space and the fluid within this compartment represents the CSF pressure in the subarachnoid space. The thin-walled tube represents the subarachnoid veins flowing through the subarachnoid space.

Looking at the sequence of events illustrated in the top drawings of FIG. 36, which are for a normal flexible vein, the following is observed. First, if the level of compartment (b) is as illustrated, as fluid goes into compartment (a), the level of compartment (a) will increase in height up to the level of the height found in compartment (b), at which point the "collapsed tube" in (b) will open up and allow flow. Thereafter, both level (a) and level (b) will continue equal.

Second, if the height of the fluid of compartment (b) is increased, as illustrated, then the thin-walled tube will collapse, due to the fact that its external pressure is greater than its internal pressure. Therefore, the level of compartment (a) will start to increase in height and parallel the level of compartment (b). The level of compartment (a) will continue to increase until this level has once more reached the height of the level in compartment (b) and both levels of compartments (a) and (b) will now continue equal until another change in the level of (b) occurs.

Once this thin-walled tube has hardened, similar to what occurs in the subarachnoid veins in the cases of NPH, this feedback mechanism is lost. As illustrated on the bottom drawings of FIG. 36, which shows the same experiment as above, but in this case with a hardened tube or "vein", no matter how high the level of compartment (b) is increased, this will not influence at all the level of compartment (a), since the veins are hardened and have become insensitive to the influence of the outer pressure exerted by the fluid surrounding them. The level of the fluid in compartment (a) will now be mandated by the pressure into which the fluid from this compartment is now draining into, which in the context of a patient, would be the pressure of the SSS, which is lower than the pressure of the CSF in the subarachnoid space.

Example 9: Observations in Patients with Open Bone Cranial Defect

The main objective of the observations and experiences presented in this section is to create awareness of the significance of the veins within the cranial cavity from a hydraulic point of view and the magnitude that a problem within the cranial venous system is capable of producing.

Figure 37:
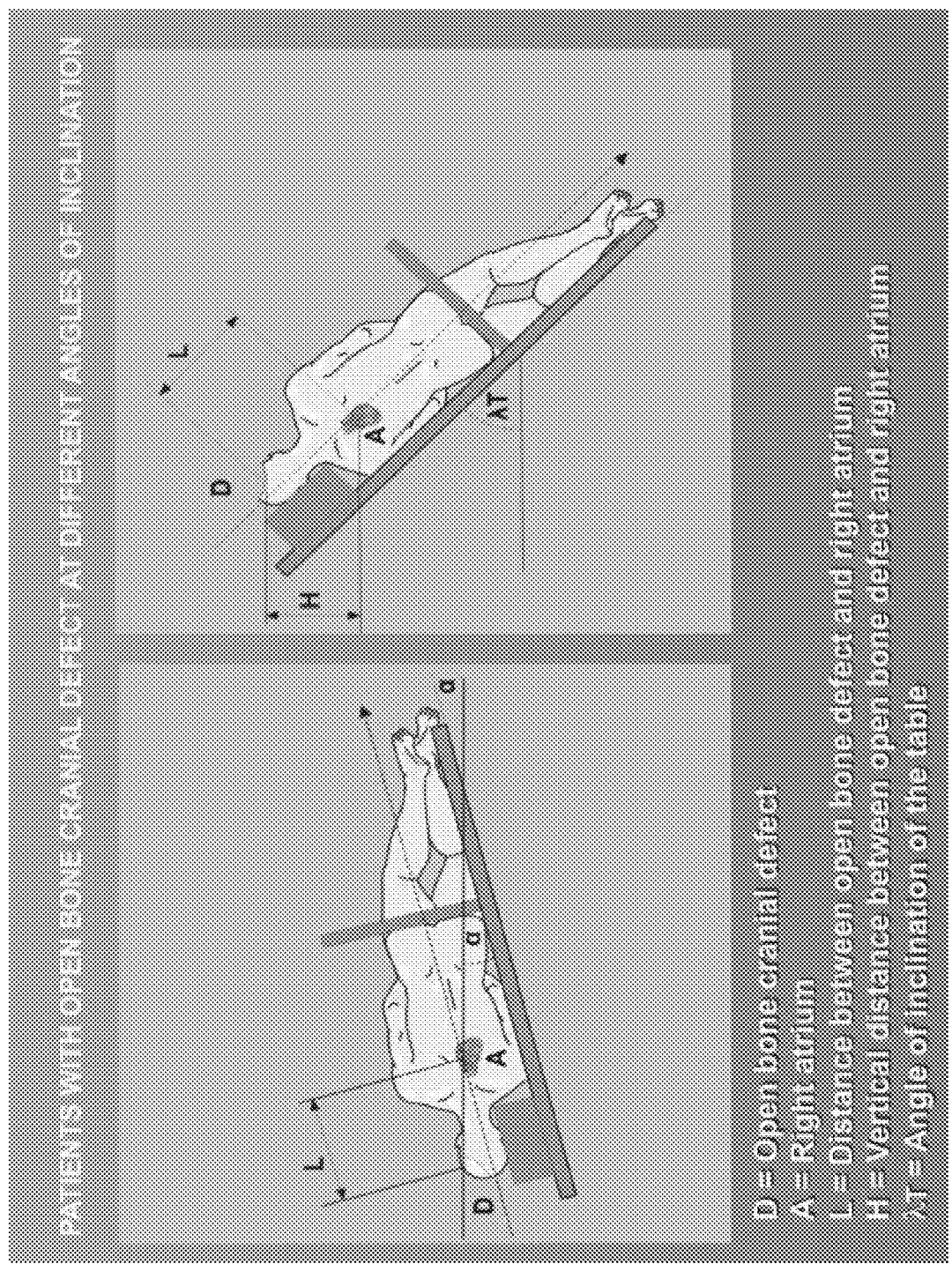
FIG. 37 illustrates the experimental setup for observing changes in pressure in the brains of patients with an open bone cranial defect.
Figure 38:
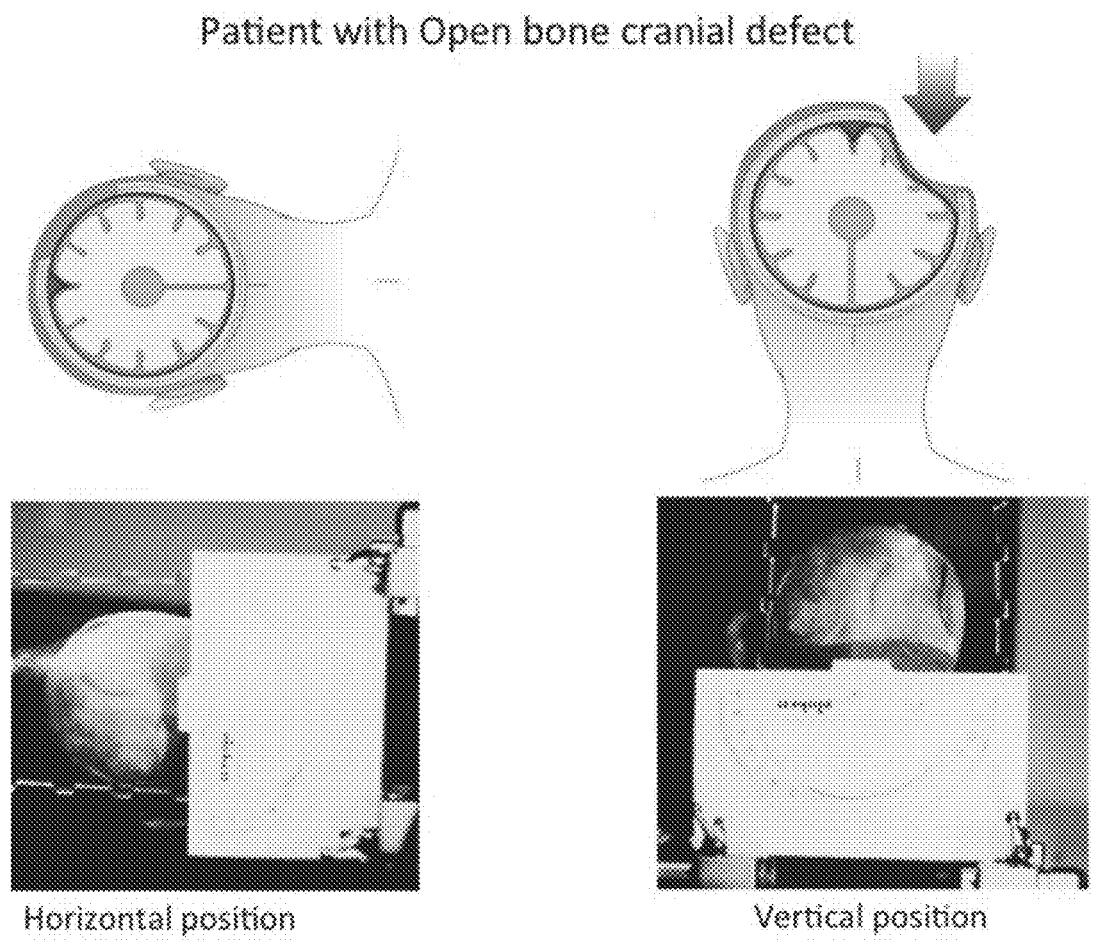
FIG. 38 illustrates the difference in brain volume in patients at horizontal and vertical positions.

A group of patients with large (70 mm diameter minimum) cranial bone defects, who had undergone craniotomy and had part of the skull removed, but who otherwise had no major neurological deficit, was selected. Where there is an absence of bone, the scalp becomes attached to the dura matter, and thus the displacement of this membrane is transmitted to the pliable scalp, especially when no scarring tissue has formed. In this manner, intracranial pressure (more precisely intraparenchymal pressure) will be transmitted to the scalp and thus can be measured. The scalp, at the location of the bone defect, becomes quite depressed when such patients stand or sit upright, as illustrated in FIGS. 37 and 38. In contrast, a short time with the patient in a slightly head down position restores the scalp and dura to an expanded position once more. This filling out of the defect has to be related to the cranial cavity regaining volume by drawing easily accessible venous blood into the vascular bed just beneath the scalp and dura, that is, the superficial and intraparenchymal venous blood of the brain and probably some CSF.

The larger the bone defect in the patient, the greater the depression of the scalp when the person stands or sits upright. Some patients had cranial trauma and a large portion of the skull, on both sides, had to be temporarily removed, with only the skull portion over the SSS remaining.

Figure 39:
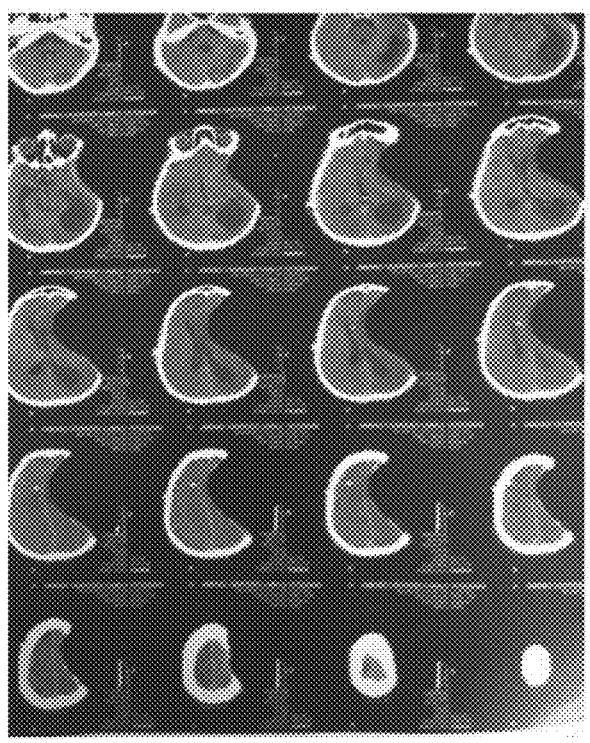
FIG. 39 depicts MRI images of a patient with an open bone cranial defect and the cross-sections derived from the MRI images.
Figure 39:
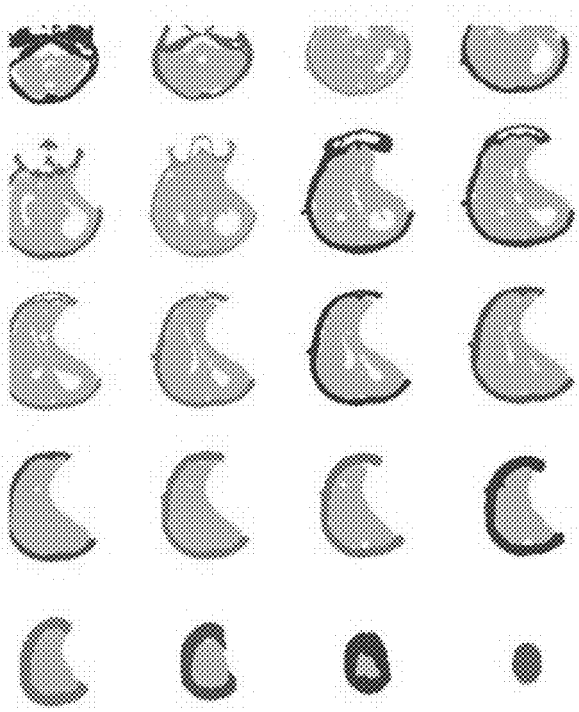

An MRI of the patient's head was performed with the patient in a slight vertical position of approximately 30° head up. The MRI is illustrated in FIG. 39. Notice the marked depression where the bone defect is located. From these MRI scan cross-sections, the equivalent cross-sections for modeling were done (FIG. 39) in order to perform a 3D analysis.

Figure 40:
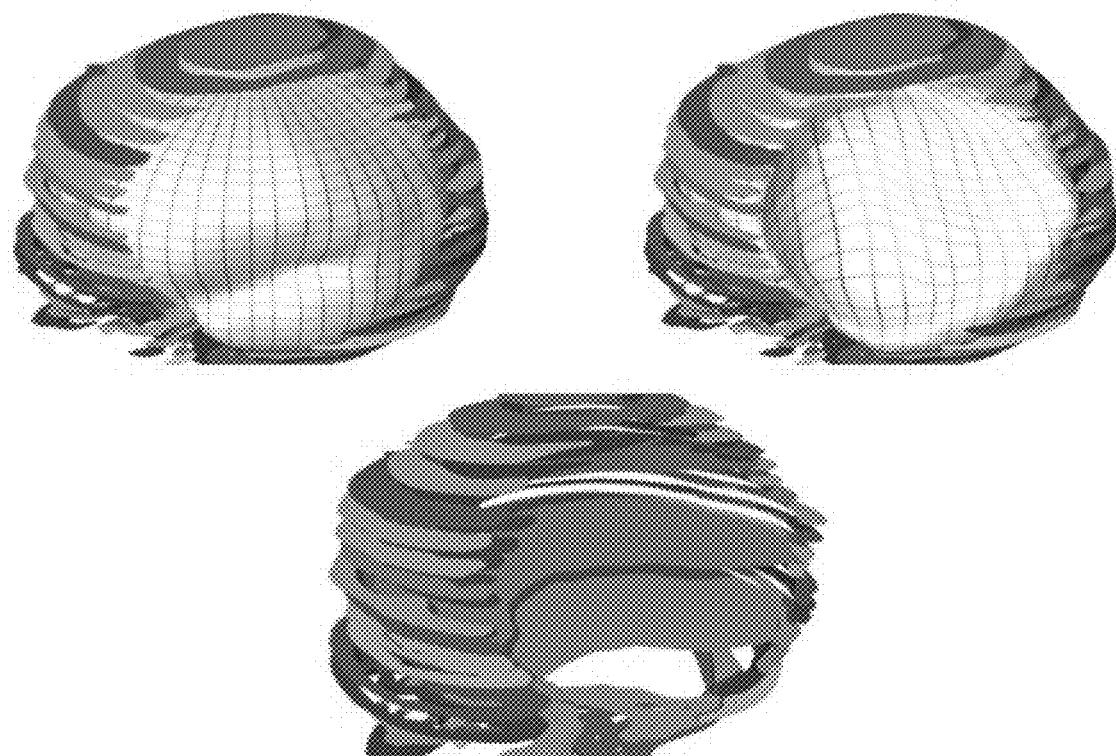
FIG. 40 illustrates the 3D analysis that was performed using the information gathered from the MRI sections.

FIG. 40 illustrates the 3D analysis that was performed using the information gathered from the MRI sections. It is interesting to notice that there is an approximate decrease in the contents of the cranial cavity, from a horizontal to a vertical position, of approximately 25% in this patient. In other patients in whom the whole top portion of the skull was removed, we would estimate that the decrease in cranial cavity volume from a horizontal to a vertical position was in the order of close to 50%. The majority of this volume must come from the venous blood exiting the parenchyma, since, together with the CSF, would basically constitute the only fluids contained in the cranial cavity, with a negative pressure when in a vertical position.

For the next experiments, a transparent suction cup made from Plexiglas and having a soft rubber seal around the 140 mm diameter border, was devised for placement against the scalp covering the cranial vault opening. Connected to the inside of the cup was a gauge, which measured differential pressure between interior and exterior of the cup. By means of this cup, negative pressures could be applied selectively to the region of the bone defect thereby determining the pressure needed to reposition the scalp to its normal state, depending on the patient's position.

The first portion of the experiments was performed with two patients in a hyperbaric chamber without using the suction cup. Each patient was placed in a sitting position while the chamber pressure was slowly increased up to 2 atmospheres. No change whatsoever was detected at the surface of the sunken scalp either during pressurization or de-pressurization of the chamber.

Figure 41:
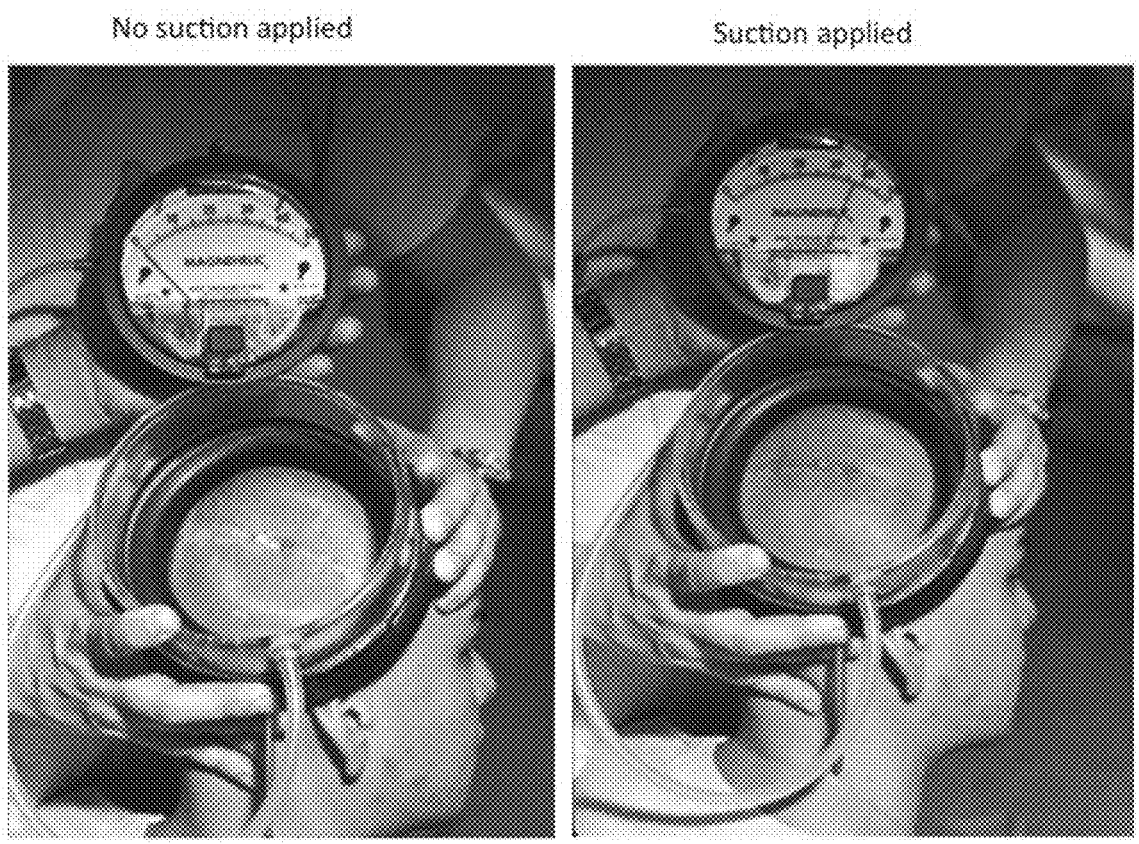
FIG. 41 illustrates the experimental setup for determining the pressure change required to reach normal curvature in patients with open bone cranial defects.

Next, while the hyperbaric chamber remained at atmospheric pressure, the transparent cup was placed on the bone defect. Suction was applied to the interior of the cup until the scalp regained its normal curvature. At that point, the reading on the suction gauge was noted (see FIG. 41).

Figure 42:
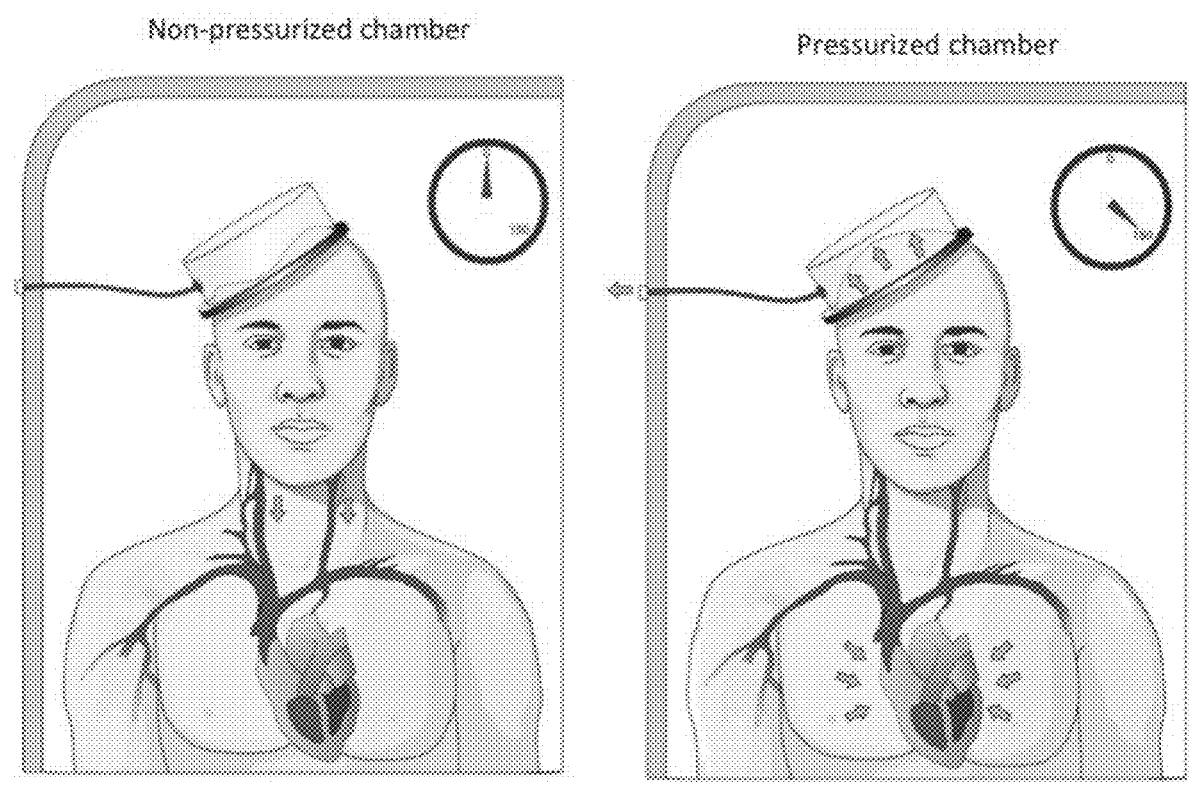
FIG. 42 illustrates the experimental setup for pressurized chamber experiments involving subjects with open bone cranial defects.

Afterwards, the defect was isolated with the same plastic cup, but this time the inside of the cup was vented outside the hyperbaric chamber to atmospheric pressure. In this way, the whole body, except the exterior side of the cranial defect, was exposed to the chamber's pressure. By pressurizing the chamber, it was noted that the same increment of pressure was required to push the defect to the normal curvature, as was the suction increment required when applied only to the area of the defect. In each of the two patients, the pressure, or suction, corresponded to that of a column of fluid measured vertically from the defect down to the right atrium, whose position was determined by X-ray, minus the intraparenchymal venous pressure in a horizontal position. The experimental setup is shown in FIG. 42. As mentioned earlier, the intraparenchymal venous pressure is equal to the CSF pressure. When suction is applied, the intraparenchymal vascular bed and CSF cavities refill to return the sunken defect to its normal position. The suction required to accomplish this is a direct measurement of both intraparenchymal (Pp) and CSF (Pcsf) pressures, at any degree of inclination.

Figure 43:
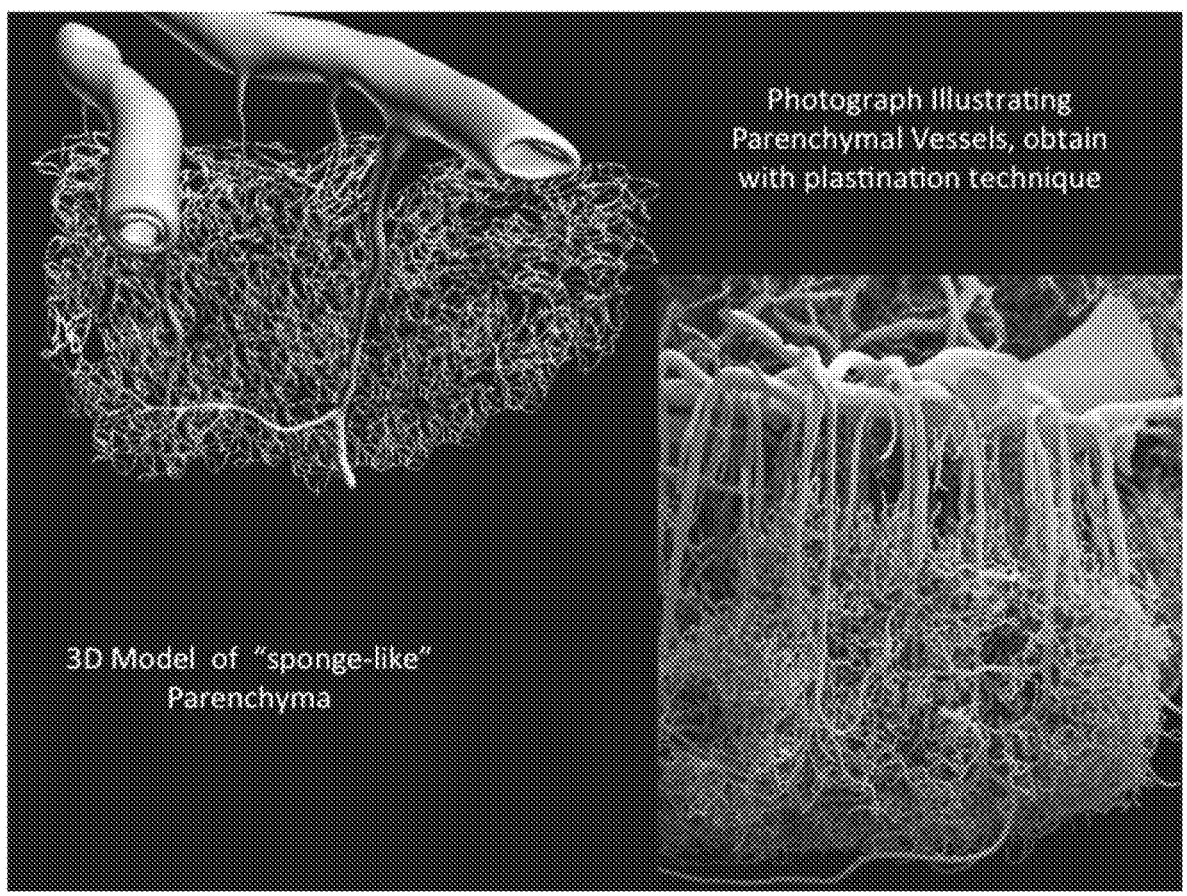
FIG. 43 illustrates the brain vasculature.

FIG. 43 illustrates the richness and density of the vasculature of the brain. The picture on the right is a photograph illustrating the parenchymal vessels, which was obtained with the plastination technique. The picture on the right is a 3D model of the "sponge-like" parenchyma. From the previous experiments and from these illustrations, one can easily conclude that the volume of blood within the brain, in particular, the venous blood, constitutes a large percentage of the total brain volume.

Figure 44:
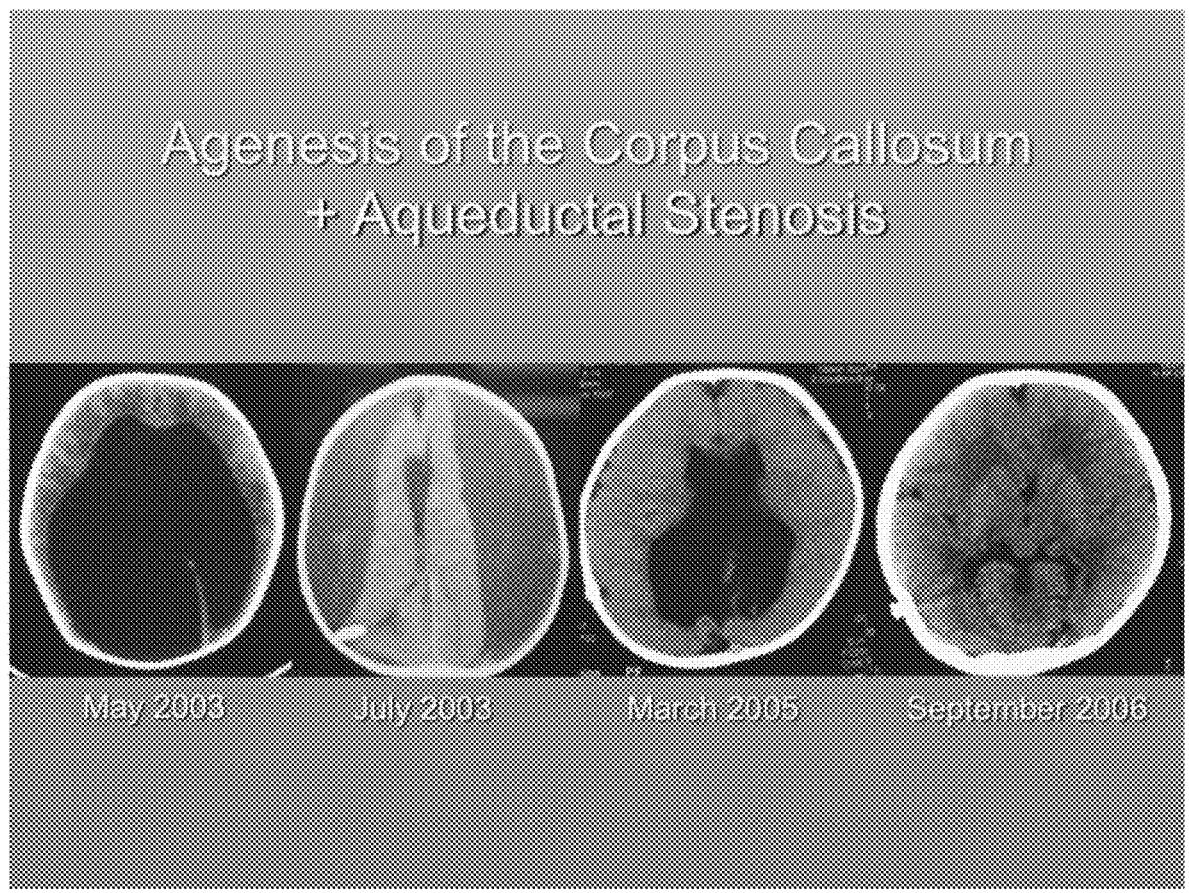
FIG. 44 depicts cross-sectional images of the brain of a patient who developed severe hydrocephalus and recovered upon treatment with a shunt.

Another interesting example that illustrates the ability of the brain to recuperate, particularly when referring to shifting of the volume of fluid from within the brain to the exterior and vice versa, is the one illustrated in FIG. 44. This is a patient who had Agenesis of the Corpus Callosum and Aqueductal Stenosis and therefore developed a severe hydrocephalus, as seen on May 2003. A shunt was implanted to correct the hydrocephalus, but the shunt's pressure was too low, and therefore the ventricles collapsed, as seen on July 2003. Afterwards, the pressure of the shunt was slowly increased and, as can be seen in March 2005, the ventricles increased in size and the brain tissue or parenchyma started to recuperate, or "fill-up". The pressure was slowly decreased and, in September 2006, the brain has almost completely recuperated. One can conclude that this has been a problem of "fluid shifting" to the outside of the parenchyma and later, back into the parenchyma.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating normal pressure hydrocephalus in a patient in need thereof, the method comprising:
   placing the patient in a hyperbaric chamber under conditions effective to increase an intraparenchymal venous pressure of the patient from a sub-normally low value to a normal value or to a value higher than normal, and
   venting cerebrospinal fluid (CSF) to an area with pressure lower than the hyperbaric chamber effective to control a CSF pressure in the patient to produce a pressure gradient having the intraparenchymal venous pressure above the CSF pressure.

2. The method of claim 1, wherein venting the CSF comprises venting the CSF via a ventricular shunt tap, lumbar tap, or spinal tap.

3. The method of claim 2, wherein the ventricular shunt tap comprises a ventricular catheter, a distal catheter, and an adjustable valve disposed between the ventricular catheter and the distal catheter.

4. The method of claim 3, wherein the ventricular shunt tap comprises a reservoir disposed between the adjustable valve and the ventricular catheter.

5. The method of claim 2, which comprises removing about 10-100 ml of CSF fluid.

6. The method of claim 1, wherein the area with pressure lower than the hyperbaric chamber is outside the hyperbaric chamber.

7. The method of claim 1, wherein the patient is characterized by having the sub-normally low value of intraparenchymal venous pressure, which is between 70 and 120 mm $H_2O$, and a normal value of the CSF pressure.

8. The method of claim 7, wherein the normal value of the CSF pressure is between 120 and 150 mm $H_2O$.

9. The method of claim 1, wherein the patient is placed in the hyperbaric chamber under conditions effective to increase the intraparenchymal venous pressure of the patient to a value having a difference between the CSF pressure and the intraparenchymal venous pressure of less than 50 mm $H_2O$.

10. The method of claim 1, wherein the patient is placed in the hyperbaric chamber under conditions effective to increase the intraparenchymal venous pressure to above the CSF pressure and the CSF is vented under conditions effective to substantially maintain a normal value of the CSF pressure.

11. The method of claim 10, wherein the patient is placed in the hyperbaric chamber under conditions effective to increase the intraparenchymal venous pressure to at least 10 mm H$_2$O above the CSF pressure.

12. The method of claim 1, wherein venting the CSF comprises implanting an externally programmable valve into a brain of the patient such that CSF can exit through the externally programmable valve.

13. The method of claim 12, wherein the externally programmable valve is a differential pressure valve adjustable by an externally applied rotating magnetic field.

14. The method of claim 1, further comprising administering an anti-fibrotic agent to the patient in an effective amount to increase flexibility of subarachnoid veins and/or arteries of the patient or reduce fibrosis of the subarachnoid veins.

15. The method of claim 1, further comprising administering an anti-collagen antibody to the patient in an effective amount to inhibit collagen accumulation and/or degrade collagen surrounding subarachnoid veins.

16. A method of treating normal pressure hydrocephalus in a patient in need thereof, the method comprising: placing a compression boot around legs, feet, or both of legs and feet of the patient under conditions effective to increase an intraparenchymal venous pressure of the patient from a sub-normally low value to a normal value or to a value higher than normal; and
    venting cerebrospinal fluid (CSF) under conditions effective to control a CSF pressure in the patient to produce a pressure gradient having the intraparenchymal venous pressure above the CSF pressure.

17. The method of claim 16, which further comprises draining CSF from the patient through a ventricular shunt tap, lumbar tap, or spinal tap.

18. The method of claim 17, wherein the ventricular shunt tap comprises a ventricular catheter, a distal catheter, an adjustable valve disposed between the ventricular catheter and the distal catheter, and a reservoir disposed between the adjustable valve and the ventricular catheter.

19. A method of treating normal pressure hydrocephalus in a patient in need thereof, the method comprising:
    performing a compression of the jugular veins when the patient is lying at an incline of +35° or less under conditions effective to increase an intraparenchymal venous pressure of the patient from a sub-normally low value to a normal value or to a value higher than normal; and
    venting cerebrospinal fluid (CSF) under conditions effective to control a CSF pressure in the patient to produce a pressure gradient having the intraparenchymal venous pressure above the CSF pressure.

20. The method of claim 19, which further comprises draining CSF from the patient through a ventricular shunt tap, lumbar tap, or spinal tap.

21. The method of claim 20, wherein the ventricular shunt tap comprises a ventricular catheter, a distal catheter, an adjustable valve disposed between the ventricular catheter and the distal catheter, and a reservoir disposed between the adjustable valve and the ventricular catheter.

* * * * *